(12) United States Patent
Israeli et al.

(10) Patent No.: US 6,953,668 B1
(45) Date of Patent: Oct. 11, 2005

(54) PROSTATE-SPECIFIC MEMBRANE ANTIGEN

(75) Inventors: Ron S. Israeli, Staten Island, NY (US); Warren D. W. Heston, New York, NY (US); William R. Fair, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 08/466,381

(22) Filed: Jun. 6, 1995

Related U.S. Application Data

(63) Continuation of application No. 08/403,803, filed on Mar. 17, 1995, and a continuation of application No. PCT/US93/10624, filed on Nov. 5, 1993, which is a continuation-in-part of application No. 07/973,337, filed on Nov. 5, 1992, now abandoned.

(51) Int. Cl.[7] .................. C12Q 1/68; G01N 33/574; C12P 19/34; C07H 21/04
(52) U.S. Cl. .................. 435/7.23; 435/6; 435/91.2; 536/24.31
(58) Field of Search .................. 435/6, 91.2, 7.23; 536/24.31

(56) References Cited

U.S. PATENT DOCUMENTS

| | | |
|---|---|---|
| 4,554,101 A | 11/1985 | Hopp |
| 4,939,240 A | 7/1990 | Chu et al. |
| 5,162,504 A | 11/1992 | Horoszewicz |
| 5,538,866 A | 7/1996 | Israeli et al. |
| 5,672,592 A | 9/1997 | Jackson et al. |
| 5,773,292 A | 6/1998 | Bander |
| 5,795,877 A | 8/1998 | Jackson |
| 5,804,602 A | 9/1998 | Slusher et al. |
| 5,863,536 A | 1/1999 | Jackson et al. |
| 5,880,112 A | 3/1999 | Jackson et al. |
| 5,902,817 A | 5/1999 | Jackson et al. |
| 5,935,818 A | 8/1999 | Israeli et al. |
| 5,939,258 A | 8/1999 | Croce et al. |
| 5,962,521 A | 10/1999 | Jackson et al. |
| 5,968,915 A | 10/1999 | Jackson et al. |
| 5,981,209 A | 11/1999 | Slusher et al. |
| 6,011,021 A | 1/2000 | Slusher et al. |
| 6,017,903 A | 1/2000 | Slusher et al. |
| 6,025,344 A | 2/2000 | Jackson et al. |
| 6,025,345 A | 2/2000 | Jackson et al. |
| 6,046,180 A | 4/2000 | Jackson et al. |
| 6,054,444 A | 4/2000 | Jackson et al. |
| 6,103,463 A | 8/2000 | Chetverin et al. |
| 6,107,090 A | 8/2000 | Bander |
| 6,121,252 A | 9/2000 | Jackson et al. |
| 6,136,311 A | 10/2000 | Bander |
| 6,150,508 A | 11/2000 | Murphy et al. |
| 6,271,245 B1 | 8/2001 | Jackson et al. |
| 6,288,046 B1 | 9/2001 | Jackson et al. |
| 6,348,464 B1 | 2/2002 | Jackson et al. |
| 6,372,726 B1 | 4/2002 | Slusher et al. |
| 6,384,022 B1 | 5/2002 | Jackson et al. |
| 6,395,718 B1 | 5/2002 | Slusher et al. |
| 6,413,948 B1 | 7/2002 | Slusher et al. |
| 6,452,044 B2 | 9/2002 | Jackson et al. |
| 6,458,775 B1 | 10/2002 | Jackson et al. |
| 6,479,471 B1 | 11/2002 | Jackson et al. |
| 6,569,432 B1 | 5/2003 | Israeli et al. |
| 6,586,623 B2 | 7/2003 | Tsukamoto et al. |
| 6,649,163 B1 | 11/2003 | Bander |
| 2001/0044459 A1 | 11/2001 | Jackson et al. |
| 2002/0013295 A1 | 1/2002 | Slusher et al. |
| 2002/0015704 A1 | 2/2002 | Bander |
| 2002/0019430 A1 | 2/2002 | Jackson et al. |
| 2002/0151503 A1 | 10/2002 | Slusher et al. |
| 2003/0003101 A1 | 1/2003 | Bander et al. |
| 2003/0007974 A1 | 1/2003 | Nanus et al. |
| 2003/0017965 A1 | 1/2003 | Slusher et al. |
| 2003/0031673 A1 | 2/2003 | Bander |
| 2003/0064912 A1 | 4/2003 | Slusher et al. |
| 2003/0083374 A1 | 5/2003 | Jackson et al. |
| 2003/0105088 A1 | 6/2003 | Tsukamoto et al. |
| 2003/0216468 A1 | 11/2003 | Tsukamoto et al. |
| 2004/0001846 A1 | 1/2004 | Israeli et al. |
| 2004/0024188 A1 | 2/2004 | Murphy et al. |

FOREIGN PATENT DOCUMENTS

| | | |
|---|---|---|
| EP | 0173951 | 12/1986 |
| WO | WO9409820 | 5/1994 |
| WO | 9626272 | 8/1996 |
| WO | WO9735616 | 10/1997 |
| WO | WO9947554 | 9/1999 |
| WO | 02096460 | 12/2002 |
| WO | 02098897 | 12/2002 |

OTHER PUBLICATIONS

Lazar et al. Mol. Cell Biology 8(3):1247–62, Mar. 1988.*
Bowie et al. Science 247:1308–1310, Mar. 1990.*
Kumar et al. PNAS 87:1337–1341, Feb. 1990.*
Abdel–Nabi, H., et al. (1992) "Monoclonal Antibodies and Radioimmunoconjugates in the Diagnosis and Treatment of Prostate Cancer", Seminars on Urology 127: 45–54 (Exhibit 5).

(Continued)

*Primary Examiner*—Michael Pak
*Assistant Examiner*—Stephen Gucker
(74) *Attorney, Agent, or Firm*—John P. White, Esq.; Cooper & Dunham LLP

(57) ABSTRACT

This invention provides for an isolated mammalian nucleic acid molecule encoding a mammalian prostate-specific membrane antigen. This invention provides for nucleic acid probes which specifically hybridize with the nucleic acid molecule encoding said antigen. This invention provides for a method of detecting hematogenous micrometastic tumor cells of a subject performing the polymerase chain reaction (PCR) on samples of the subject using primers of said antigen. This invention provides for methods to identify ligands which bind to said antigen. This invention provides for the prevention and/or treatment of prostate tumor growth.

7 Claims, 48 Drawing Sheets

OTHER PUBLICATIONS

Axelrod, H. R., et al. (1968) "Preclinical Results and Humman Immunohitochemical Studies With 90Y–CYT–356: A New Prostate Cancer Therapeutic Agent" AUA 87th Annual Meeting, May 10–14, 1992 (Exhibit 6).

Carter, B.H. And Coffey, D.S. (1990) "The Prostate: An Increasing Medical Problem" The Prostate 16:39–48 (Exhibit 7).

Feng, Q., et al. (1991) "Purification and Biochemical Characterization of the 7E11–C5 Prostate Carcinoma–Associated Antigen", Proceedings of the American Association for Cancer Research 32:239 (Exhibit 8).

Chang, Chawnshang, et al. (1988) "Structural Analysis of Complementary DNA and Amino Acid Sequences of Human and Rat Androgen Receptors", Proc. Natl Acad. Sci USA 85:7211–7215 (Exhibit 9).

Culver, K.W., et al. (1992) "In Vivo Gene Transfer with Retoviral Vector–Producer Cells for Treatment of Experimental Brain Tumors", Science 256:1150–1552 (Exhibit 10).

Decensi, A., et al. (1991) "Phase II Study of the Pure Non–steroidal Antiandrogen Nilutamide in Prostatic Cancer", Eur J Cancer 27:1100–1104 (Exhibit 11).

Faber, P.W., et al. (1991) "Characterization of the Human Androgen Transciption Unit" The Journal of Biological Chemistry 266:10743–10749 (Exhibit 12).

Fey, Martin F., et al. (1991) "The Polymerase Chain Reaction: A New Tool for the Detection of Minimal Residual Disease in Haematological Malignancies" Eur J Cancer 27:89–94 (Exhibit 13).

Henttu, Pirkko and Vihko, Pirkko (1989) "cDNA Coding for the Entire Human Prostate Specific Antigen Shows High Homologies to the Human Tissue Kallikrein Genes" Biochemical and Biophysical Research Communications 160:903–910 (Exhibit 14).

Horoszewicz, Julius S., et al. (1987) "Monoclonal Antibodies to a New Antigen Marker in Epithelial Prostatic Cells and Serum of Prostatic Cancer Patients" AntiCancer Research 7:927–936 (Exhibit 15).

Huber, Brian E., et al (1991) "Retroviral–mediated Gene Therapy for the Treatment of Hepatocellular Carcinoma: An Innovative Approach for Cancer Therapy" Proc. Natl. Acad. Sci. USA 88:8039–8043 (Exhibit 16).

Israeli, Ron S., et al. (1994) "Expression of the Prostate Specific Membrane Antigen" Cancer Research 54:1807–1811 (Exhibit 17).

Israeli, Ron S., et al. (1994) "Sensitive Nested Reverse Transcription Polymerase Chain Reaction Detection of Circulating Prostatic Tumor Cells: Comparison of Prostate–specific Membrane Antigen and Prostate–specific Antigen–based Assays" Cancer Research 5:6306–6310 (Exhibit 18).

Keer, Harold N., et al. (1990) "Elevated Transferrin Receptor Content in Human Prostate Cancer Cell Lines Assessed In Vitro and In Vivo" The Journal of Urology 143:381–385 (Exhibit 19).

Lopes, A. Dwight., et al (1993) "Immonohistochemical and Pharmacokinetic Characterization of the Site–specific Immunocnjugate CYT–356 Derived from Antiprostate Monoclonal Antibody" Cancer Research 50: 6423–6429 (Exhibit 20).

Lubahn, Dennis B., et al. (1989) "Sequence of the Intron/exon junctions of the Coding Region of the Human Adrogen Receptor Gene and Identification of a Point Mutation in a family with Complete Androgen Insensitivity" Proc. Natl. Acad. Sci. USA 86:9534–9538 (Exhibit 21).

Lundwall, Ake and Lilja, Hans., (1987) "Molecular Cloning of Human Prostate Specific Antigen cDNA" FEBS Letters 214, No. 2:317–322 (Exhibit 22).

Mukhopadhyay, Tapas., et al. (1991)"Sepecific Inhibitionof K–ras Expression and Tumorigenicity of Lung Cancer Cells by Antisense RNA" Cancer Research 51:1744–1748 (Exhibit 23).

Riegman, P.H.J., et al. (1989) "The Prostate–Specific Antigen Gene and the Human Glandular Kallikrein–1 Gene and Tandemly Located on Chromosone 19" FEBS Letters vol. 247:123–126 (Exhibit 24).

Sharief, Farida S., et al. "Human Prostatic Acid Phosphatase: cDNA Cloning, Gene Mapping and Protein Sequence Homology With Lysosomal Acid Phoshatase" Biochemical and Biophysical Research Communications 160:79–86 (Exhibit 25); 1990.

Solin, Timo., (1990) "Gene Expression and Prostate Specificity of Human Prostatic Acid Phosphatase (PAP): Evaluation By RNA Blot Analuses" Biochemica et Biophysica Acta 1048:72–77 (Exhibit 26).

Troyer, John K., et al.(1994) "Biochemical Characterization and Mapping of the 7E11–C5.3 Epitope of the Prostrate Specific Membrane Antigen (PSMA)" Basic and Clinical Aspects of Prostate Cancer: Abstract C38 (Exhibit 27).

Su, S.L., et al. (1994) "Sensitive Detection of Prostatic Hematogenous Micrometastases Using Prostate Specific Antigen (PSA) and Prostate Specific Membrane Antigen (PSM) Derived parimeters in the Polymerase Chain Reaction" Proceedings of the American Association for Cancer Research 35:271 (Exhibit 28).

Vihko, Pirkko, et al (1988) "Molecular Cloning and Sequence Analysis of cDNA Encoding Human Prostatic Acid Phosphatase" FEBS Letters 236:275–281 (Exhibit 29).

Vile, Richard G. And Ian R. Hart., (1993) "In Vitro and In Vivo Targeting of Gene Expression to Melanoma Cells" Cancer Research 53:962–967 (Exhibit 30).

Israeli, Ron S., et al. (1994) "Expression of the Prostate Specific Membrane Antigen" Cancer Research 54:1807–1811 (Exhibit 31).

Waibel, R., et al. (1990) "Therapy of Small Cell Lung Cancer Xenografts in a Nude Mouse model: Evaluation of Radioimmunotherapy and Immonotoxin Therapyogy" Antibody Immunoconjugates and Radiopharmaceuticals 3:54 (Exhibit 32).

Watt, Kenneth W.K., et al (1986) "Human Prostate–Specific Antigen: Structural and Functional Similarity With Serine Proteases" Proc. Natl. Acad. Sci. USA 83:3166–3170 (Exhibit 33).

Wright, Jr., et al "Characterization of a New Prostate Carcinoma–Associated Marker" Antibody Immunoconjugates, and Radiopharmaceuticals 3:89 (Exhibit 34); 1989.

Young, Richard A. and Davis, Ronald W., "Efficient Isolation of Genes by Using Antibody Probes" Proc. Natl. Acad. Sci. USA 80:1194–1198 (Exhibit 35); 1986.

Israeli, R.S. et al., (1994) "Sensitive Detection of Prostatic Hematogenous Micro–Metastases Using Prostate Specific Antigen (PSA) And Prostate specific Membrane Antigen (PSM) Derived Primers in the Polymerase Chain Reaction (PCR)" J Urol 151:373A (Exhibit 36).

Israeli, R.S. et al., (1994) "Localization of the Prostate Specific Membrane Antigen (PSM) to the Putative Metastasis–Suppressor Region on Human Chromosome 11" J Urol 151:252A (Exhibit 37).

Corr, J.G. et al., (1994) "Prostate Specific Membrane Antigen (PSM) Expression in Orthotopically Implanted Human Prostate Cancer Cells in Nude Mice Slows Tumor Growth and Metastatic Potential" J Urol 151:492A (Exhibit 38).

Israeli, R.S. et al., (1994) "Localization of the Prostate Specific Membrane Antigen (PSM) to the Putative Metastasis–Suppressor Region on Human Chromosome 11" Proceedings of the American Association for Cancer Research 35:271 (Exhibit 39).

Israeli, R.S. et al., (1993) "Characterization of the Prostate–Specific Membrane Antigen (PSM)" Cancer Research 34:255 (Exhibit 40).

Israeli, R.S. et al., (1993) "Molecular Cloning and Characterization of a Prostate–Specific Membrane Antigen" J Urol 149:471A (Exhibit 41).

Israeli, R.S. et al., (1992) "Purification and Molecular Cloning of a New Prostate–Specific Antigen" Cancer Research 33:356 (Exhibit 42).

Bell, G.I., et al., "cDNA Sequence Coding For Human Kidney Catalase," *Nucleic Acids Research,* 14(13):5561–2 (1986).

Bowie, J.U., et al., "Deciphering The Message In Protein Sequences: Tolerance To Amino Acid Substitutions," *Science,* 147:1306–1310 (1990).

Garcia, G., et al., "Selenoprotein A Component Of The Glycine Reductase Complex From *Clostridium purinolyticum:* Nucleotide Sequence Of The Gene Shows That Selenocysteine Is Encoded By UGA," *J. Bacteriol.,* 173(6):2093–2098 (Mar. 1991).

Harlow, E., et al., *Antibodies: A Laboratory Manual,* Cold Springs Harbor, p. 76 (1988).

Hartnett, C., et al., "DNA Sequences Of Genes Encoding *Acinetobacter calcoaceticus* Protcatechuate 3,4–Dioxygenase: Evidence Indicating Shuffling Of Genes And Of DNA Sequences Within Genes During Their Evolutionary Divergence," *J. Bacteriology,* 172(2):956–966 (Feb. 1990).

Holmes, Eric H., "PSMA Specific Antibodies And Their Diagnostic And Therapeutic Use," *Exp. Opin. On Invest. Drugs,* 10(3):511–519 (2001).

Israeli, Ron S., et al., "Molecular Cloning of a Complementary DNA Encoding a Prostate–Specific Membrane Antigen," *Cancer Research,* 53(2):227–230 (1993).

Palm, P., et al., "Complete Nucleotide Sequence Of The Virus SSV1 Of The Archaebacterium *Sulfolobus shibatae,"* *Virology,* 185:242–250 (1991).

Ramakrishnan, V., et al., "Cloning, Sequencing And Overexpressing Of Genes For Ribosomal Proteins From *Bacillus Stearothermophilus,"* *J. Biol. Chem.,* 266(2):880–885 (1991).

Schiefer–Ullrich, H., et al., "Comparative Studies On Physiology And Taxonomy Of Obligately Purinolytic Closteridia," *Arch. Microbiol.,* 138:345–353 (1984).

Sulavik, M.C., et al., "Identification Of A Gene, rgg, Which Regulates Expression Of Glucosyltransferase And Influences the Spp Phenotype Of *Streptococcus gordonii* Challis," *J. Bacteriology,* 174(11):3577–3586 (1992); and Communication Pursuant To Article 115(2) EPC issued Aug. 30, 2004 in connection with related European Patent Application No. 94 90 0538.3.

Carter, RE, et al., "Prostate–specific membrane antigen is a hydrolase with substrate and pharmacologic characteristics of a neuropeptidase," *Proc. Natl. Acad. Sci. USA,* 93: 749–53. (1996) (Exhibit 1).

Halsted, CH, et al., "Folylpoly–γ–glutamate Carboxypeptidase from Pig Jejunum. Molecular Characterization and Relation to Glutamate Carboxypeptidase II," *J. Biol. Chem.,* 273(32): 20417–24. (1998) (Exhibit 2).

Slusher, BS, et al., "Rat brain N–acetylated alpha–linked acidic dipeptidase activity. Purification and immunologic characterization," *J. Biol. Chem.,* 265(34): 21297–301. (1990) (Exhibit 3).

Wang, TT, et al., "Intracellular pteroylpolyglutamate hydrolase from human jejunal mucosa. Isolation and characterization," *J. Biol. Chem.,* 261(29): 13551–5. (1986) (Exhibit 4).

Sharief, F.S., Lee, H., Leuderman, M.M., Lundwall, A., Deaven, L.L., Lee, C.L. and Li, S.S. (1989) Human prostatic acid phosphatase: cDNA cloning, gene mapping and protein sequence homology with lysosomal acid phosphatase. Biochem. Biophys. Res. Commun. 160: 79–86.

Wright, Jr., G.L, Feng, Q., Beckett, M.L., Lopes, D. and Gilman, S.C. (1990) Characterization of a new prostate carcinoma–associated marker: 7E11–C5. Antibody, Immunoconjugates and Radiopharmaceuticals 3: 89 (Abstract 193).

Young, R.A. and Davis, R.W. (1983) Efficient isolation of genes by using antibody probes. Proc. Natl. Acad. Sci. USA 80: 1194–1198.

U.S. Appl. No. 08/403,803, filed Mar. 17, 1995, Israeli et al.
U.S. Appl. No. 08/470,735, filed Jun. 6, 1995, Israeli et al.
U.S. Appl. No. 09/724,726, filed Nov. 28, 2000, Israeli et al.
U.S. Appl. No. 09/990,595, filed Nov. 21, 2001, Israeli et al.
U.S. Appl. No. 08/481,916, filed Jun. 7, 1995, Israeli et al.
U.S. Appl. No. 10/012,169, filed Oct. 24, 2001, Israeli et al.
U.S. Appl. No. 10/614,625, filed Jul. 2, 2003, Israeli et al.
Preliminary Amendment re Exhibit 54, filed Jul. 2, 2003, Israeli et al.
U.S. Appl. No. 08/894,583, Israeli et al.
U.S. Appl. No. 10/751,346, filed Jan. 2, 2004, Israeli et al.
Su, S.L., et al. (1995) Cancer Research, 55, 7:1441–1443 (Exhibit 1).
U.S. Appl. No. 09/357,704, filed Jul. 20, 1999, Bander.
U.S. Appl. No. 09/357,707, filed Jul. 20, 1999, Bander.
U.S. Appl. No. 09/357,708, filed Jul. 20, 1999, Bander.
U.S. Appl. No. 09/357,709, filed Jul. 20, 1999, Bander.
U.S. Appl. No. 09/357,710, filed Jul. 20, 1999, Bander.
U.S. Appl. No. 09/929,546, filed Aug. 13, 2001, Bander.
U.S. Appl. No. 09/929,665, filed Aug. 13, 2001, Bander.
U.S. Appl. No. 09/561,462, filed Apr. 28, 2000, Murphy et al.
U.S. Appl. No. 09/561,502, filed Apr. 28, 2000, Murphy et al.
U.S. Appl. No. 09/724,630, filed Nov. 28, 2000, Murphy et al.
Translation of Abstract of EP 0 173 951.
Tortora, G.J., et al., (1989) *Microbiology, An Introduction,* Benjamin/Cummings Publishing Co., 423–426, 471.
Stites, D.P., et al., (1991) *Basic and Clinical Immunology,* Appleton & Lange, 229–251.

Rose, N.R., et al., (1986) *Manual of Clinical Laboratory Immunology*, American Society for Microbiology, 89–109.

Paul, W.E. (1989) *Fundamental Immunology*, Raven Press, 628–629, 647–651.

Gately, M.K. et al., (1992) "Regulation of Human Cytololytic Lymphocyte Responses by Interleukin–12", *Cellular Immunology* 143:381–385.

Rossi, M. C. & Zetter, B.R., (1992) "Selective Stimulation of Prostatic Carcinoma Cell Proliferation by Transferrin", *PNAS* 89:6197–6201.

Sambrook, J. et al., (1989) *Molecular Cloning, A Laboratory Manual*, Cold Spring Harbor Laboratory Press, 16.1–16.81.

Schneider, C. et al., (1984) "Primary Structure of Human Transferrin Receptor Deduced from the mRNA sequence", *Nature* 311:675–678.

* cited by examiner

FIGURE 2A
FIGURE 2B
FIGURE 2C
FIGURE 2D

FIGURE 4
100.5 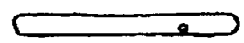 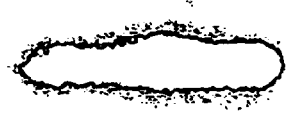
72.0 
43.0 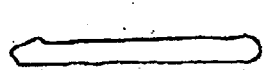
28.5 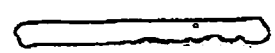

Done on sequence PMSANTIGEN.
Total number of residues is: 750.
Analysis done on the complete sequence.

```
In Helical   (H) conformation [DC = -75 CNAT ] :  264 AA => 35.2%
In Extended  (E) conformation [DC = -88 CNAT ] :  309 AA => 41.2%
In Turn      (T) conformation [DC =   0 CNAT ] :   76 AA => 10.1%
In Coil      (C) conformation [DC =   0 CNAT ] :  101 AA => 13.4%
```

Sequence shown with conformation codes.
================================================

Consecutive stretch of 5 or more residues in a given conformation are overlined.

Semi-graphical output.
==================================

Symbols used in the semi-graphical representation:

Helical conformation: X          Extended conformation: |
Turn    conformation: >          Coil     conformation: ✧

```
        10        20        30        40        50
         |         |         |         |         |
MWNLLHETDSAVATARRPRWLCAGALVLAGGFFLLGFLFGWFIKSSNEAT
XXXXXXXXXXXXXXX----->>-----------------XXXXXX✧✧✧✧✧✧>X
XXXXXXXXXXXXXX----->>--------------XXXXXX✧✧✧✧✧✧>X 60        70        80        90       100
         |         |         |         |         |
NITPKHNMKAFLDELKAENIKKFLYNFTQIPHLAGTEQNFQLAKQIQSQW
```

FIG. 14-5

```
         110        120        130        140        150
          |          |          |          |          |
XXXXXXXXXXXXXXXXX----->>-----☆☆☆☆XXXXXXXX-X☆---
XXXXXXXXXXXXXXXXXXX----->>-----☆☆☆☆XXXXXXXX-X☆---
KEFGLDSVELAHYDVLLSYPNKTHPNYISIINEDGNEIFNTSLFEPPPG 160        170        180        190        200
          |          |          |          |          |
-->>☆☆XXXXXXXXX------☆>☆☆X------>>☆☆☆>>--
-->>☆☆XXXXXXXX-------☆>☆☆X------>>☆☆☆>>--
YENVSDIVPPFSAFSPQGMPEGDLVYVWYARTEDFFKLERDMKINCSGKI
```

FIG. 14-6

```
                                                     >-☆☆☆>-------------------------------XXXXXXXXXXXXXX>>-|--
                                                     >-☆☆☆>-------------------------------XXXXXXXXXXXXXXXXX>>>-|
                                                        210       220       230       240       250
                                                         |---------|---------|---------|---------|
                                                     VIARYGKVFRGNKVKWNAQLAGAKGVILYSDPADYFAPGVKSYPDGWNLPG

------------>>-☆☆☆XXXXXXX------------>>-------------->>>->☆>
                                                     ------------>>-☆☆☆XXXXXXX-o-o-o--o-o->>--------------->>>-☆-☆☆>
                                                        260       270       280       290       300
                                                         |---------|---------|---------|---------|
                                                     GGVQRGNILNLNGAGDPLTPGYPANEYAYRRGIAEAVGLPSIPVHPIGYY

>☆----------------------------------XX-------------------
                                                     >☆----------------------------------XX-------------------
                                                        310       320       330       340       350
                                                         |---------|---------|---------|---------|
                                                     DAQKLLEKMGGSAPPDSSWRGSLKVPYNVGPGFTGNFSTQKVKMHIHSTN

XXXXXXX-->>>☆☆☆☆>-|->>-|-----------------------☆-☆XXXXXX---☆☆☆☆
                                                     XXXXXXXX->>>☆☆☆☆☆>>>-|->>-|-----------------------☆-☆XXXXXX----☆☆☆☆
                                                        360       370       380       390       400
                                                         |---------|---------|---------|---------|
                                                     EVTRIYNVIGTLRGAVEPDRYVILGGHRDSWVFGGIDPQSGAAVVHEIVR
```

FIG. 14-7

```
                                     ☆☆>---->>☆☆>☆☆XXX----XX
                                     ☆☆>----->>☆☆>☆☆XXX----XX
          410       420       430       440       450
          |         |         |         |         |
                   SFGTLKKEGWRPRRTILFASWDAEEFGLLGSTEWAEENSRLLQERGVAYI

XXX☆☆>>>>☆☆>----|----☆XXXXXX☆☆☆☆>☆☆XXXXXXXXXX--------|
XXX☆☆>>>>☆☆>----|----☆XXXXXX☆☆☆☆>☆☆XXXXXXXXXX--------|
          460       470       480       490       500
          |         |         |         |         |
                   NADSSIEGNYTLRVDCTPLMYSLVHNLTKELKSPDEGFEGKSLYESWTKK

----|--☆☆>☆----|----|----XXXXXXXXX☆☆XXXXXXXXXXXXXX>>>☆
----|--☆☆>☆----|----|----XXXXXXXXX☆☆XXXXXXXXXXXXXX>>>☆
          510       520       530       540       550
          |         |         |         |         |
                   SPSPEFSGMPRISKLGSGNDFEVFFQRLGIASGRARYTKNWETNKFSGYP

☆☆☆>----|----|---XXXXX☆☆☆>----->->>^>>^>--|--^^^>
☆☆☆>----|----|---XXXXX☆☆☆>----->->>^^>^--|--^^^>
          560       570       580       590       600
          |         |         |         |         |
```

FIG. 14-8

```
LYHSVYETYELVEKFYDPMFKYHLTVAQVRGGMVFELANSIVLPFDCRDY
------------XXXXXXXXXXXXXXXX--X--------XXXXX------->XXX
------------XXXXXXXXXXXXXXXX--X--------XXXXX------->XXX
         610           620           630           640           650

AVVLRKYADKIYSISMKHPQEMKTYSVSFDSLFSAVKNFTEIASKFSERL
XXXXXXXXXXX------X✩✩XXXXX-----------XXXXXXXXXXXXXXXXXXXX
XXXXXXXXXXX------X✩✩XXXXX-----------XXXXXXXXXXXXXXXXXXXX
         660           670           680           690           700

QDFDKSNPIVLRMTNDQLWCLERAFIDPLGLPDRPFYRHVIYAPSSHNKY
XX>>>✩✩-----------XXXXXXXXXX---->>✩✩>-----------------
XX>>>✩✩-----------XXXXXXXXXX---->>✩✩>-----------------
         710           720           730           740           750

AGESFPGIYDALFDIESKVDPSKAWGEVKRQIYVAAFTVQAAAETLSEVA
------>--XXXXXXXX✩✩✩✩XXXXXX---XXXXXXXXX--------XXXXXXXXXXXXX
-----→--XXXXXXXX✩✩✩✩XXXXXX---XXXXXXXXX--------XXXXXXXXXXXXX
```

FIG. 15B

◊◊◊◊◊◊◊◊◊◊◊◊◊◊◊◊◊◊◊◊◊◊◊◊◊◊◊◊◊◊◊◊◊◊
◊ PREDICTION OF ANTIGENIC DETERMINANTS ◊
◊◊◊◊◊◊◊◊◊◊◊◊◊◊◊◊◊◊◊◊◊◊◊◊◊◊◊◊◊◊◊◊◊◊

Done on sequence PMSANTIGEN.
Total number of residues is: 750.
Analysis done on the complete sequence.

The method used is that of Hopp and Woods.
The averaging group length is: 6 amino acids.
-> This is the value recommended by the authors <-

----------------------------------------

The three highest points of hydrophilicity are:

( 1)  Ah= 1.62 : From   63 to   68 : Asp-Glu-Leu-Lys-Ala-Glu
( 2)  Ah= 1.57 : From  132 to  137 : Asn-Glu-Asp-Gly-Asn-Glu
( 3)  Ah= 1.55 : From  482 to  487 : Lys-Ser-Pro-Asp-Glu-Gly Ah stands for: Average hydrophilicity.

Note that, on a group of control proteins, only the highest point was in 100% of the cases assigned to a known antigenic group. The second and third points gave a proportion of 33% of incorrect predictions.

FIG. 16-1

```
The best scores are:                    initn init1  opt
CHKTFER  G.gallus mRNA for transferrin receptor    203  120  321
RATTRFR  Rat transferrin receptor mRNA, 3' end.    164  164  311
HUMTFRR  Human transferrin receptor mRNA, complete cd  145  145  266

CHKTFER  G.gallus mRNA for transferrin receptor  203  120  321
51.9% identity in 717 nt overlap 1020      1030      1040      1050      1060      1070
pmsgen  TGTCCAGGCGTGGAAATATCCTAAATCTGAATGGTGCAGGAGACCCTCTCACCAGGTTA
        :::   :        ::::::    :      :::::::::  :::::::::  :
CHKTFE  TACACTTATCCCATTCGGACATGCCCACCCTTGGAACTGGAGACCCTTACACCCCAGGCTT
           990      1000      1010      1020      1030      1040

1080      1090      1100      1110      1120      1130
pmsgen  CCCAGCAAATGAATATGCTTATAGGCGTGGAATTGCAGAGGCTGTTGGTCTTCCAAGTAT
        :::   :     ::   :   :   ::  : :: :: :: :: :: :: ::  ::  ::
CHKTFE  CCCTTCGTTCAACCACACCCA---GTTTCCACCAGTTGAATCTTCAGGACTACCCCACAT
          1050      1060         1070      1080      1090      1100

1140      1150      1160      1170      1180      1190
pmsgen  TCCTGTTTCATCCAATTGGATACTATGATGCACAGAAGCTCCTAGAAAAAATGGGTGGCTC
        : ::::::: :  ::      ::   :::   :     :   :::::::   :::
CHKTFE  TGCTGTTTCAGACCATCTCTAGCAGTGCAGCCAGGCTGTTCAGCAAATGCAAAATGGATGGAGA
          1110      1120      1130      1140      1150      1160
```

FIG. 16-2

```
             1200       1210       1220       1230       1240       1250
pmsgen   AGCACCACCAGCAGCTGGAGAGGAAGTCTCAAAGTGCCCTACAATGTTGGACCTGG
          ::         : ::: :  : ::::  :::        :: ::  ::  ::: ::
CHKTFE   CACATGCTCTGA-AG--GTTGGAAAGGTGCCGATCCA---TTCCTGTAAGGT--GAC--AA
                1170       1180       1190       1200              1210

1260       1270       1280       1290       1300       1310
pmsgen   CTTTACTGGAAACTTTTCTACACAAAAAGTCAAGATGCACATCCACTCTACCAATGAAGT
         :  :  :  :::  :  : :: :: :  ::                :::       :::
CHKTFE   CAAAGCAGGAGA-----GCCAGA-TAATGGTGAAACTAGATGTGAACAATTCCATGAAAGA
              1220            1230       1240       1250       1260

1320       1330       1340       1350       1360       1370
pmsgen   GACAAGAATTTACAATGTGATAGGTACTCTCAGAGGAGCAGTGGAACCAGACAGATATGT
          :  :::     ::   ::  ::: ::  :: ::   :::: ::    :  :  :::::
CHKTFE   CAGGAAGATTCTGAACATCTTCGGTGCTATCCAGGGATTTGAAGAACCTGATCGGTATGT
              1270       1280       1290       1300       1310       1320

1380       1390       1400       1410       1420       1430
pmsgen   CATTCTGGGAGGTCACCGGGACTCATGGGTGTTTTGGTGGTATTGACCCTCAGAGTGGAGC
         :  :  :::: :: :::: :  ::::: ::::       ::  :  ::  :::: ::::
CHKTFE   TGTGATTGGAGCCCAGGAGACTCCTGGGCCCAGGAGAGTCCTAAAGCTGGCTAAAGCTGGCACTGGAAC
              1330       1340       1350       1360       1370       1380
```

FIG. 16-3

```
              1440       1450       1460       1470       1480       1490
pmsgen  AGCTGTGTTCATGAAAATTGTGAG---GAGCTTTGGAACACTGAAAAAGGAAGGGTGGAG
         ::: :   :    ::    :::      :: :::      :  :::::::  :: ::
CHKTFE  TGCTATATTGTGTTGGAACTTGCCCGTGTGATCTCAGACATAGTGAAAAACGAGGCTACAA
              1390       1400       1410       1420       1430       1440

1500       1510       1520       1530       1540       1550
pmsgen  ACCTAGAAGAACAATTTGTTTGCAAGCTGGGATGCAGAAGAATTTGGTCTCTTCTTGGTTC
         ::: ::    ::  ::   : X::::  ::::::::  :::        ::  ::  ::
CHKTFE  ACCGAGGGCGAAGCATCATCTTTGCTAGCTGGAGTGCAGGAGTGCCAGGACTACGGAGCTGTGGGTGC
              1450       1460       1470       1480       1490       1500

1560       1570       1580       1590       1600       1610
pmsgen  TACTGAGTGGGCAGAGGAGAATTCAAGACTCCTTCAAGAGCGTGGCGTGGCTGGCTTATATTAA
         ::: ::  :::  ::::: : ::X        :  ::::: ::        ::  ::  ::
CHKTFE  TACTGAAATGGCTGGAGGGGTACTCTGCCATGCTGCAAAGCTTTCACTTACATCA-
              1510       1520       1530       1540       1550       1560

1620       1630       1640       1650       1660       1670
pmsgen  TGC-TGACTCATCTATAGAAGGAAACTA-CACTCTGAGAGTTGATTGTACACCGCTGATG
         ::  ::   :::  :: ::     ::   : : ::::::::  ::::::::  :  :: ::
CHKTFE  -GCTTGGATGCTCCAGTCCTGGGAGCAAGCCATGTCAAGATTTCTGCCAGCCCCTTGCTG
              1570       1580       1590       1600       1610       1620
```

FIG. 16-4

```
             1680       1690       1700       1710       1720       1730
pmsgen  TACAGCTTGGTACACACCTAACAACCTAACAAACAAAAGAGCTGAAAAGCCCTGATGAAGGCTTTGAAGGC
        ::  ::    ::                 ::  ::   ::::  ::         ::  ::    ::
CHKTFE  TATATGCTGCTGGGGAGTATTATGAAGGGGGTGAAGAATCCAGCAGCAGTCTCAGAGAGC
             1630       1640       1650       1660       1670       1680

1740       1750       1760       1770       1780       1790
pmsgen  AAATCTCTTTATGAAAGTTGGACTAAAAAAGTCCTTCCCCAGAGTTCAGTGGCATGCCCC
        ::::  ::   ::::: ::     ::
CHKTFE  ----CTCTATAACAGACTTGGCCCAGACTGGGTAAAAGCAGTTGTTCCTCTTGGCCTGGA
                 1690       1700       1710       1720       1730
```

FIG. 16-5

```
RATTRFR   Rat transferrin receptor mRNA, 3' end.      164   164   311
          55.5% identity in 560 nt overlap 1210      1220      1230      1240      1250
pmsgen  CCACCAGATAGCCAGCTGGAGAGGAAGTCTCAAAGTGCCCTACAATGTTGGACCTGGCTT-
                ::: ::  :::        :  :  ::: :  :  ::    :   :
RATTRF  TGCAGAAAAGCTATTCAAAAACATGGAAGGAAACTGTCCTCCTAGTTGGAATATAGATTC
         610       620       630       640       650       660

1260      1270      1280      1290      1300      1310
pmsgen  -TACTGGAAACTTTTCTACACAAAAAGTCAAGATGCACATC-CACTCT-ACCAATG----
         :  ::  ::   :: ::      :: ::  :::     :::    :  :  ::::
RATTRF  CTCATGTAAGCTGGAACTTTCACAGAATCAAAATGTGAAGCTCACTGTGAACAATGTACT
         670       680       690       700       710       720
```

FIG. 16-6

```
              1320       1330       1340       1350       1360       1370
pmsgen  --AAGTGACAAGAATTTACAATGTGATAGTACTCTCAGAGGAGCAGTGGAACCAGACAG
          ::  :::::::::        :: :  ::              ::  :::::::::::
RATTRF  GAAAGAAACAAGAATACTTAACATCTTTGGCGTTATTAAAGGCTATGAGGAACCAGACCG
              730        740        750        760        770        780

1380       1390       1400       1410       1420       1430
pmsgen  ATATGTCATTCTGGGGAGTCACCGGGACTCATGGGTGTTTGGTGGTATTGACCCTCAGAG
          ::  :  :::::   ::::  ::: :  ::::   ::::  ::   ::  :::  :::
RATTRF  CTACATTGTAGTAGGAGCCCAGAGAGACGCTTGGGCCCTGGT-GTTGCGAAGTCCAGTG
              790        800        810        820        830        840

1440       1450       1460       1470       1480
pmsgen  T-GGAGCAGCTGTGTTGTTCATGAAATTGTGAGGAGCTTTGAACA-CTGA---AAAAGGAA
         :  :::  :::   ::  :: ::::::  :: ::  :: ::    ::: :::
RATTRF  TGGGAACAGGTCTT-CTGTTGAAACTTGCCCAAGTATTCTCAGATATGATTTCAAAAGAT
              850        860        870        880        890        900

1490       1500       1510       1520       1530       1540
pmsgen  GGGTGGAGACCTAGAAGAACAATTTGTTTGCAAGCTGGATGCAGAAGAATTTGGTCTT
          ::  X:::  :: :::  ::: :  :::::  :::::  ::::::  :::   :::   :
RATTRF  GGATTTAGACCAGGAGTATTATCTTTGCCAGCTGGACTGCAGGAGACTATGGAGCT
              910        920        930        940        950        960
```

FIG. 16-7

```
           1550      1560      1570      1580      1590      1600
pmsgen  CTTGGTTCTACTGAGTGGGCAGAGGAGAA---TTCAAGACTCCTTCAAGAGCGTGGCGTG
        :::::  : :::::::::  ::::: X  ::::  :  :: :: ::        ::
RATTRF  GTTGGTCCGACTGGCTGGAGGGGTACCTTTCATCTCTTTGCATCTAAAG---GCTTTC
           970       980       990      1000      1010       1020

1610      1620      1630      1640      1650      1660
pmsgen  GCTTATATTAATGCTGACTCATCTCTATAGAAGGAAACTA-CACTCTGAGAGTTGATTGTAC
        :::: :::::::: ::: ::  :  ::  :::::: ::  :  ::
RATTRF  ACTTACATTAAT-CTGGATAAAGTCGTCCTGGGTACTAGCAACTTCAAGGTTTCTGCCAG
          1030      1040       1050      1060       1070      1080

1670      1680      1690      1700      1710      1720
pmsgen  ACCGCTGATGTACAGCTTGGTACACAACCTAACAAAGAGCTGAAAAGC-CCTGATGAAG
        ::  :: :::  :  :: ::  ::: :::::      :: :::::: : ::
RATTRF  CCCCCTATTATATACACTTATGGGAAGATAATGCAGGA--CGTAAAGCATCCGA----
          1090      1100      1110      1120       1130
```

FIG. 16-8

```
              1730       1740       1750       1760       1770
pmsgen  GCTTTGAAGGCAAATCTCTTTAT-GAA------AGTTGGACTAAAAAAGTCCTTCCCAG
        :::: :: ::::: :::           : :::::: ::  :::: :
RATTRF  ----TTGATGAAAATATCTATATCGAAACAGTAATTGGATTAGCAAATTGAGGAACTTT
              1140       1150       1160       1170       1180       1190

1780       1790       1800       1810       1820       1830
pmsgen  AGTTCAGTGGCATGCCCAGGATAAGCAAATTGGGATCTGGAAATGATTTGAGGTGTTCT
RATTRF  CCTTGGACAATGCTGCATTCCCTTTTCTTGCATATTCAGGAATCCCAGCAGTTTCTTTCT
              1200       1210       1220       1230       1240       1250
```

FIG. 16-9

HUMTFRR  Human transferrin receptor mRNA, complete cd  145  145  266
54.3% identity in 464 nt overlap

```
               1230      1240      1250      1260      1270
pmsgen AGGAAGTCTCAAAGTGCCCTACAATGTGGACCCTGGCTTTAC-TGGAAACTTTCTACAC
         ::   :::       :::  :::  ::   ::   :::  ::
HUMTFR TATGGAAGGAGACTGTCCCTCTGACTGGAAAACAGACTCTACATGTAGGATGGTAACCTC
         1140      1150      1160      1170      1180      1190

1280      1290      1300      1310      1320      1330
pmsgen AAAAAGTCAAGATGCACATC-CACTCT-ACCAATG------AAGTGACAAGAATTTACAA
        :  :::::  :::   ::::   ::   :::::        :::  ::  ::   ::
HUMTFR AGAAAGCAAGAATGTGAAGCTCACTGTGAGCAATGTGCTGAAAGAGATAAAATTCTTAA
         1200      1210      1220      1230      1240      1250

1340      1350      1360      1370      1380      1390
pmsgen TGTGATAGGTACTCTCAGGAGCAGTGGAACCAGATATGTCATTCTGGGAGGTCA
       ::   ::   :::     ::::::::         :::::  ::      ::
HUMTFR CATCTTTGGAGTTATTAAAGGCTTTGGTGGTATTGACCCTCAGAGT-GGAGCAGCTGTTGTTCATG
         1260      1270      1280      1290      1300      1310

1400      1410      1420      1430      1440      1450
pmsgen CCGGGGACTCATGGGTGTGTTTGGTGGTATTGACCCTCAGAGT-GGAGCAGCTGTTGTTCATG
        :  ::::::      :::::::       ::  :::    :::::  :
HUMTFR GAGAGATGCATGGGCCCTGAGCTGCAAAATC-CGGTGTAGGCACAGCTCTCCTATTGA
         1320      1330      1340      1350      1360      1370
```

FIG. 16-10

```
              1460       1470       1480       1490       1500
pmsgen   AAATTG---TGAGGAGCTTTGGAACACTGAAAAAGGAAGGGTGGAGACCTAGAAGAACAA
          ::  :::      ::  ::  :     ::: :: X:::     :: :: :::: ::
HUMTFR   AACTTGCCCAGATGTTCTCAGATATGGTCTTAAAGATGGGTTTCAGCCCCAGCAGAAGCA
              1380       1390       1400       1410       1420       1430

1510       1520       1530       1540       1550       1560
pmsgen   TTTTGTTTTGCAAGCTGGGATGCAGAAGAATTTGGTCTTCTTGGTTCTCTACTGAGTGGGCAG
          ::  :  ::::::  ::  :::   :::  :::  :::::        ::::: :  :::::  :::  ::
HUMTFR   TTATCTTTGCCAGTTGCCAGTGGAGTGCTGGAGACTTTGGAGTCGGTTGGTGCCACTGAATGGCTAG
              1440       1450       1460       1470       1480       1490

1570       1580       1590       1600       1610       1620
pmsgen   A-GGAGAATTCAAGACTCCCTTCAAGAGCGTGGCGTGGCTTATATTAATGCTGACTCATCT
          :  :::: ::   :  : ::: ::   ::   :    :  ::::::::::X   ::    ::
HUMTFR   AGGGATACCTTTCGTC-CCTGCATTTAAAGGCTTTCACTTATATTAATCTGGATAAAGCG
              1500       1510       1520       1530       1540       1550

1630       1640       1650       1660       1670       1680
pmsgen   ATAGAAGGAAACTACACTCTGAGAGTTGATTGTACACCGCTGATGTACA-GCTTGGT-AC
          :                  ::  ::  :  :::   :  :   ::  :: ::::  ::::    ::
HUMTFR   GTTCTTGGTACCAGCAACTTCAAGGTTTCTGCCAGCCCCACTGTTGTATACGCTTATTGAG
              1560       1570       1580       1590       1600       1610
```

FIG. 16-11

```
              1690      1700      1710      1720      1730      1740
pmsgen ACAACCTAACAAAACAAAAGAGCTGAAAAGCCCTGATGAAGGCTTTGAAGGCAAATCTCTTTATG
          ° °°°       °°  °°°°°
HUMTFR AAAACAAATGCAAAATGTGAAGCATCCGGTTACTGGGCAATTCTATATCAGGACAGCAAC
       1620      1630      1640      1650      1660      1670
```

FIGURE 23

| CELL LINE/TYPE | 11p11.2-13 REGION | METASTATIC | PSM RNA DETECTED | PSM DNA DETECTED |
|---|---|---|---|---|
| LNCap | | | ++ | ND |
| HUMAN PROSTATE | | | ++ | ND |
| A9 (FIBROSARCOMA) | NO | NO | - | - |
| A9(11) (A9+HUM. 11) | YES | NO | - | REPEAT |
| AT6.1 (RAT PROSTATE) | NO | YES | - | - |
| AT6.1-11-c11 | YES | NO | + | ++ |
| AT6.1-11-c12 | NO | YES | - | - |
| R1564 (RAT MAMMARY) | NO | YES | - | - |
| R1564-11-c14 | YES | YES | - | + |
| R1564-11-c15 | YES | YES | - | REPEAT |
| R1564-11-c16 | YES | YES | - | ND |
| R1564-11-c12 | YES | YES | ND | + |

FIGURE 30

| Patient | Stage | Treatment | PSA | PAP | PSA-PCR | PSM-PCR |
|---|---|---|---|---|---|---|
| 1 | T2NxMo | None | 8.9 | 0.7 | − | + |
| 2 | T2NoMo | RRP 7/93 | 6.1 | − | − | + |
| 3 | T2CNoMo | PLND 5/93 | 4.5 | 0.1 | − | + |
| 4 | T2BNoMo | RRP 3/92 | NMA | 0.4 | − | + |
| 5 | T3NxMo | Proscar + Flutamide | 51.3 | 1.0 | − | + |
| 6 | Recur T3 | I-125 1986 | 54.7 | 1.4 | − | + |
| 7 | T3ANoMo | RRP 10/92 | NMA | 0.3 | − | + |
| 8 | T3NxMo | XRT 1987 | 7.5 | 0.1 | − | − |
| 9 | T3NxMo | Proscar + Flutamide | 35.4 | 0.7 | − | − |
| 10 | D2 | S/P XRT Flutamide +Emcyt | 311 | 4.5 | + | + |
| 11 | D2 | RRP 4/91 Lupron 10/92 Velban + Emcyt 12/92 | 1534 | 1.4 | + | + |
| 12 | T2NoMo | RRP 8/91 | NMA | 0.5 | − | + |
| 13 | T3NoMo | RRP 1/88 Lupron + Flutamide 5/92 | 0.1 | 0.3 | − | − |
| 14 | D1 | PLND 1989 XRT 1989 | 1.6 | 0.4 | − | − |
| 15 | D1 | Proscar + Flutamide | 20.8 | 0.5 | − | − |
| 16 | T2CNoMo | RRP 4/92 | 0.1 | 0.3 | − | − |

SEQUENCE LISTING

<160> NUMBER OF SEQ ID NOS: 38

<210> SEQ ID NO 1
<211> LENGTH: 2653
<212> TYPE: DNA
<213> ORGANISM: Human

<400> SEQUENCE: 1

```
ctcaaaaggg gccggatttc cttctcctgg aggcagatgt tgcctctctc tctcgctcgg      60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
cccggctctg ctcgcgccga gatgtggaat ctccttcacg aaaccgactc ggctgtggcc    300
accgcgcgcc gcccgcgctg gctgtgcgct ggggcgctgg tgctggcggg tggcttcttt    360
ctcctcggct tcctcttcgg gtggtttata aaatcctcca atgaagctac taacattact    420
ccaaagcata atatgaaagc atttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac ctcctccagg atatgaaaat    720
gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga aagttttcag aggaaataag    900
gttaaaaatg cccagctggc aggggccaaa ggagtcattc tctactccga ccctgctgac    960
tactttgctc ctgggtgaa gtcctatcca gatggttgga tcttcctgg aggtggtgtc   1020 cagcgtggaa atatcctaaa tctgaatggt gcaggagacc ctctcacacc aggttaccca   1080
gcaaatgaat atgcttatag gcgtggaatt gcagaggctg ttggtcttcc aagtattcct   1140
```

-continued

```
gttcatccaa ttggatacta tgatgcacag aagctcctag aaaaaatggg tggctcagca    1200
ccaccagata gcagctggag aggaagtctc aaagtgccct acaatgttgg acctggcttt    1260
actggaaact tttctacaca aaaagtcaag atgcacatcc actctaccaa tgaagtgaca    1320
agaatttaca atgtgatagg tactctcaga ggagcagtgg aaccagacag atatgtcatt    1380 ctggaggtc accgggactc atgggtgttt ggtggtattg accctcagag tggagcagct     1440
gttgttcatg aaattgtgag gagctttgga acactgaaaa aggaagggtg gagacctaga    1500
agaacaattt tgtttgcaag ctgggatgca aagaatttg gtcttcttgg ttctactgag     1560
tgggcagagg agaattcaag actccttcaa gagcgtggcg tggcttatat taatgctgac    1620
tcatctatag aaggaaacta cactctgaga gttgattgta caccgctgat gtacagcttg    1680
gtacacaacc taacaaaaga gctgaaaagc cctgatgaag ctttgaagg caaatctctt     1740 tatgaaagtt ggactaaaaa aagtccttcc ccagagttca gtggcatgcc caggataagc    1800
aaattgggat ctgaaaatga ttttgaggtg ttcttccaac gacttggaat tgcttcaggc    1860
agagcacggt atactaaaaa ttgggaaaca aacaaattca gcggctatcc actgtatcac    1920
agtgtctatg aaacatatga gttggtggaa aagttttatg atccaatgtt taaatatcac    1980
ctcactgtgg cccaggttcg aggagggatg gtgtttgagc tagccaattc catagtgctc    2040 cctttgatt gtcgagatta tgctgtagtt ttaagaaagt atgctgacaa aatctacagt    2100
atttctatga acatccaca ggaaatgaag acatacagtg tatcatttga ttcacttttt     2160
tctgcagtaa agaattttac agaaattgct tccaagttca gtgagagact ccaggacttt    2220
gacaaaagca acccaatagt attaagaatg atgaatgatc aactcatgtt tctggaaaga    2280
gcatttattg atccattagg gttaccagac aggccttttt ataggcatgt catctatgct    2340
ccaagcagcc acaacaagta tgcaggggag tcattcccag gaatttatga tgctctgttt    2400
gatattgaaa gcaaagtgga cccttccaag gcctggggag aagtgaagag acagatttat    2460
gttgcagcct tcacagtgca ggcagctgca gagactttga gtgaagtagc ctaagaggat    2520
tctttagaga atccgtattg aatttgtgtg gtatgtcact cagaaagaat cgtaatgggt    2580
atattgataa atttttaaaat tggtatattt gaaataaagt tgaatattat atataaaaaa    2640
aaaaaaaaaa aaa                                                       2653
```

<210> SEQ ID NO 2
<211> LENGTH: 750
<212> TYPE: PRT
<213> ORGANISM: Human

<400> SEQUENCE: 2

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95
```

-continued

```
Gln Ser Gln Trp Lys Glu Phe Gly Leu Asp Ser Val Glu Leu Ala His
            100                 105                 110
Tyr Asp Val Leu Leu Ser Tyr Pro Asn Lys Thr His Pro Asn Tyr Ile
            115                 120                 125
Ser Ile Ile Asn Glu Asp Gly Asn Glu Ile Phe Asn Thr Ser Leu Phe
        130                 135                 140
Glu Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
Lys Ile Asn Cys Ser Gly Lys Ile Val Ile Ala Arg Tyr Gly Lys Val
            195                 200                 205
Phe Arg Gly Asn Lys Val Lys Asn Ala Gln Leu Ala Gly Ala Lys Gly
        210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
        275                 280                 285
Leu Pro Ser Ile Pro Val His Pro Ile Gly Tyr Tyr Asp Ala Gln Lys
        290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
        370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
            435                 440                 445
Tyr Ile Asn Ala Asp Ser Ser Ile Glu Gly Asn Tyr Thr Leu Arg Val
        450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
            500                 505                 510
Ser Lys Leu Gly Ser Gly Asn Asp Phe Glu Val Phe Phe Gln Arg Leu
```

-continued

```
               515                 520                 525
Lys Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

<210> SEQ ID NO 3
<211> LENGTH: 8
<212> TYPE: PRT
<213> ORGANISM: Human

<400> SEQUENCE: 3

```
Ser Leu Tyr Glu Ser Trp Thr Lys
1               5
```

<210> SEQ ID NO 4
<211> LENGTH: 15
<212> TYPE: PRT
<213> ORGANISM: Human
<220> FEATURE:
<221> NAME/KEY: MISC_FEATURE
<222> LOCATION: (6)..(7)
<223> OTHER INFORMATION: Xaa=unknown

<400> SEQUENCE: 4

```
Ser Tyr Pro Asp Gly Xaa Xaa Leu Pro Gly Gly Val Gln Arg
1               5                   10                  15
```

<210> SEQ ID NO 5
<211> LENGTH: 7
<212> TYPE: PRT
<213> ORGANISM: Human

<400> SEQUENCE: 5

Phe Tyr Asp Pro Met Phe Lys

```
1               5

<210> SEQ ID NO 6
<211> LENGTH: 9
<212> TYPE: PRT
<213> ORGANISM: Human

<400> SEQUENCE: 6

Ile Tyr Asn Val Ile Gly Thr Leu Lys
1               5

<210> SEQ ID NO 7
<211> LENGTH: 22
<212> TYPE: PRT
<213> ORGANISM: Human
<220> FEATURE:
<221> NAME/KEY: MISC_FEATURE
<222> LOCATION: (4)..(5)
<223> OTHER INFORMATION: Xaa=unknown

<400> SEQUENCE: 7

Phe Leu Tyr Xaa Xaa Thr Gln Ile Pro His Leu Ala Gly Thr Glu Gln
1               5                   10                  15

Asn Phe Gln Leu Ala Lys
            20

<210> SEQ ID NO 8
<211> LENGTH: 17
<212> TYPE: PRT
<213> ORGANISM: Human

<400> SEQUENCE: 8

Gly Val Ile Leu Tyr Ser Asp Pro Ala Asp Tyr Phe Ala Pro Asp Val
1               5                   10                  15

Lys

<210> SEQ ID NO 9
<211> LENGTH: 17
<212> TYPE: PRT
<213> ORGANISM: Human

<400> SEQUENCE: 9

Pro Val Ile Leu Tyr Ser Asp Pro Ala Asp Tyr Phe Ala Pro Gly Val
1               5                   10                  15

Lys

<210> SEQ ID NO 10
<211> LENGTH: 15
<212> TYPE: PRT
<213> ORGANISM: Human

<400> SEQUENCE: 10

Ala Phe Ile Asp Pro Leu Gly Leu Pro Asp Arg Pro Phe Tyr Arg
1               5                   10                  15

<210> SEQ ID NO 11
<211> LENGTH: 19
<212> TYPE: PRT
<213> ORGANISM: Human

<400> SEQUENCE: 11

Tyr Ala Gly Glu Ser Phe Pro Gly Ile Tyr Asp Ala Leu Phe Asp Ile
1               5                   10                  15
```

Glu Ser Lys

<210> SEQ ID NO 12
<211> LENGTH: 22
<212> TYPE: PRT
<213> ORGANISM: Human
<220> FEATURE:
<221> NAME/KEY: MISC_FEATURE
<222> LOCATION: (14)..(15)
<223> OTHER INFORMATION: Xaa=unknown

<400> SEQUENCE: 12

Thr Ile Leu Phe Ala Ser Trp Asp Ala Glu Glu Phe Gly Xaa Xaa Gly
1               5                   10                  15

Ser Thr Glu Glu Ala Glu
            20

<210> SEQ ID NO 13
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n=any nucleotide

<400> SEQUENCE: 13
ttytaygayc cnatgtt                                              17

<210> SEQ ID NO 14
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n=any nucleotide

<400> SEQUENCE: 14
aacatnggrt crtaraa                                              17

<210> SEQ ID NO 15
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n=any nucleotide

<400> SEQUENCE: 15
athtayaayg tnathgg                                              17

<210> SEQ ID NO 16
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n=any nucleotide

```
<400> SEQUENCE: 16
ccdatnacrt trtadat                                                17

<210> SEQ ID NO 17
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n=any nucleotide
<220> FEATURE:
<221> NAME/KEY: misc_feature
<222> LOCATION: (6)..(6)
<223> OTHER INFORMATION: n=any nucleotide

<400> SEQUENCE: 17
ccngcngayt ayttygc                                                17

<210> SEQ ID NO 18
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n=any nucleotide
<220> FEATURE:
<221> NAME/KEY: misc_feature
<222> LOCATION: (15)..(15)
<223> OTHER INFORMATION: n=any nucleotide

<400> SEQUENCE: 18
gcraartart ncgcngg                                                17

<210> SEQ ID NO 19
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n=any nucleotide

<400> SEQUENCE: 19
acngarcara ayttycarct                                             20

<210> SEQ ID NO 20
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n=any nucleotide

<400> SEQUENCE: 20
agytgraart tytgytcngt                                             20

<210> SEQ ID NO 21
```

```
<211> LENGTH: 17
<212> TYPE: DNA
<213> ORGANISM: artificial sequence
<220> FEATURE:
<223> OTHER INFORMATION: primer

<400> SEQUENCE: 21
garcaraayt tycarct                                                17

<210> SEQ ID NO 22
<211> LENGTH: 17
<212> TYPE: DNA
<213> ORGANISM: artificial sequence
<220> FEATURE:
<223> OTHER INFORMATION: primer

<400> SEQUENCE: 22
agytgraart tytgytc                                                17

<210> SEQ ID NO 23
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n=any nucleotide

<400> SEQUENCE: 23
tgggaygcng argarttygg                                             20

<210> SEQ ID NO 24
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n=any nucleotide

<400> SEQUENCE: 24
ccraaytcyt cngcrtccca                                             20

<210> SEQ ID NO 25
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n=any nucleotide

<400> SEQUENCE: 25
tgggaygcng argartt                                                17

<210> SEQ ID NO 26
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
```

```
<222> LOCATION: (9)..(9)
<223> OTHER INFORMATION: n=any nucleotide

<400> SEQUENCE: 26
aaytcytcng crtccca                                                      17

<210> SEQ ID NO 27
<211> LENGTH: 780
<212> TYPE: DNA
<213> ORGANISM: chicken
<220> FEATURE:
<221> NAME/KEY: misc_feature
<222> LOCATION: (82)..(84)
<223> OTHER INFORMATION: n=any nucleotide
<220> FEATURE:
<221> NAME/KEY: misc_feature
<222> LOCATION: (193)..(193)
<223> OTHER INFORMATION: n=any nucleotide
<220> FEATURE:
<221> NAME/KEY: misc_feature
<222> LOCATION: (196)..(197)
<223> OTHER INFORMATION: n=any nucleotide
<220> FEATURE:
<221> NAME/KEY: misc_feature
<222> LOCATION: (217)..(219)
<223> OTHER INFORMATION: n=any nucleotide
<220> FEATURE:
<221> NAME/KEY: misc_feature
<222> LOCATION: (232)..(233)
<223> OTHER INFORMATION: n=any nucleotide
<220> FEATURE:
<221> NAME/KEY: misc_feature
<222> LOCATION: (237)..(238)
<223> OTHER INFORMATION: n=any nucleotide
<220> FEATURE:
<221> NAME/KEY: misc_feature
<222> LOCATION: (253)..(256)
<223> OTHER INFORMATION: n=any nucleotide
<220> FEATURE:
<221> NAME/KEY: misc_feature
<222> LOCATION: (263)..(263)
<223> OTHER INFORMATION: n=any nucleotide
<220> FEATURE:
<221> NAME/KEY: misc_feature
<222> LOCATION: (600)..(601)
<223> OTHER INFORMATION: n=any nucleotide
<220> FEATURE:
<221> NAME/KEY: misc_feature
<222> LOCATION: (721)..(724)
<223> OTHER INFORMATION: n=any nucleotide

<400> SEQUENCE: 27
tacacttatc ccattcggac atgcccacct tggaactgga gacccttaca ccccaggctt      60
cccttcgttc aaccacaccc anngtttcc accagttgaa tcttcaggac taccccacat     120
tgctgttcag accatctcta gcagtgcagc agccaggctg ttcagcaaaa tggatggaga    180
cacatgctct ganagnngtt ggaaaggtgc gatccannnt tcctgtaagg tnngacnnaa    240
caaagcagga gannnngcca gantaatggt gaaactagat gtgaacaatt ccatgaaaga   300
caggaagatt ctgaacatct tcggtgctat ccagggattt gaagaacctg atcggtatgt   360
tgtgattgga gcccagagag actcctgggg cccaggagtg gctaaagctg gcactggaac   420
tgctatattg ttggaacttg cccgtgtgat ctcagacata gtgaaaaacg agggctacaa    480
accgaggcga agcatcatct ttgctagctg gagtgcagga gactacggag ctgtgggtgc   540
tactgaatgg ctggagggt actctgccat gctgcatgcc aaagctttca cttacatcan    600
ngcttggatg ctccagtcct gggagcaagc catgtcaaga tttctgccag ccccttgctg   660
tatatgctgc tggggagtat tatgaagggg gtgaagaatc cagcagcagt ctcagagagc   720
```

```
nnnnctctat aacagacttg gcccagactg ggtaaaagca gttgttcctc ttggcctgga    780
```

<210> SEQ ID NO 28
<211> LENGTH: 660
<212> TYPE: DNA
<213> ORGANISM: rat
<220> FEATURE:
<221> NAME/KEY: misc_feature
<222> LOCATION: (284)..(284)
<223> OTHER INFORMATION: n=any nucleotide
<220> FEATURE:
<221> NAME/KEY: misc_feature
<222> LOCATION: (224)..(224)
<223> OTHER INFORMATION: n=any nucleotide
<220> FEATURE:
<221> NAME/KEY: misc_feature
<222> LOCATION: (255)..(255)
<223> OTHER INFORMATION: n=any nucleotide
<220> FEATURE:
<221> NAME/KEY: misc_feature
<222> LOCATION: (412)..(414)
<223> OTHER INFORMATION: n=any nucleotide
<220> FEATURE:
<221> NAME/KEY: misc_feature
<222> LOCATION: (433)..(433)
<223> OTHER INFORMATION: n=any nucleotide
<220> FEATURE:
<221> NAME/KEY: misc_feature
<222> LOCATION: (520)..(521)
<223> OTHER INFORMATION: n=any nucleotide
<220> FEATURE:
<221> NAME/KEY: misc_feature
<222> LOCATION: (536)..(543)
<223> OTHER INFORMATION: n=any nucleotide

<400> SEQUENCE: 28

```
tgcagaaaag ctattcaaaa acatggaagg aaactgtcct cctagttgga atatagattc    60
ctcatgtaag ctggaacttt cacagaatca aaatgtgaag ctcactgtga acaatgtact   120
gaaagaaaca agaatactta acatctttgg cgttattaaa ggctatgagg aaccagaccg   180
ctacattgta gtaggagccc agagagacgc ttggggccct ggtngttgcg aagtccagtg   240
tgggaacagg tcttnctgtt gaaacttgcc caagtattct cagatatgat ttcaaaagat   300
ggatttagac ccagcaggag tattatcttt gccagctgga ctgcaggaga ctatggagct   360
gttggtccga ctgagtggct ggaggggtac ctttcatctt tgcatctaaa gnnngctttc   420
acttacatta atnctggata aagtcgtcct gggtactagc aacttcaagg tttctgccag   480 cccccctatta tatacactta tggggaagat aatgcaggan ncgtaaagca tccgannnnn   540
nnnttgatgg aaaatatcta tatcgaaaca gtaattggat tagcaaaatt gaggaacttt   600
ccttggacaa tgctgcattc ccttttcttg catattcagg aatcccagca gtttctttct   660
```

<210> SEQ ID NO 29
<211> LENGTH: 540
<212> TYPE: DNA
<213> ORGANISM: human
<220> FEATURE:
<221> NAME/KEY: misc_feature
<222> LOCATION: (214)..(214)
<223> OTHER INFORMATION: n=any nucleotide
<220> FEATURE:
<221> NAME/KEY: misc_feature
<222> LOCATION: (377)..(377)
<223> OTHER INFORMATION: n=any nucleotide

<400> SEQUENCE: 29

```
tatggaagga gactgtccct ctgactggaa aacagactct acatgtagga tggtaacctc    60
agaaagcaag aatgtgaagc tcactgtgag caatgtgctg aaagagataa aaattcttaa   120
```

-continued

```
catctttgga gttattaaag gctttgtaga accagatcac tatgttgtag ttggggccca    180
gagagatgca tggggccctg gagctgcaaa atcncggtgt aggcacagct ctcctattga    240
aacttgccca gatgttctca gatatggtct taaaagatgg gtttcagccc agcagaagca    300
ttatctttgc cagttggagt gctggagact ttggatcggt tggtgccact gaatggctag    360
agggatacct ttcgtcncct gcatttaaag gctttcactt atattaatct ggataaagcg    420
gttcttggta ccagcaactt caaggtttct gccagcccac tgttgtatac gcttattgag    480
aaaacaatgc aaaatgtgaa gcatccggtt actgggcaat ttctatatca ggacagcaac    540
```

<210> SEQ ID NO 30
<211> LENGTH: 27
<212> TYPE: DNA
<213> ORGANISM: artificial sequence
<220> FEATURE:
<223> OTHER INFORMATION: primer

<400> SEQUENCE: 30
acggagcaaa actttcagct tgcaaag    27

<210> SEQ ID NO 31
<211> LENGTH: 9
<212> TYPE: PRT
<213> ORGANISM: artificial sequence
<220> FEATURE:
<223> OTHER INFORMATION: primer

<400> SEQUENCE: 31

Thr Glu Gln Asn Phe Gln Leu Ala Lys
1               5

<210> SEQ ID NO 32
<211> LENGTH: 36
<212> TYPE: DNA
<213> ORGANISM: artificial sequence
<220> FEATURE:
<223> OTHER INFORMATION: primer

<400> SEQUENCE: 32
ctcttcggca tcccagcttg caaacaaaat tgttct    36

<210> SEQ ID NO 33
<211> LENGTH: 36
<212> TYPE: DNA
<213> ORGANISM: artificial sequence
<220> FEATURE:
<223> OTHER INFORMATION: primer

<400> SEQUENCE: 33
agaacaattt tgtttgcaag ctgggatgcc aaggag    36

<210> SEQ ID NO 34
<211> LENGTH: 12
<212> TYPE: PRT
<213> ORGANISM: artificial sequence
<220> FEATURE:
<223> OTHER INFORMATION: primer

<400> SEQUENCE: 34

Arg Thr Ile Leu Phe Ala Ser Trp Asp Ala Glu Glu
1               5                   10

<210> SEQ ID NO 35

-continued

```
<211> LENGTH: 6
<212> TYPE: PRT
<213> ORGANISM: human

<400> SEQUENCE: 35

Asp Glu Leu Lys Ala Glu
1               5

<210> SEQ ID NO 36
<211> LENGTH: 6
<212> TYPE: PRT
<213> ORGANISM: human

<400> SEQUENCE: 36

Asn Glu Asp Gly Asn Glu
1               5

<210> SEQ ID NO 37
<211> LENGTH: 6
<212> TYPE: PRT
<213> ORGANISM: human

<400> SEQUENCE: 37

Lys Ser Pro Asp Glu Gly
1               5

<210> SEQ ID NO 38
<211> LENGTH: 17
<212> TYPE: PRT
<213> ORGANISM: human

<400> SEQUENCE: 38

Ala Gly Ala Leu Val Leu Ala Gly Gly Phe Phe Leu Leu Gly Phe Leu
1               5                   10                  15

Phe
```

PROSTATE-SPECIFIC MEMBRANE ANTIGEN

This application is a continuation application of U.S. Ser. No. 08/403,803, filed Mar. 17, 1995, and a continuation of PCT International Application No. PCT/US93/10624, filed Nov. 5, 1993; which is a continuation-in-part of U.S. Ser. No. 07/973,337, filed Nov. 5, 1992, now abandoned, the contents of which are hereby incorporated by reference.

This invention disclosed herein was made in part with Government support under NIH Grants No. DK47650 and CA58192 from the Department of Health and Human Services. Accordingly, the U.S. Government has certain rights in this invention.

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citation for these references may be found at the end of each series of experiments.

Prostate cancer is among the most significant medical problems in the United States, as the disease is now the most common malignancy diagnosed in American males. In 1992 there were over 132,000 new cases of prostate cancer detected with over 36,000 deaths attributable to the disease, representing a 17.3% increase over 4 years (2). Five year survival rates for patients with prostate cancer range from 88% for those with localized disease to 29% for those with metastatic disease. The rapid increase in the number of cases appears to result in part from an increase in disease awareness as well as the widespread use of clinical markers such as the secreted proteins prostate-specific antigen (PSA) and prostatic acid phosphatase (PAP) (37).

The prostate gland is a site of significant pathology affected by conditions such as benign growth (BPH), neoplasia (prostatic cancer) and infection (prostatitis). Prostate cancer represents the second leading cause of death from cancer in man (1). However prostatic cancer is the leading site for cancer development in men. The difference between these two facts relates to prostatic cancer occurring with increasing frequency as men age, especially in the ages beyond 60 at a time when death from other factors often intervenes. Also, the spectrum of biologic aggressiveness of prostatic cancer is great, so that in some men following detection the tumor remains a latent histologic tumor and does not become clinically significant, whereas in other it progresses rapidly, metastasizes and kills the man in a relatively short 2–5 year period (1, 3).

In prostate cancer cells, two specific proteins that are made in very high concentrations are prostatic acid phosphatase (PAP) and prostate specific antigen (PSA) (4, 5, 6). These proteins have been characterized and have been used to follow response to therapy. With the development of cancer, the normal architecture of the gland becomes altered, including loss of the normal duct structure for the removal of secretions and thus the secretions reach the serum. Indeed measurement of serum PSA is suggested as a potential screening method for prostatic cancer. Indeed, the relative amount of PSA and/or PAP in the cancer reduces as compared to normal or benign tissue.

PAP was one of the earliest serum markers for detecting metastatic spread (4). PAP hydrolyses tyrosine phosphate and has a broad substrate specificity. Tyrosine phosphorylation is often increased with oncogenic transformation. It has been hypothesized that during neoplastic transformation there is less phosphatase activity available to inactivate proteins that are activated by phosphorylation on tyrosine residues. In some instances, insertion of phosphatases that have tyrosine phosphatase activity has reversed the malignant phenotype.

PSA is a protease and it is not readily appreciated how loss of its activity correlates with cancer development (5, 6). The proteolytic activity of PSA is inhibited by zinc. Zinc concentrations are high in the normal prostate and reduced in prostatic cancer. Possibly the loss of zinc allows for increased proteolytic activity by PSA. As proteases are involved in metastasis and some proteases stimulate mitotic activity, the potentially increased activity of PSA could be hypothesized to play a role in the tumors metastases and spread (7).

Both PSA and PAP are found in prostatic secretions. Both appear to be dependent on the presence of androgens for their production and are substantially reduced following androgen deprivation.

Prostate-specific membrane antigen (PSM) which appears to be localized to the prostatic membrane has been identified. This antigen was identified as the result of generating monoclonal antibodies to a prostatic cancer cell, LNCaP (8).

Dr. Horoszewicz established a cell line designated LNCaP from the lymph node of a hormone refractory, heavily pretreated patient (9). This line was found to have an aneuploid human male karyotype. It maintained prostatic differentiation functionality in that it produced both PSA and PAP. It possessed an androgen receptor of high affinity and specificity. Mice were immunized with LNCaP cells and hybridomas were derived from sensitized animals. A monoclonal antibody was derived and was designated 7E11-C5 (8). The antibody staining was consistent with a membrane location and isolated fractions of LNCaP cell membranes exhibited a strongly positive reaction with immunoblotting and ELISA techniques. This antibody did not inhibit or enhance the growth of LNCaP cells in vitro or in vivo. The antibody to this antigen was remarkably specific to prostatic epithelial cells as no reactivity was observed in any other component immunohistochemical staining of cancerous epithelial cells was more intense than that of normal or benign epithelial cells.

Dr. Horoszewicz also reported detection of immunoreactive material using 7E11-C5 in serum of prostatic cancer patients (8). The immunoreactivity was detectable in nearly 60% of patients with stage D-2 disease and in a slightly lower percentage of patients with earlier stage disease, but the numbers of patients in the latter group are small. Patients with benign prostatic hyperplasia (BPH) were negative. Patients with no apparent disease were negative, but 50–60% of patients in remission yet with active stable disease or with progression demonstrated positive serum reactivity. Patients with non prostatic tumors did not show immunoreactivity with 7E11-C5.

The 7E11-C5 monoclonal antibody is currently in clinical trials. The aldehyde groups of the antibody were oxidized and the linker-chelator glycol-tyrosyl-(n, ϵ-diethylenetriamine-pentacetic acid)-lysine (GYK-DTPA) was coupled to the reactive aldehydes of the heavy chain (10). The resulting antibody was designated CYT-356. Immunohistochemical staining patterns were similar except that the CYT-356 modified antibody stained skeletal muscle. The comparison of CYT-356 with 7E11-C5 monoclonal antibody suggested both had binding to type 2 muscle fibers.

The reason for the discrepancy with the earlier study, which reported skeletal muscle to be negative, was suggested to be due to differences in tissue fixation techniques. Still, the most intense and definite reaction was observed with prostatic epithelial cells, especially cancerous cells. Reactivity with mouse skeletal muscle was detected with immunohistochemistry but not in imaging studies. The Indium[111]-labeled antibody localized to LNCaP tumors grown in nude mice with an uptake of nearly 30% of the injected dose per gram tumor at four days. In-vivo, no selective retention of the antibody was observed in antigen negative tumors such as PC-3 and DU-145, or by skeletal muscle. Very little was known about the PSM antigen. An effort at purification and characterization has been described at meetings by Dr. George Wright and colleagues (11, 12). These investigators have shown that following electrophoresis on acrylamide gels and Western blotting, the PSM antigen maintains a molecular weight of 100 kilodaltons (kd). Chemical and enzymatic treatment showed that both the peptide and carbohydrate moieties of the PSM antigen are required for recognition by the 7E11-C5 monoclonal antibody. Competitive binding studies with specific lectins suggested that galNAc is the dominant carbohydrate of the antigenic epitope.

The 100 kd glycoprotein unique to prostate cells and tissues was purified and characterized. The protein was digested proteolytically with trypsin and nine peptide fragments were sequenced. Using the technique of degenerate PCR (polymerase chain reaction), the full-length 2.65 kilobase (kb) cDNA coding for this antigen was cloned. Preliminary results have revealed that this antigen is highly expressed in prostate cancer tissues, including bone and lymph node metastases (13). The entire DNA sequence for the cDNA as well as the predicted amino acid sequence for the antigen was determined. Further characterization of the PSM antigen is presently underway in the applicants' laboratory including: analysis of PSM gene expression in a wide variety of tissues, transfection of the PSM gene into cells not expressing the antigen, chromosome localization of the PSM gene, cloning of the genomic PSM gene with analysis of the PSM promoter and generation of polyclonal and monoclonal antibodies against highly antigenic peptide domains of the PSM antigen, and identification of any endogenous PSM binding molecules (ligands).

Currently, LNCaP cells provide the best in-vitro model system to study human prostate cancer, since they produce all three prostatic bio-markers; PSA, PAP and PSM. The cells possess an aneuploid male karyotype with a Y chromosome, express a high affinity androgen receptor, and are hormonally responsive to both testosterone and DHT. Because PSM appears to be a transmembrane glycoprotein, it is considered an attractive target for both antibody-directed imaging and targeting of prostatic tumor deposits (38). We have demonstrated expression of PSM protein in LNCaP cell membranes and in PC-3 cells transfected with PSM cDNA and also the characterization of PSM mRNA expression in human tissues, and in response to steroid hormones.

BRIEF DESCRIPTION OF FIGURES

FIG. 2A–D: Upper two photos show LNCaP cytospins staining positively for PSM antigen. Lower left in DU-145 and lower right is PC-3 cytospin, both negative for PSM antigen expression.

FIG. 4: 100 kD PSM antigen following immunoprecipitation of [35]S-Methionine labelled LNCaP cells with Cyt-356 antibody.

FIG. 14:1-8 Secondary structure of PSM antigen. Panels 14-4 to 14-8 (SEQ ID NO: 2)

FIG. 16:1-11 Homology of PSM antigen nucleic acid sequence (SEQ ID NO:1) with chicken (SEQ ID NO:27), rat (SEQ ID NO:28) and human (SEQ ID NO:29) transferrin receptor nucleic acid sequences.

FIG. 23: Data illustrating results of PSM DNA and RNA presence in transfect Dunning cell lines employing Southern and Northern blotting techniques FIG. 24:A–B FIG. A indicates the power of cytokine transfected cells to teach unmodified cells. Administration was directed to the parental flank or prostate cells. The results indicate the microenvironment considerations.

FIG. B indicates actual potency at a particular site. The tumor was implanted in prostate cells and treated with immune cells at two different sites.

Figure 25A:
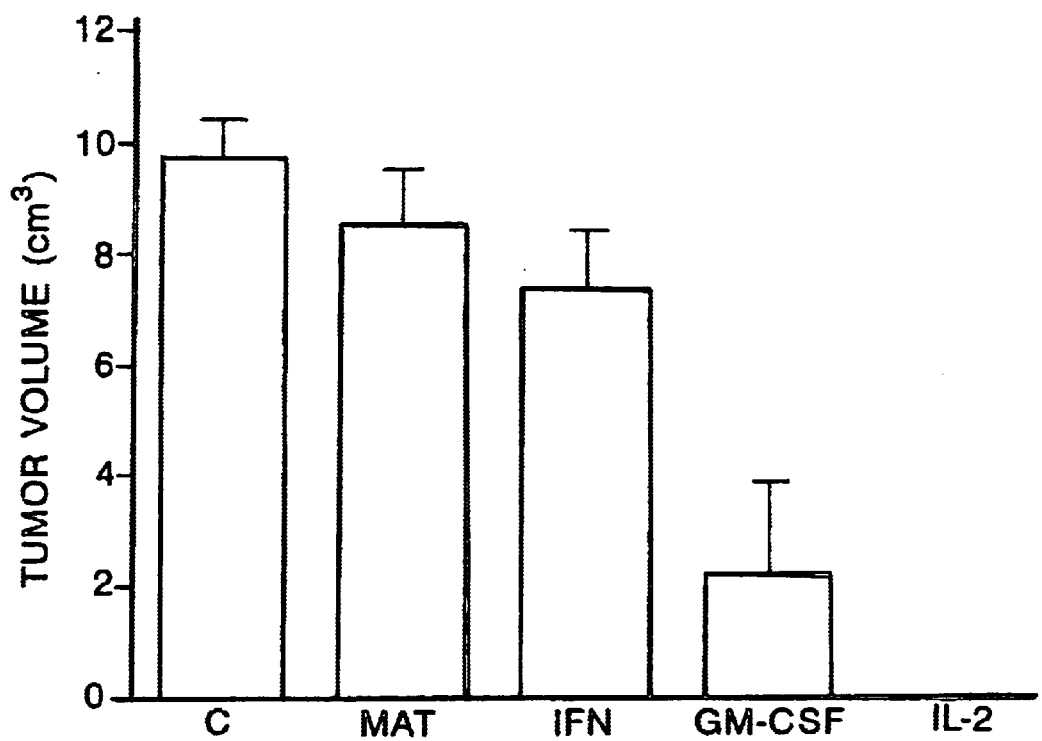
Figure 25B:
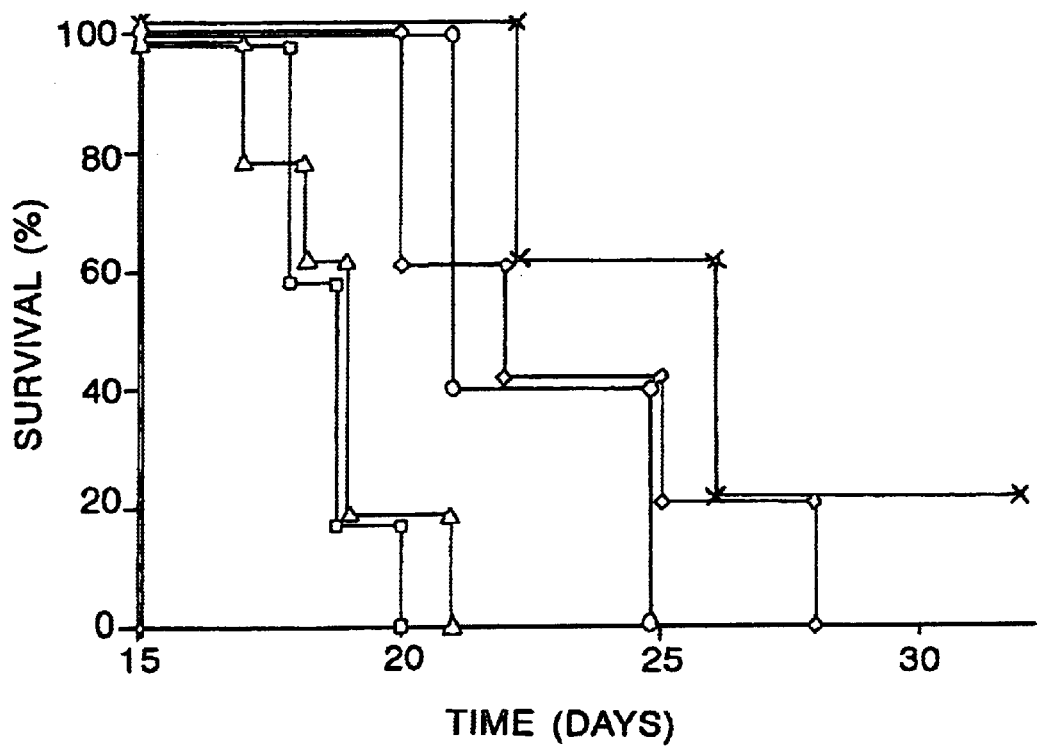

FIG. 25:A–B Relates potency of cytokines in inhibiting growth of primary tumors. Animals administered un-modified parental tumor cells and administered as a vaccine transfected cells. Following prostatectomy of rodent tumor results in survival increase.

Figure 26:
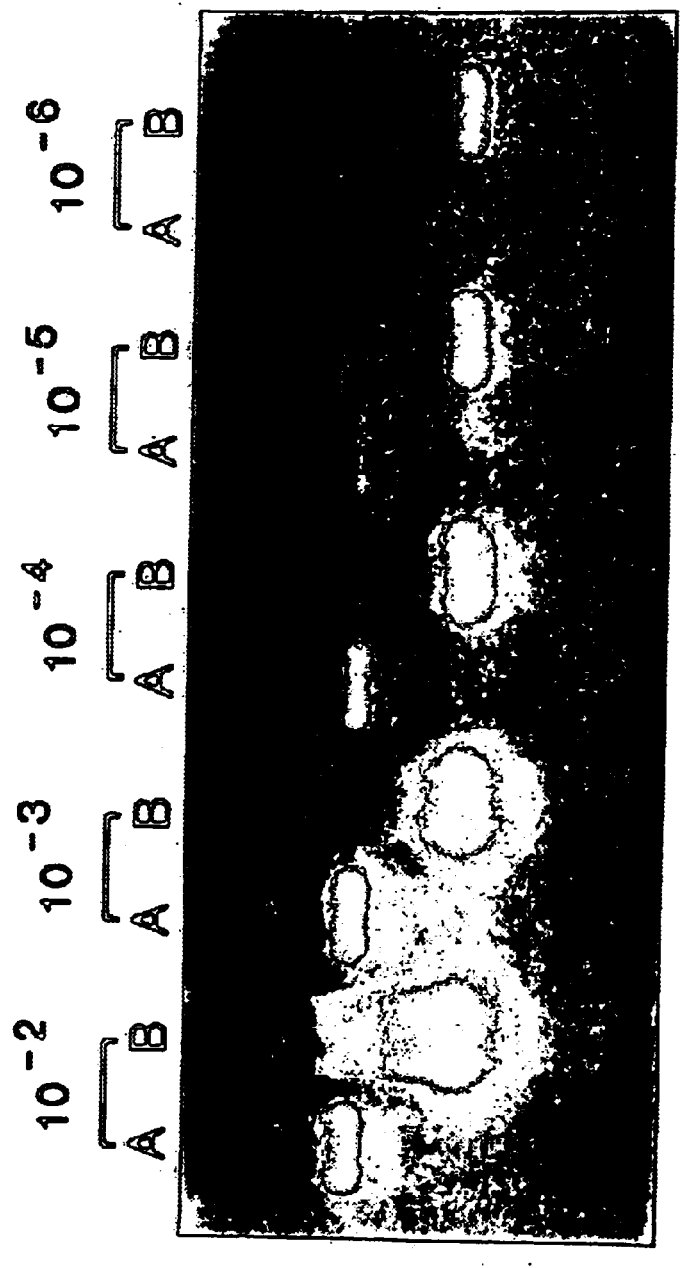

FIG. 26: PCR amplification with nested primers improved our level of detection of prostatic cells from approximately one prostatic cell per 10,000 MCF-7 cells to better than one cell per million MCF-7 cells, using either PSA.

Figure 27:
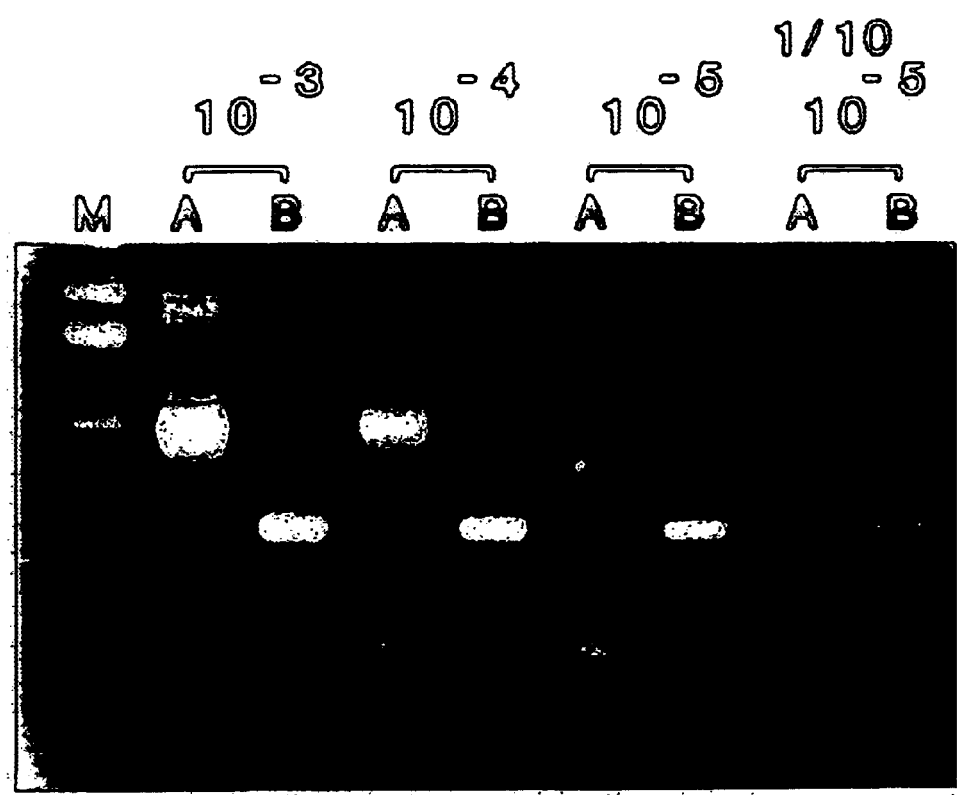

FIG. 27: PCR amplification with nested primers improved our level of detection of prostatic cells from approximately one prostatic cell per 10,000 MCF-7 cells to better than one cell per million MCF-7 cells, using PSM-derived primers.

Figure 28:
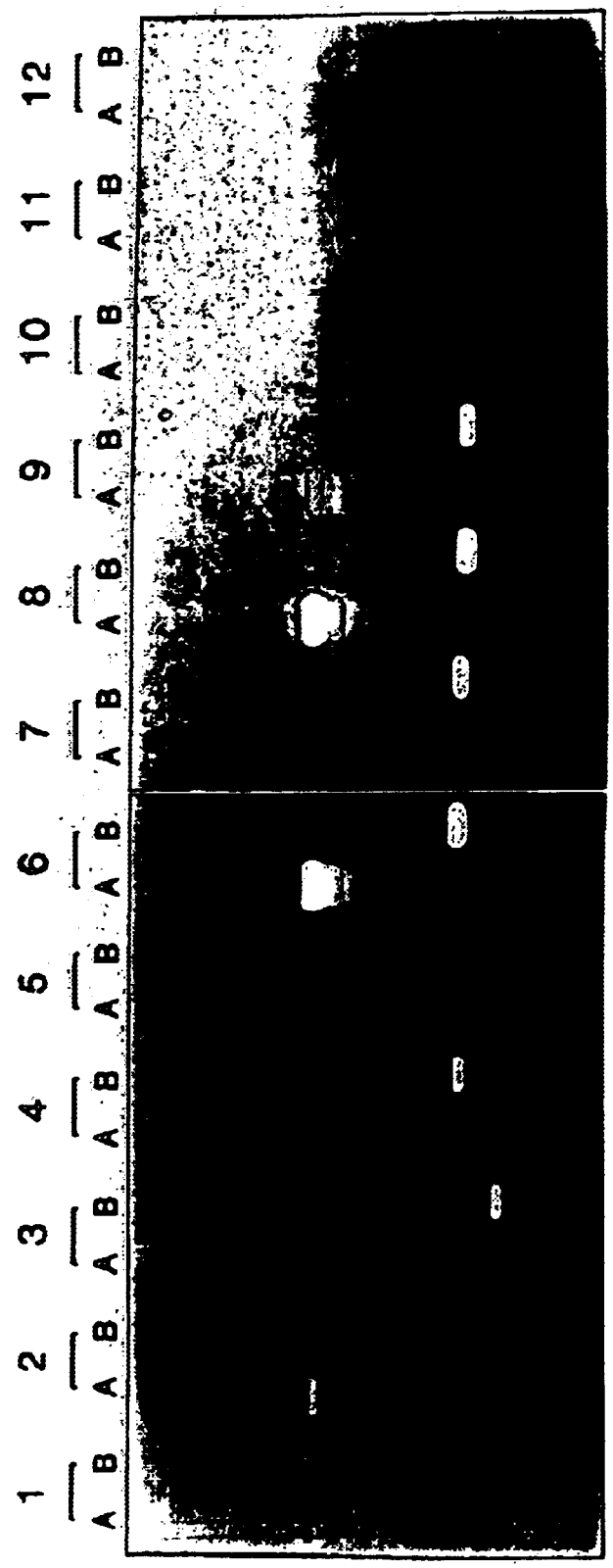

FIG. 28: A representative ethidium stained gel photograph for PSM-PCR. Samples run in lane A represent PCR products generated from the outer primers and samples in lanes labeled B are products of inner primer pairs.

Figure 29:
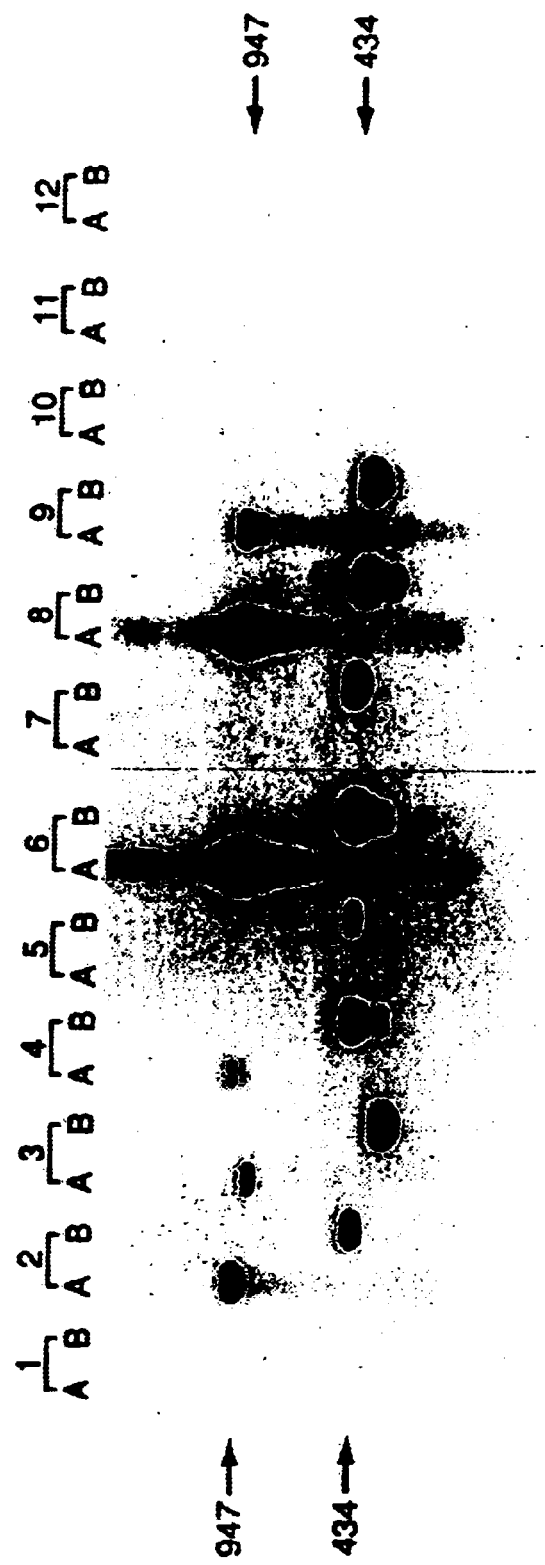

FIG. 29: PSM Southern blot autoradiograph. The sensitivity of the Southern blot analysis exceeded that of ethidium staining, as can be seen in several samples where the outer product is not visible on FIG. 3A–D, but is detectable by Southern blotting as shown in FIG. 4.

FIG. 30: Characteristics of the 16 patients analyzed with respect to their clinical stage, treatment, serum PSA and PAP values, and results of assay.

SUMMARY OF THE INVENTION

This invention provides an isolated mammalian nucleic acid molecule encoding a mammalian prostate-specific membrane (PSM) antigen. The isolated mammalian nucleic acid may be DNA, cDNA or RNA.

This invention also provides nucleic acid molecule comprising a nucleic acid molecule of at least 15 nucleotides capable of specifically hybridizing with a sequence included within the sequence of a nucleic acid molecule encoding the PSM antigen. The nucleic acid molecule may either be DNA or RNA.

This invention provides nucleic acid molecule of at least nucleotides capable of specifically hybridizing with a sequence of a nucleic acid molecule which is complementary to the nucleic acid molecule encoding a mammalian prostate-specific membrane antigen.

This invention further provides a method of detecting expression of the PSM antigen which comprises obtaining total mRNA from the cell and contacting the mRNA so obtained with a labelled PSM antigen specific nucleic acid molecule under hybridizing conditions, determining the presence of mRNA hybridized to the probe, and thereby detecting the expression of the PSM antigen by the cell. The PSM antigen in tissue sections may be similarly detected.

This invention provides isolated nucleic acid molecule of PSM antigen operatively linked to a promoter of RNA transcription. This invention further provides a vector which comprises an isolated mammalian nucleic acid molecule of PSM antigen.

This invention further provides a host vector system for the production of a polypeptide having the biological activity of a mammalian PSM antigen which comprises the vector comprising the mammalian nucleic acid molecule encoding a mammalian PSM antigen and a suitable host. The suitable host for the expression of PSM antigen may be a bacterial cell, insect cell, or mammalian cell.

This invention also provides a method of producing a polypeptide having the biological activity of a mammalian PSM antigen which comprises growing the host cell of vector system having a vector comprising the isolated mammalian nucleic acid molecule encoding a mammalian PSM antigen and a suitable host under suitable conditions permitting production of the polypeptide and recovery of the polypeptide so produced.

This invention provides a method for determining whether a ligand can bind to a mammalian PSM antigen which comprises contacting a mammalian cell having an isolated mammalian DNA molecule encoding a mammalian PSM antigen with the ligand under conditions permitting binding of ligands to the mammalian PSM antigen, and determining whether the ligand binds to a mammalian PSM antigen. This invention further provides ligands which bind to PSM antigen.

This invention provides purified mammalian PSM antigen. This invention also provides a polypeptide encoded by the isolated mammalian nucleic acid molecule encoding a mammalian PSM antigen. This invention further provides a method to identify and purify ligands of mammalian PSM antigen.

This invention further provides a method to produce both polyclonal and monoclonal antibody using purified PSM antigens or polypeptides encoded by an isolated mammalian nucleic acid molecule encoding a mammalian PSM antigen.

This invention provides polyclonal and monoclonal antibody most likely but not limited to directed either to peptide Asp-Glu-Leu-Lys-Ala-Glu (SEQ ID No. 35), or Asn-Glu-Asp-Gly-Asn-Glu (SEQ ID No. 36) or Lys-Ser-Pro-Asp-Glu-Gly (SEQ ID No. 37) of the PSM antigen.

This invention provides a therapeutic agent comprising an antibody directed against a mammalian PSM antigen and a cytotoxic agent conjugated thereto.

This invention also provides a method of imaging prostate cancer in human patients which comprises administering to the patient at least one antibody directed against PSM antigen, capable of binding to the cell surface of the prostate cancer cell and labeled with an imaging agent under conditions so as to form a complex between the monoclonal antibody and the cell surface PSM antigen. This invention further provides a composition comprising an effective imaging amount of the antibody directed against PSM antigen and a pharmaceutically acceptable carrier.

This invention further provides a method of imaging prostate cancer in human patients which comprises administering to the patient multiple antibodies directed towards different PSM epitopes.

The invention also provides a method of imaging prostate cancer in human patients which comprises administering to the patient at least one ligand, capable of binding to the cell surface of the prostate cancer cell and labelled with an imaging agent under conditions so as to form a complex between the ligand and the cell surface PSM antigen. This invention further provides a composition comprising an effective imaging amount of PSM antigen and a pharmaceutically acceptable carrier.

This invention provides an immunoassay for measuring the amount of the PSM antigen in a biological sample, e.g. serum, comprising steps of a) contacting the biological sample with at least one PSM antibody to form a complex with said antibody and the PSM antigen, and b) measuring the amount of PSM antigen in said biological sample by measuring the amount of said complex.

This invention also provides an immunoassay for measuring the amount of the PSM antigen in a biological sample comprising steps of a) contacting the biological sample with at least one PSM ligand to form a complex with said ligand and the PSM antigen, and b) measuring the amount of the PSM antigen in said biological sample by measuring the amount of said complex.

This invention provides a method to purify mammalian PSM antigen comprising steps of: a) coupling the antibody directed against PSM antigen to a solid matrix; b) incubating the coupled antibody of a) with a cell lysate containing PSM antigen under the condition permitting binding of the antibody and PSM antigen; c) washing the coupled solid matrix to eliminate impurities and d) eluting the PSM antigen from the bound antibody.

This invention further provides transgenic nonhuman mammals which comprises an isolated nucleic acid molecule of PSM antigen. This invention also provides a transgenic nonhuman mammal whose genome comprises antisense DNA complementary to DNA encoding a mammalian PSM antigen so placed as to be transcribed into antisense mRNA complementary to mRNA encoding the PSM antigen and which hybridizes to mRNA encoding the PSM antigen thereby reducing its translation.

This invention provides a method of suppressing or modulating metastatic ability of prostate tumor cells, prostate tumor growth or elimination of prostate tumor cells comprising introducing a DNA molecule encoding a prostate specific membrane antigen operatively linked to a 5' regulatory element into a tumor cell of a subject, in a way that expression of the prostate specific membrane antigen is under the control of the regulatory element, thereby suppressing or modulating metastatic ability of prostate tumor cells, prostate tumor growth or elimination of prostate tumor cells.

This invention provides a method of suppressing or modulating metastatic ability of prostate tumor cells, prostate tumor growth or elimination of prostate tumor cells, comprising introducing a DNA molecule encoding a prostate specific membrane antigen operatively linked to a 5' regulatory element coupled with a therapeutic DNA into a tumor cell of a subject, thereby suppressing or modulating metastatic ability of prostate tumor cells, prostate tumor growth or elimination of prostate tumor cells.

This invention provides a therapeutic vaccine for preventing human prostate tumor growth or stimulation of prostate tumor cells in a subject, comprising administering an effective amount to the prostate cell, and a pharmaceutical acceptable carrier, thereby preventing the tumor growth or stimulation of tumor cells in the subject.

This invention provides a method of detecting hematogenous micrometastic tumor cells of a subject, comprising (A) performing nested polymerase chain reaction (PCR) on blood, bone marrow, or lymph node samples of the subject using the prostate specific membrane antigen primers, and (B) verifying micrometastases by DNA sequencing and Southern analysis, thereby detecting hematogenous micrometastic tumor cells of the subject.

This invention provides a method of abrogating the mitogenic response due to transferrin, comprising introducing a DNA molecule encoding prostate specific membrane antigen operatively linked to a 5' regulatory element into a tumor cell, the expression of which gene is directly associated with a defined pathological effect within a multicellular organism, thereby abrogating mitogen response due to transferrin.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

C=cytosine
T=thymidine
A=adenosine
G=guanosine

A "gene" means a nucleic acid molecule, the sequence of which includes all the information required for the normal regulated production of a particular protein, including the structural coding sequence, promoters and enhancers.

This invention provides an isolated mammalian nucleic acid encoding a mammalian prostate-specific membrane (PSM) antigen.

This invention further provides an isolated mammalian DNA molecule of an isolated mammalian nucleic acid molecule encoding a mammalian prostate-specific membrane antigen. This invention also provides an isolated mammalian cDNA molecule encoding a mammalian prostate-specific membrane antigen. This invention provides an isolated mammalian RNA molecule encoding a mammalian prostate-specific membrane antigen.

In the preferred embodiment of this invention, the isolated nucleic sequence is cDNA from human as shown in sequence ID number 1. This human sequence was submitted to GenBank (Los Alamos National Laboratory, Los Alamos, N.M.) with Accession Number, M99487 and the description as PSM, *Homo sapiens*, 2653 base-pairs.

This invention also encompasses DNAs and cDNAs which encode amino acid sequences which differ from those of PSM antigen, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated mammalian nucleic acid molecules encoding a mammalian prostate-specific membrane antigen are useful for the development of probes to study the tumorgenesis of prostate cancer.

This invention also provides nucleic acid molecules of at least 15 nucleotides capable of specifically hybridizing with a sequence of a nucleic acid molecule encoding the prostate-specific membrane antigen.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a nucleic acid molecule encoding the prostate-specific membrane antigen can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes PSM antigen into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the PSM antigen molecule downstream of a bacteriophage promoter such as T3, T7 or SP6. Large amounts of RNA probe may be produced by incubating the labeled nucleotides with the linearized PSM antigen fragment where it contains an upstream promoter in the presence of the appropriate RNA polymerase.

This invention also provides a nucleic acid molecule of at least 15 nucleotides capable of specifically hybridizing with a sequence of a nucleic acid molecule which is complementary to the mammalian nucleic acid molecule encoding a mammalian prostate-specific membrane antigen. This molecule may either be a DNA or RNA molecule.

The current invention further provides a method of detecting the expression of a mammalian PSM antigen expression in a cell which comprises obtaining total mRNA from the cell, contacting the mRNA so obtained with a labelled nucleic acid molecule of at least 15 nucleotides capable of specifically hybridizing with a sequence of the nucleic acid molecule encoding a mammalian PSM antigen under hybridizing conditions, determining the presence of mRNA hybridized to the molecule and thereby detecting the expression of the mammalian prostate-specific membrane antigen in the cell. The nucleic acid molecules synthesized above may be used to detect expression of a PSM antigen by detecting the presence of mRNA coding for the PSM antigen. Total mRNA from the cell may be isolated by many procedures well known to a person of ordinary skill in the art. The hybridizing conditions of the labelled nucleic acid molecules may be determined by routine experimentation well known in the art. The presence of mRNA hybridized to the probe may be determined by gel electrophoresis or other methods known in the art. By measuring the amount of the hybrid made, the expression of the PSM antigen by the cell can be determined. The labelling may be radioactive. For an example, one or more radioactive nucleotides can be incorporated in the nucleic acid when it is made.

In one embodiment of this invention, nucleic acids are extracted by precipitation from lysed cells and the mRNA is isolated from the extract using an oligo-dT column which binds the poly-A tails of the mRNA molecules (13). The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention further provides another method to detect expression of a PSM antigen in tissue sections which comprises contacting the tissue sections with a labelled nucleic acid molecule of at least 15 nucleotides capable of specifically hybridizing with a sequence of nucleic acid molecules encoding a mammalian PSM antigen under hybridizing conditions, determining the presence of mRNA hybridized to the molecule and thereby detecting the expression of the mammalian PSM antigen in tissue sections. The probes are also useful for in-situ hybridization or in order to locate tissues which express this gene, or for other hybridization assays for the presence of this gene or its mRNA in various biological tissues. The in-situ hybridization using a labelled nucleic acid molecule is well known in the art. Essentially, tissue sections are incubated with the labelled nucleic acid molecule to allow the hybridization to occur. The molecule will carry a marker for the detection because it is "labelled", the amount of the hybrid will be determined based on the detection of the amount of the marker and so will the expression of PSM antigen.

This invention further provides isolated PSM antigen nucleic acid molecule operatively linked to a promoter of RNA transcription. The isolated PSM antigen sequence can be linked to vector systems. Various vectors including plasmid vectors, cosmid vectors, bacteriophage vectors and other viruses are well known to ordinary skilled practitioners. This invention further provides a vector which comprises the isolated nucleic acid molecule encoding for the PSM antigen.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the PSM sequence is cloned in the NotI/SalI site of pSPORT/vector (Gibco®-BRL). This plasmid, p55SSA-PSM, was deposited on Aug. 14, 1992 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, p55A-PSM, was accorded ATCC Accession Number 75294.

This invention further provides a host vector system for the production of a polypeptide having the biological activity of the prostate-specific membrane antigen. These vectors may be transformed into a suitable host cell to form a host cell vector system for the production of a polypeptide having the biological activity of PSM antigen.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (14). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the PSM antigen.

This invention further provides an isolated DNA or cDNA molecule described hereinabove wherein the host cell is selected from the group consisting of bacterial cells (such as *E. coli*), yeast cells, fungal cells, insect cells and animal cells. Suitable animal cells include, but are not limited to Vero cells, HeLa cells, Cos cells, CV1 cells and various primary mammalian cells.

This invention further provides a method of producing a polypeptide having the biological activity of the prostate-specific membrane antigen which comprising growing host cells of a vector system containing the PSM antigen sequence under suitable conditions permitting production of the polypeptide and recovering the polypeptide so produced.

This invention provides a mammalian cell comprising a DNA molecule encoding a mammalian PSM antigen, such as a mammalian cell comprising a plasmid adapted for expression in a mammalian cell, which comprises a DNA molecule encoding a mammalian PSM antigen and the regulatory elements necessary for expression of the DNA in the mammalian cell so located relative to the DNA encoding the mammalian PSM antigen as to permit expression thereof.

Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the mammalian PSM antigen may be otherwise introduced into mammalian cells, e.g., by microinjection, to obtain mammalian cells which comprise DNA, e.g., cDNA or a plasmid, encoding a mammalian PSM antigen.

This invention provides a method for determining whether a ligand can bind to a mammalian prostate-specific membrane antigen which comprises contacting a mammalian cell comprising an isolated DNA molecule encoding a mammalian prostate-specific membrane antigen with the ligand under conditions permitting binding of ligands to the mammalian prostate-specific membrane antigen, and thereby determining whether the ligand binds to a mammalian prostate-specific membrane antigen.

This invention further provides ligands bound to the mammalian PSM antigen.

This invention also provides a therapeutic agent comprising a ligand identified by the above-described method and a cytotoxic agent conjugated thereto. The cytotoxic agent may either be a radioisotope or a toxin. Examples of radioisotopes or toxins are well known to one of ordinary skill in the art.

This invention also provides a method of imaging prostate cancer in human patients which comprises administering to the patients at least one ligand identified by the above-described method, capable of binding to the cell surface of the prostate cancer cell and labelled with an imaging agent under conditions permitting formation of a complex between the ligand and the cell surface PSM antigen. This invention further provides a composition comprising an effective imaging agent of the PSM antigen ligand and a pharmaceutically acceptable carrier. Pharmaceutically acceptable carriers are well known to one of ordinary skill in the art. For an example, such a pharmaceutically acceptable carrier can be physiological saline.

Also provided by this invention is a purified mammalian PSM antigen. As used herein, the term "purified prostate-specific membrane antigen" shall mean isolated naturally-occurring prostate-specific membrane antigen or protein (purified from nature or manufactured such that the primary, secondary and tertiary conformation, and posttranslational modifications are identical to naturally-occurring material) as well as non-naturally occurring polypeptides having a primary structural conformation (i.e. continuous sequence of amino acid residues). Such polypeptides include derivatives and analogs.

This invention further provides a polypeptide encoded by the isolated mammalian nucleic acid sequence of PSM antigen.

It is believed that there may be natural ligand interacting with the PSM antigen. This invention provides a method to identify such natural ligand or other ligand which can bind to the PSM antigen. A method to identify the ligand comprises a) coupling the purified mammalian PSM antigen to a solid matrix, b) incubating the coupled purified mammalian PSM protein with the potential ligands under the conditions permitting binding of ligands and the purified PSM antigen; c) washing the ligand and coupled purified mammalian PSM antigen complex formed in b) to eliminate the nonspecific binding and impurities and finally d) eluting the ligand from the bound purified mammalian PSM antigen. The techniques of coupling proteins to a solid matrix are well known in the art. Potential ligands may either be deduced from the structure of mammalian PSM or by other empirical experiments known by ordinary skilled practitioners. The conditions for binding may also easily be determined and protocols for carrying such experimentation have long been well documented (15). The ligand-PSM antigen complex will be washed. Finally, the bound ligand will be eluted and characterized. Standard ligands characterization techniques are well known in the art.

The above method may also be used to purify ligands from any biological source. For purification of natural ligands in the cell, cell lysates, serum or other biological samples will be used to incubate with the mammalian PSM antigen bound on a matrix. Specific natural ligand will then be identified and purified as above described.

With the protein sequence information, antigenic areas may be identified and antibodies directed against these areas may be generated and targeted to the prostate cancer for imaging the cancer or therapies.

This invention provides an antibody directed against the amino acid sequence of a mammalian PSM antigen.

This invention provides a method to select specific regions on the PSM antigen to generate antibodies. The protein sequence may be determined from the PSM DNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to mammalian PSM antigen. For an example, hydrophilic sequences of the human PSM antigen shown in hydrophilicity plot of FIG. 16 may be easily selected. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian PSM antigen in living animals, in humans, or in biological tissues or fluids isolated from animals or humans.

In one embodiment peptides Asp-Glu-Leu-Lys-Ala-Glu (SEQ ID No. 35), Asn-Glu-Asp-Gly-Asn-Glu (SEQ ID No. 36) and Lys-Ser-Pro-Asp-Glu-Gly (SEQ ID No. 37) of human PSM antigen are selected.

This invention further provides polyclonal and monoclonal antibody(ies) against peptides Asp-Glu-Leu-Lys-Ala-Glu (SEQ ID No. 35), Asn-Glu-Asp-Gly-Asn-Glu (SEQ ID No. 36) and Lys-Ser-Pro-Asp-Glu-Gly (SEQ ID No. 37).

This invention provides a therapeutic agent comprising antibodies or ligand(s) directed against PSM antigen and a cytotoxic agent conjugated thereto or antibodies linked enzymes which activate prodrug to kill the tumor. The cytotoxic agent may either be a radioisotope or toxin.

This invention provides a method of imaging prostate cancer in human patients which comprises administering to the patient the monoclonal antibody directed against the peptide of the mammalian PSM antigen capable of binding to the cell surface of the prostate cancer cell and labeled with an imaging agent under conditions permitting formation of a complex between the monoclonal antibody and the cell surface prostate-specific membrane antigen. The imaging agent is a radioisotope such as Indium$^{111}$.

This invention further provides a prostate cancer specific imaging agent comprising the antibody directed against PSM antigen and a radioisotope conjugated thereto.

This invention also provides a composition comprising an effective imaging amount of the antibody directed against the PSM antigen and a pharmaceutically acceptable carrier. The methods to determine effective imaging amounts are well known to a skilled practitioner. One method is by titration using different amounts of the antibody.

This invention further provides an immunoassay for measuring the amount of the prostate-specific membrane antigen in a biological sample comprising steps of a) contacting the biological sample with at least one antibody directed against the PSM antigen to form a complex with said antibody and the prostate-specific membrane antigen, and b) measuring the amount of the prostate-specific membrane antigen in said biological sample by measuring the amount of said complex. One example of the biological sample is a serum sample.

This invention provides a method to purify mammalian prostate-specific membrane antigen comprising steps of a) coupling the antibody directed against the PSM antigen to a solid matrix; b) incubating the coupled antibody of a) with lysate containing prostate-specific membrane antigen under the condition which the antibody and prostate membrane specific can bind; c) washing the solid matrix to eliminate impurities and d) eluting the prostate-specific membrane antigen from the coupled antibody.

This invention also provides a transgenic nonhuman mammal which comprises the isolated nucleic acid molecule encoding a mammalian PSM antigen. This invention further provides a transgenic nonhuman mammal whose genome comprises antisense DNA complementary to DNA encoding a mammalian prostate-specific membrane antigen so placed as to be transcribed into antisense mRNA complementary to mRNA encoding the prostate-specific membrane antigen and which hybridizes to mRNA encoding the prostate specific antigen thereby reducing its translation.

Animal model systems which elucidate the physiological and behavioral roles of mammalian PSM antigen are produced by creating transgenic animals in which the expression of the PSM antigen is either increased or decreased, or the amino acid sequence of the expressed PSM antigen is altered, by a variety of techniques. Examples of these techniques include, but are not limited to: 1) Insertion of normal or mutant versions of DNA encoding a mammalian PSM antigen, by microinjection, electroporation, retroviral transfection or other means well known to those skilled in the art, into appropriate fertilized embryos in order to produce a transgenic animal (16) or 2) Homologous recombination (17) of mutant or normal, human or animal versions of these genes with the native gene locus in transgenic animals to alter the regulation of expression or the structure of these PSM antigen sequences. The technique of homologous recombination is well known in the art. It replaces the native gene with the inserted gene and so is useful for producing an animal that cannot express native PSM antigen but does express, for example, an inserted mutant PSM antigen, which has replaced the native PSM antigen in the animal's genome by recombination, resulting in underexpression of the transporter. Microinjection adds genes to the genome, but does not remove them, and so is useful for producing an animal which expresses its own and added PSM antigens, resulting in overexpression of the PSM antigens.

One means available for producing a transgenic animal, with a mouse as an example, is as follows: Female mice are mated, and the resulting fertilized eggs are dissected out of their oviducts. The eggs are stored in an appropriate medium such as M2 medium (16). DNA or cDNA encoding a mammalian PSM antigen is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Another use of the PSM antigen sequence is to isolate homologous gene or genes in different mammals. The gene or genes can be isolated by low stringency screening of either cDNA or genomic libraries of different mammals using probes from PSM sequence. The positive clones identified will be further analyzed by DNA sequencing techniques which are well known to an ordinary person skilled in the art. For example, the detection of members of the protein serine kinase family by homology probing (18).

This invention provides a method of suppressing or modulating metastatic ability of prostate tumor cells, prostate tumor growth or elimination of prostate tumor cells comprising introducing a DNA molecule encoding a prostate specific membrane antigen operatively linked to a 5' regulatory element into a tumor cell of a subject, in a way that expression of the prostate specific membrane antigen is under the control of the regulatory element, thereby suppressing or modulating metastatic ability of prostate tumor cells, prostate tumor growth or elimination of prostate tumor cells. The subject may be a mammal or more specifically a human.

In one embodiment, the DNA molecule encoding prostate specific membrane antigen operatively linked to a 5' regulatory element forms part of a transfer vector which is inserted into a cell or organism. In addition the vector is capable or replication and expression of prostate specific membrane antigen. The DNA molecule encoding prostate specific membrane antigen can be integrated into a genome of a eukaryotic or prokaryotic cell or in a host cell containing and/or expressing a prostate specific membrane antigen.

Further, the DNA molecule encoding prostate specific membrane antigen may be introduced by a bacterial, viral, fungal, animal, or liposomal delivery vehicle. Other means are also available and known to an ordinary skilled practitioner.

Further, the DNA molecule encoding a prostate specific membrane antigen operatively linked to a promoter or enhancer. A number of viral vectors have been described including those made from various promoters and other regulatory elements derived from virus sources. Promters consist of short arrays of nucleic acid sequences that interact specifically with cellular proteins involved in transcription. The combination of different recognition sequences and the cellular concentration of the cognate transcription factors determines the efficiency with which a gene is transcribed in a particular cell type.

Examples of suitable promoters include a viral promoter. Viral promoters include: adenovirus promoter, an simian virus 40 (SV40) promoter, a cytomegalovirus (CMV) promoter, a mouse mammary tumor virus (MMTV) promoter, a Malony murine leukemia virus promoter, a murine sarcoma virus promoter, and a Rous sarcoma virus promoter.

Further, another suitable promoter is a heat shock promoter. Additionally, a suitable promoter is a bacteriophage promoter. Examples of suitable bacteriophage promoters include but not limited to, a T7 promoter, a T3 promoter, an SP6 promoter, a lambda promoter, a baculovirus promoter.

Also suitable as a promoter is an animal cell promoter such as an interferon promoter, a metallothionein promoter, an immunoglobulin promoter. A fungal promoter is also a suitable promoter. Examples of fungal promoters include but are not limited to, an ADC1 promoter, an ARG promoter, an ADH promoter, a CYC1 promoter, a CUP promoter, an ENO1 promoter, a GAL promoter, a PHO promoter, a PGK promoter, a GAPDH promoter, a mating type factor promoter. Further, plant cell promoters and insect cell promoters are also suitable for the methods described herein.

This invention provides a method of suppressing or modulating metastatic ability of prostate tumor cells, prostate tumor growth or elimination of prostate tumor cells, comprising introducing a DNA molecule encoding a prostate specific membrane antigen operatively linked to a 5' regulatory element coupled with a therapeutic DNA into a tumor cell of a subject, thereby suppressing or modulating metastatic ability of prostate tumor cells, prostate tumor growth or elimination of prostate tumor cells. The subject may be a mammal or more specifically a human.

Further, the therapeutic DNA which is coupled to the DNA molecule encoding a prostate specific membrane antigen operatively linked to a 5' regulatory element into a tumor cell may code for a cytokine, viral antigen, or a pro-drug activating enzyme. Other means are also available and known to an ordinary skilled practitioner.

The cytokine used may be interleukin-2, interleukin-12, interferon alpha, beta or gamma, granulocytic macrophage—colony stimulating factor, or other immunity factors.

In addition, this invention provides a prostate tumor cell, comprising a DNA molecule isolated from mammalian nucleic acid encoding a mammalian prostate-specific membrane antigen under the control of a prostate specific membrane antigen operatively linked to a 5' regulatory element.

As used herein, DNA molecules include complementary DNA (cDNA), synthetic DNA, and genomic DNA.

This invention provides a therapeutic vaccine for preventing human prostate tumor growth or stimulation of prostate tumor cells in a subject, comprising administering an effective amount to the prostate cell, and a pharmaceutical acceptable carrier, thereby preventing the tumor growth or stimulation of tumor cells in the subject. Other means are also available and known to an ordinary skilled practitioner.

This invention provides a method of detecting hematogenous micrometastic tumor cells of a subject, comprising (A) performing nested polymerase chain reaction (PCR) on blood, bone marrow or lymph node samples of the subject using the prostate specific membrane antigen primers, and (B) verifying micrometastases by DNA sequencing and Southern analysis, thereby detecting hematogenous micrometastic tumor cells of the subject. The subject may be a mammal or more specifically a human.

The micrometastatic tumor cell may be a prostatic cancer and the DNA primers may be derived from prostate specific antigen. Further, the subject may be administered with simultaneously an effective amount of hormones, so as to increase expression of prostate specific membrane antigen.

This invention provides a method of abrogating the mitogenic response due to transferrin, comprising introducing a DNA molecule encoding prostate specific membrane antigen operatively linked to a 5' regulatory element into a tumor cell, the expression of which gene is directly associated with a defined pathological effect within a multicellular organism, thereby abrogating mitogen response due to transferrin. The tumor cell may be a prostate cell.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

Materials and Methods

The approach for cloning the gene involved purification of the antigen in large quantities by immunoprecipitation, and microsequencing of several internal peptides for use in synthesizing degenerate oligonucleotide primers for subsequent use in the polymerase chain reaction (19, 20). A partial cDNA was amplified as a PCR product and this was used as a homologous probe to clone the full-length cDNA molecule from a LNCaP (Lymph Node Carcinoma of Prostate) cell line cDNA plasmid library (8). Early experiments revealed to Us that the CYT-356 antibody (9) was not capable of detecting the antigen produced in bacteria since the epitope was the glycosylated portion of the PSM antigen, and this necessitated our more difficult, yet elaborate approach.

Western Analysis of the PSM Antigen

Figure 1:
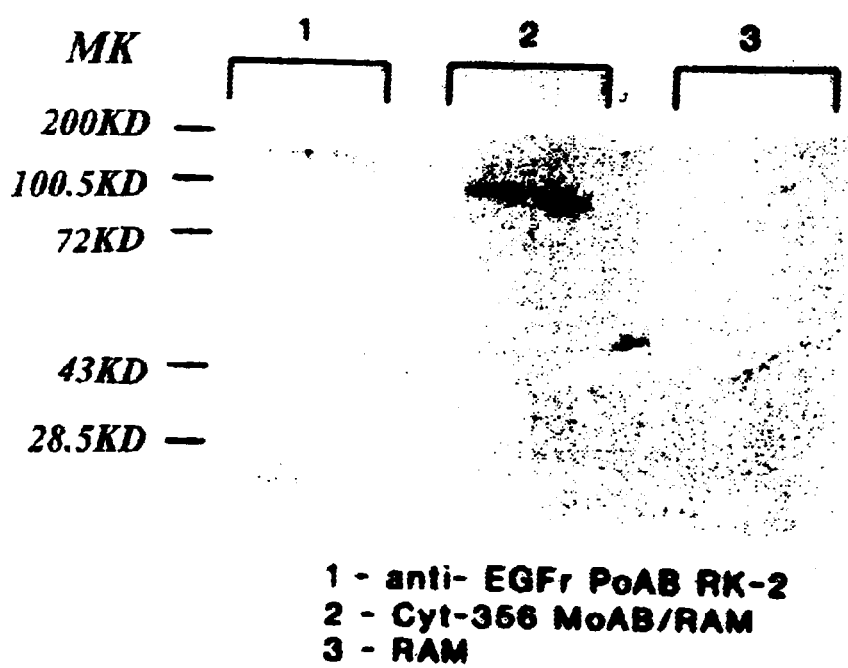
FIG. 1: Signal in lane 2 represent the 100 kD PSM antigen. The EGFr was used as the positive control and is shown in lane 1. Incubation with rabbit antimouse (RAM) antibody alone served as negative control and is shown in lane 3.
Figure 3B:
FIG. 3A–D: Upper two panels are human prostate sections (BPH) staining positively for PSM antigen. The lower two panels show invasive prostate carcinoma human sections staining positively for expression of the PSM antigen.
Figure 3D:
Figure 3A:
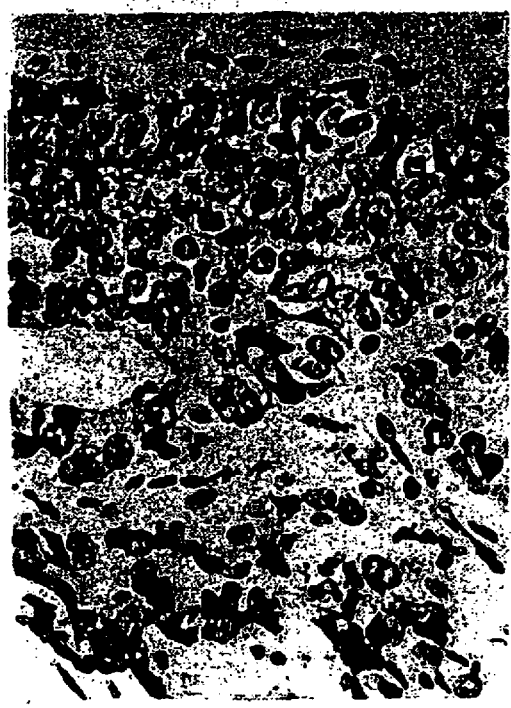
Figure 3C:

Membrane proteins were isolated from cells by hypotonic lysis followed by centrifugation over a sucrose density gradient (21). 10–20 μg of LNCaP, DU-145, and PC-3 membrane proteins were electrophoresed through a 10% SDS-PAGE resolving gel with a 4% stacking gel at 9–10 milliamps for 16–18 hours. Proteins were electroblotted onto PVDF membranes. (Millipore® Corp.) in transfer buffer (48 mM Tris base, 39 mM Glycine, 20% Methanol) at 25 volts overnight at 4° C. Membranes were blocked in TSB (0.15M NaCl, 0.01M Tris base, 5% BSA) for 30 minutes at room temperature followed by incubation with 10–15 μg/ml of CYT-356 monoclonal antibody (Cytogen Corp.) for 2 hours. Membranes were then incubated with 10–15 μg/ml of rabbit anti-mouse immunoglobulin (Accurate Scientific) for 1 hour at room temperature followed by incubation with $^{125}$-Protein A (Amersham®) at $1\times10^6$ cpm/ml at room temperature. Membranes were then washed and autoradiographed for 12–24 hours at −70° C. (FIG. 1).

Immunohistochemical Analysis of PSM Antigen Expression

The avidin-biotin method of immunohistochemical detection was employed to analyze both human tissue sections and cell lines for PSM Antigen expression (22). Cryostat-cut prostate tissue sections (4–6 μm thick) were fixed in methanol/acetone for 10 minutes. Cell cytospins were made on glass slides using 50,000 cells/100 μg/slide. Samples were treated with 1% hydrogen peroxide in PBS for 10–15 minutes in order to remove any endogenous peroxidase activity. Tissue sections were washed several times in PBS, and then incubated with the appropriate suppressor serum for minutes. The suppressor serum was drained off and the sections or cells were then incubated with the diluted CYT-356 monoclonal antibody for 1 hour. Samples were then washed with PBS and sequentially incubated with secondary antibodies (horse or goat immunoglobulins, 1:200 dilution for 30 minutes), and with avidin-biotin complexes (1:25 dilution for 30 minutes). DAB was used as a chromogen, followed by hematoxylin counterstaining and mounting. Frozen sections of prostate samples and duplicate cell cytospins were used as controls for each experiment. As a positive control, the anti-cytokeratin monoclonal antibody CAM 5.2 was used following the same procedure described above. Tissue sections are considered by us to express the PSM antigen if at least 5% of the cells demonstrate immunoreactivity. Our scoring system is as follows: 1=<5%; 2=5–19%; 3=20–75%; and 4=>75% positive cells. Homogeneity versus heterogeneity was accounted for by evaluating positive and negative cells in 3–5 high power light microscopic fields (400×), recording the percentage of positive cells among 100–500 cells. The intensity of immunostaining is graded on a 1+ to 4+ scale, where 1+ represents mild, 2–3+ represents moderate, and 4+ represents intense immunostaining as compared to positive controls.

Immunoprecipitation of the PSM Antigen

80%-confluent LNCaP cells in 100 mm petri dishes were starved in RPMI media without methionine for 2 hours, after which $^{35}$S-Methionine was added at 100 μCi/ml and the cells were grown for another 16–18 hours. Cells were then washed and lysed by the addition of 1 ml of lysia buffer (1% Triton X-100, 50 mM Hepes pH 7.5, 10% glycerol, 150 mM $MgCl_2$, 1 mM PMSF, and 1 mM EGTA) with incubation for 20 minutes at 4° C. Lysates were pre-cleared by mixing with Pansorbin® cells (Calbiochem®) for 90 minutes at 4° C. Cell lysates were then mixed with Protein A Sepharoses CL-4B beads (Pharmacia®) previously bound with CYT-356 antibody (Cytogen Corp.) and RAM antibody (Accurate Scientific) for 3–4 hours at 4° C. 12 μg of antibody was used per 3 mg of beads per petri dish. Beads were then washed with HNTG buffer (20 mM Hepes pH 7.5, 150 mM NaCl, 0.1% Triton X-100, 10% glycerol, and 2 mM Sodium Orthovanadate), resuspended in sample loading buffer containing β-mercaptoethanol, denatured at 95° C. for 5–10 minutes and run on a 10% SDS-PAGE gel with a 4° stacking gel at 10 milliamps overnight. Gels were stained with Coomassie Blue, destained with acetic acid/methanol, and dried down in a vacuum dryer at 60° C. Gels were then autoradiographed for 16–24 hours at −70° C. (FIG. 2A–D).

Large-scale Immunoprecipitation and Peptide Sequencing

The procedure described above for immunoprecipitation was repeated with 8 confluent petri dishes containing approximately 6×10$^7$ LNCaP cells. The immunoprecipitation product was pooled and loaded into two lanes of a 10% SDS-PAGE gel and electrophoresed at 9–10 milliamps for 16 hours. Proteins were electroblotted onto Nitrocellulose BA-85 membranes (Schleicher and Schuell®) for 2 hours at 75 volts at 4° C. in transfer buffer. Membranes were stained with Ponceau Red to visualize the proteins and the 100 kD protein band was excised, solubilized, and digested proteolytically with trypsin. HPLC was then performed on the digested sample on an Applied Biosystems Model 171C and clear dominant peptide peaks were selected and sequenced by modified Edman degradation on a modified post liquid Applied Biosystems Model 477A Protein/Peptide Microsequencer (23). Sequencing data on all of the peptides is included within this document. We attempted to sequence the amino-terminus of the PSM antigen by a similar method which involved purifying the antigen by immunoprecipitation and transfer via electro-blotting to a PVDF membrane (Millipore®). Protein was analyzed on an Applied Biosystems Model 477A Protein/Peptide Sequencer and the amino terminus was found to be blocked, and therefore no sequence data could be obtained by this technique.

PSM Antigen Peptide Sequences:

| | |
|---|---|
| 2T17 #5 | SLYES(W)TK (SEQ ID No. 3) |
| 2T22 #9 | (S)YPDGXNLPGG(g)VQR (SEQ ID No. 4) |
| 2T26 #3 | FYDPMFK (SEQ ID No. 5) |
| 2T27 #4 | IYNVIGTL(K) (SEQ ID No. 6) |
| 2T34 #6 | FLYXXTQIPHLAGTEQNFQLAK (SEQ ID No. 7) |
| 2T35 #2 | G/PVILYSDPADYFAPD/GVK (SEQ ID No. 8, 9) |
| 2T38 #1 | AFIDPLGLPDRPFYR (SEQ ID No. 10) |
| 2T46 #8 | YAGESFPGIYDALFDIESK (SEQ ID No. 11) |
| 2T47 #7 | TILFAS(W)DAEEFGXX(q)STE(e)A(E) . . . (SEQ ID No. 12) |

Notes: X means that no residue could be identified at this position. Capital denotes identification but with a lower degree of confidence. (lower case) means residue present but at very low levels . . . indicates sequence continues but has dropped below detection limit.

All of these peptide sequences were verified to be unique after a complete homology search of the translated Genbank computer database.

Degenerate PCR

Sense and anti-sense 5'-unphosphorylated degenerate oligonucleotide primers 17 to 20 nucleotides in length corresponding to portions of the above peptides were synthesized on an Applied Biosystems Model 394A DNA Synthesizer. These primers have degeneracies from 32 to 144. The primers used are shown below. The underlined amino acids in the peptides represent the residues used in primer design.

Peptide 3: <u>FYDPMFK</u> (SEQ ID No. 5)
PSM Primer "A" TT(C or T)-TA(C or T)-GA(C or T)-CCX-ATG-TT (SEQ ID No. 13)
PSM Primer "B" AAC-ATX-GG(A or G)-TC(A or G)-TA(A or G)-AA (SEQ ID No. 14)
Primer A is sense primer and B is anti-sense. Degeneracy is 32-fold.

Peptide 4: <u>IYNVIGTL</u> (K) (SEQ ID No. 6)
PSM Primer "C" AT(T or C or A)-TA(T or C)-AA(T or C)-GTX-AT(T or C or A)-GG (SEQ ID No. 15)
PSM Primer "D" CC(A or T or G)-ATX-AC(G or A)-TT(A or G)-TA(A or G or T)-AT (SEQ ID No. 16)
Primer C is sense primer and D is anti-sense. Degeneracy is 144-fold.

Peptide 2: G/PVILYSD<u>PADYFA</u>PD/GVK (SEQ ID No. 8,9)
PSM Primer "E" CCX-GCX-GA(T or C)-TA(T or C)-TT(T or C)-GC (SEQ ID No. 17)
PSM Primer "F" GC(G or A)-AA(A or G)-TA(A or G)-TXC-GCX-GG (SEQ ID No. 18)
Primer E is sense primer and F is antisense primer. Degeneracy is 128-fold.

Peptide 6: FLYXXTQIPHLAG<u>TEQNFQ</u>LAK (SEQ ID No. 7)
PSM Primer "I" ACX-GA(A or G)-CA(A or G)-AA(T or C)-TT(T or C)-CA(A or G)-CT (SEQ ID No. 19)
PSM Primer "J" AG-(T or C)TG-(A or G)AA-(A or G)TT-(T or C)TG-(T or C)TC-XGT (SEQ ID No. 20)
PSM Primer "K" GA(A or G)-CA(A or G)-AA(T or C)-TT(T or C) CA(A or G)-CT (SEQ ID No. 21)
PSM Primer "L" AG-(T or C)TG-(A or G)AA-(A or G)TT-(T or C)TG (T or C)TC (SEQ ID No. 22)
Primers I and K are sense primers and J and L are anti-sense. I and J have degeneracies of 128-fold and K and L have 32-fold degeneracy.

Peptide 7: TILPAS(<u>W)DAEEFG</u>XX(q)STE(e)A(E) . . . (SEQ ID No. 12)
PSM Primer "M" TGG-GA(T or C)-GCX-GA(A or G)-GA(A S or G)-TT(C or T)-GG (SEQ ID No. 23)
PSM Primer "N" CC-(G or A)AA-(T or C)TC-(T or C)TC-XGC-(A or G)TC-CCA (SEQ ID No. 24)
PSM Primer "O" TGG-GA(T or C)-GCX-GA(A or G)-GA(A or G)-TT (SEQ ID No. 25)
PSM Primer "P" AA-(T or C)TC-(T or C)TC-XGC-(A or G)TC-CCA (SEQ ID No. 26)
Primers M and O are sense primers and N and P are anti-sense. M and N have degeneracy of 64-fold and O and P are 32-fold degenerate.

Degenerate PCR was performed using a Perkin-Elmer Model 480 DNA thermal cycler cDNA template for the PCR was prepared from LNCaP mRNA which had been isolated by standard methods of oligo dT chromatography (Collaborative Research). The cDNA synthesis was carried out as follows:

| | |
|---|---|
| 4.5 µl | LNCaP poly A + RNA (2 µg) |
| 1.0 µl | Oligo dT primers (0.5 µg) |
| 4.5 µl | dH$_2$O |
| 10 µl | |

Incubate at 68° C.×10 minutes.
Quick chill on ice×5 minutes.
Add:

| | |
|---|---|
| 4 µl | 5 × RT Buffer |
| 2 µl | 0.1 M DTT |
| 1 µl | 10 mM dNTPs |
| 0.5 µl | RNasin (Promega) |
| 1.5 µl | dH$_2$O |
| 19 µl | |

Incubate for 2 minutes at 37° C.
Add 1 µl Superscript® Reverse Transcriptase (Gibco®-BRL)
Incubate for 1 hour at 37° C.
Add 30 µl dH$_2$O.
Use 2 µl per PCR reaction.

Degenerate PCR reactions were optimized by varying the annealing temperatures. Mg++ concentrations, primer concentrations, buffer composition, extension times and number of cycles. Our optimal thermal cycler profile was: Denaturation at 94° C.×30 seconds, Annealing at 45–55° C. for 1 minute (depending on the mean $T_m$ of the primers used), and Extension at 72° C. for 2 minutes.

| | |
|---|---|
| 5 µl | 10 × PCR Buffer* |
| 5 µl | 2.5 mM dNTP Mix |
| 5 µl | Primer Mix (containing 0.5–1.0 µg each of sense and anti-sense primers) |
| 5 µl | 100 mM β-mercaptoethanol |
| 2 µl | LNCaP cDNA template |
| 5 µl | 25 mM MgCl₂ (2.5 mM final) |
| 21 µl | dH₂O |
| 2 µl | diluted Taq Polymerase (0.5 U/µl) |
| 50 µl | total volume |

Tubes were overlaid with 60 µl of light mineral oil and amplified for 30 cycles. PCR products were analyzed by electrophoresing 5 µl of each sample on a 2–3% agarose gel followed by staining with Ethidium bromide and photography.

Figure 5:
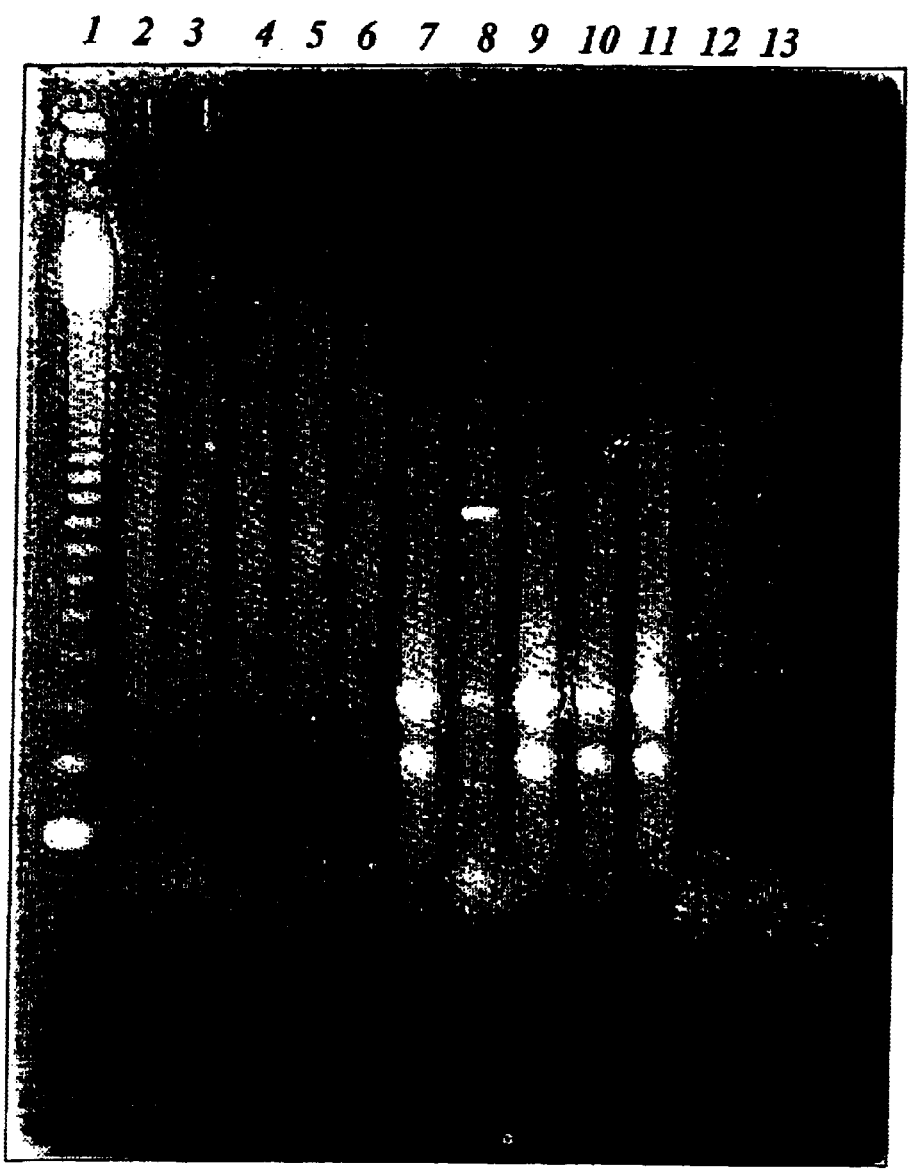
FIG. 5: 3% agarose gels stained with Ethidium bromide revealing PCR products obtained using the degenerate PSM antigen primers. The arrow points to sample IN-20, which is a 1.1 kb PCR product which we later confirmed to be a partial cDNA coding for the PSM gene.

Representative photographs displaying PCR products are shown in FIG. 5.

Cloning of PCR Products

Figures 6A, 6B:
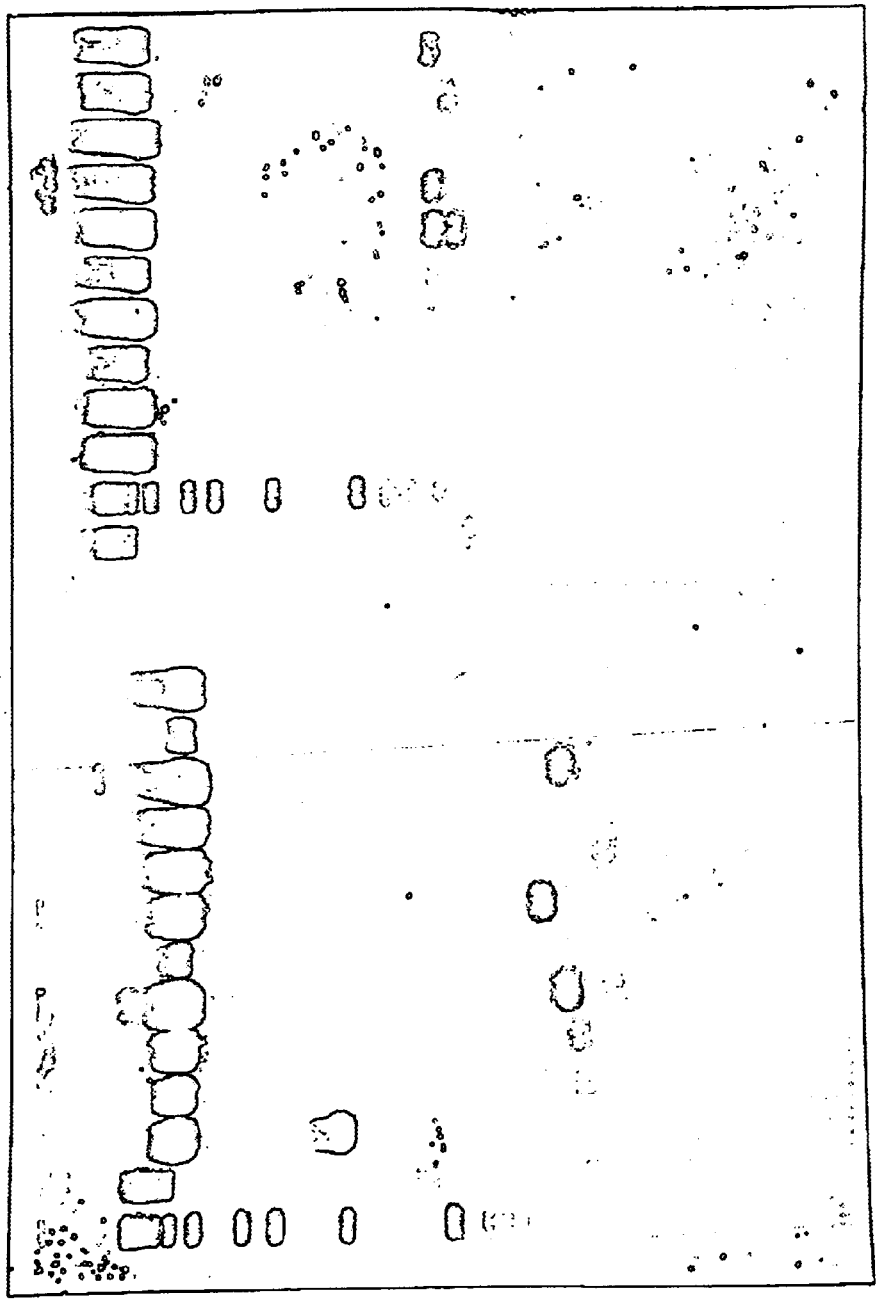
FIG. 6A–B: 2% agarose gels of plasmid DNA resulting from TA cloning of PCR products. Inserts are excised from the PCR II vector (Invitrogen Corp.) by digestion with EcoRI. 1.1 kb PSM gene partial cDNA product is shown in lane 3 of gel 1.

In order to further analyze these PCR products, these products were cloned into a suitable plasmid vector using "TA Cloning" (Invitrogen® Corp.). The cloning strategy employed here is to directly ligate PCR products into a plasmid vector possessing overhanging T residues at the insertion site, exploiting the fact that Tag polymerase leaves overhanging A residues at the ends of the PCR products. The ligation mixes are transformed into competent E. coli cells and resulting colonies are grown up, plasmid DNA is isolated by the alkaline lysis method (24), and screened by restriction analysis (FIG. 6A–B).

DNA Sequencing of PCR Products

TA Clones of PCR products were then sequenced by the dideoxy method (25) using Sequenase (U.S. Biochemical). 3–4 µg of each plasmid DNA was denatured with NaOR and ethanol precipitated. Labeling reactions were carried out as per the manufacturers recommendations using $^{35}$S-ATP, and the reactions were terminated as per the same protocol. Sequencing products were then analyzed on 6% polyacrylamide/7M Urea gels using an IBI sequencing apparatus. Gels were run at 120 watts for 2 hours. Following electrophoresis, the gels were fixed for 15–20 minutes in 10% methanol/10% acetic acid, transferred onto Whatman 3 MM paper and dried down in a Biorad® vacuum dryer at 80° C. for 2 hours. Gels were then autoradiographed at room temperature for 16–24 hours. In order to determine whether the PCR products were the correct clones, we analyzed the sequences obtained at the 5' and 3' ends of the molecules looking for the correct primer sequences, as well as adjacent sequences which corresponded to portions of the peptides not used in the design of the primers.

IN-20 was confirmed to be correct and represent a partial cDNA for the PSM gene. In this PCR reaction, I and N primers were used. The DNA sequence we obtained when reading from the I primer was:

ACG GAG CAA AAC TTT CAG CTT GCA AAG (SEQ ID No. 30)

T E Q N F Q L A K (SEQ ID No. 31)

The underlined amino acids were the portion of peptide 6 that was used to design this sense primer and the remaining amino acids which agree with those present within our peptide confirm that this end of the molecule represents the correct protein (PSM antigen).

When we analyzed the other end of the molecule by reading from the N primer the sequence was:

CTC TTC GGC ATC CCA GCT TGC AAA CAA AAT TGT TCT (SEQ ID No. 32)

Since this represents the anti-sense DNA sequence, we need to show the complementary sense sequence in order to find our peptide.

Sense Sequence:

AGA ACA ATT TTG TTT GCA AGC TGG GAT GCC AAG GAG (SEQ ID No. 33)

R T I L P A S W D A E E (SEQ ID No. 34)

The underlined amino acids here represent the portion of peptide 7 used to create primer N. All of the amino acids upstream of this primer are correct in the IN-20 clone, agreeing with the amino acids found in peptide 7. Further DNA sequencing has enabled us to identify the presence of our other PSM peptides within the DNA sequence of our positive clone.

The DNA sequence of this partial cDNA was found to be unique when screened on the Genbank computer database.

cDNA Library Construction and Cloning of Full-length PSM cDNA

Figure 7:
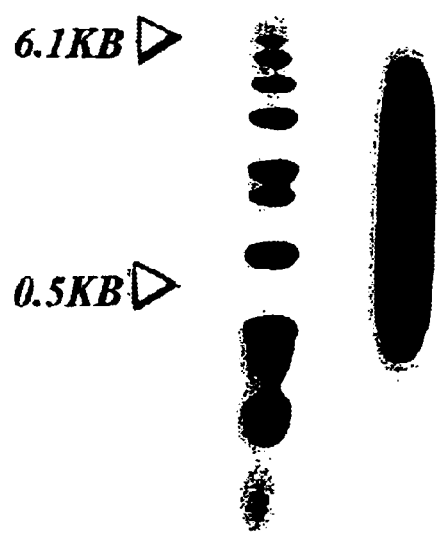
FIG. 7: Autoradiogram showing size of cDNA represented in applicants' LNCaP library using M-MLV reverse transcriptase.
Figure 8:
FIG. 8: Restriction analysis of full-length clones of PSM gene obtained after screening cDNA library. Samples have been cut with NotI and SalI restriction enzymes to liberate the insert.
Figure 9:
FIG. 9: Plasmid Southern autoradiogram of full length PSM gene clones. Size is approximately 2.7 kb.
Figure 10:
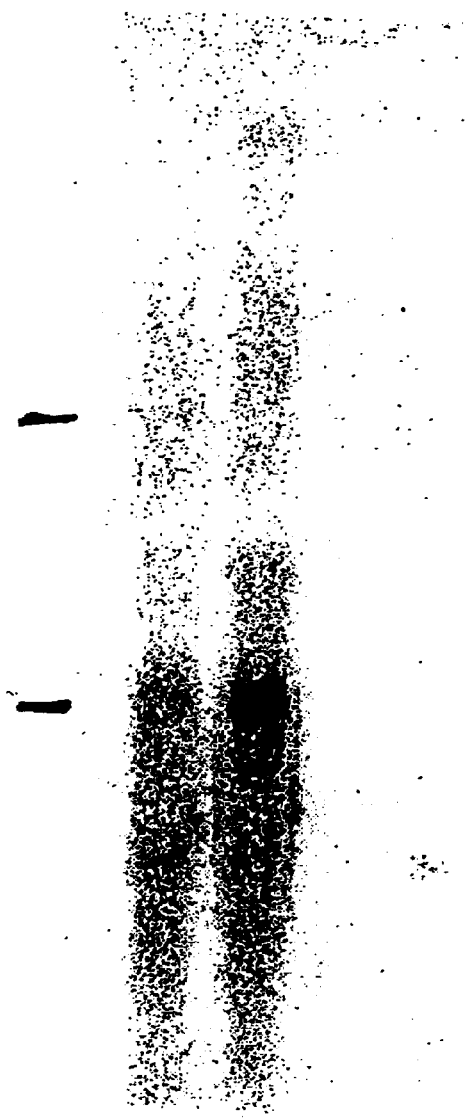
FIG. 10: Northern blot revealing PSM expression limited to LNCaP prostate cancer line and H26 Ras-transfected LNCaP cell line. PC-3, DU-145, T-24, SKRC-27, HELA, MCF-7, HL-60, and others were are all negative.
Figure 11:
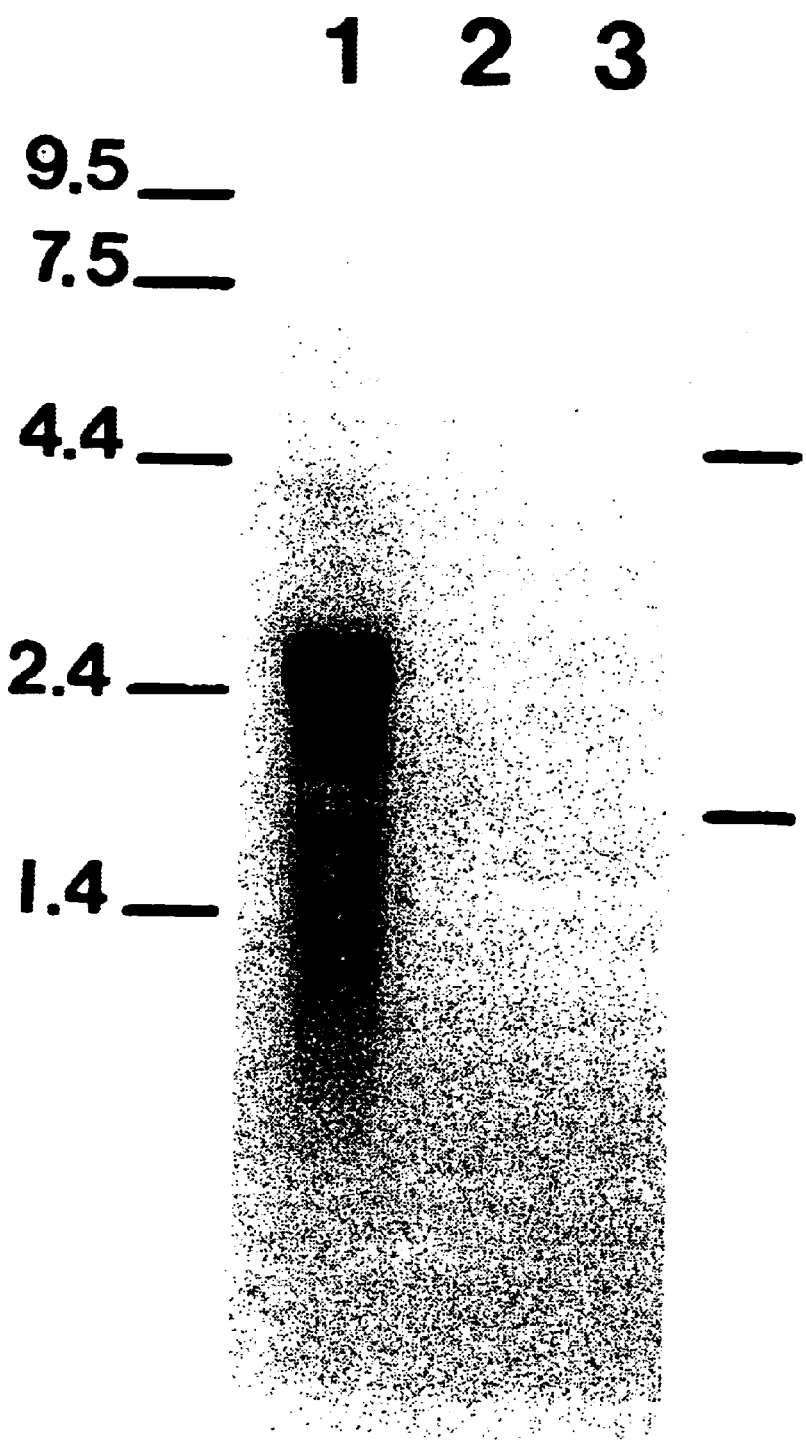
FIG. 11: Autoradiogram of Northern analysis revealing expression of 2.8 kb PSM message unique to the LNCaP cell line (lane 1), and absent from the DU-145 (lane 2) and PC-3 cell lines (lane 3). RNA size ladder is shown on the left (kb), and 28S and 18S ribosomal RNA bands are indicated on the right.
Figure 12:
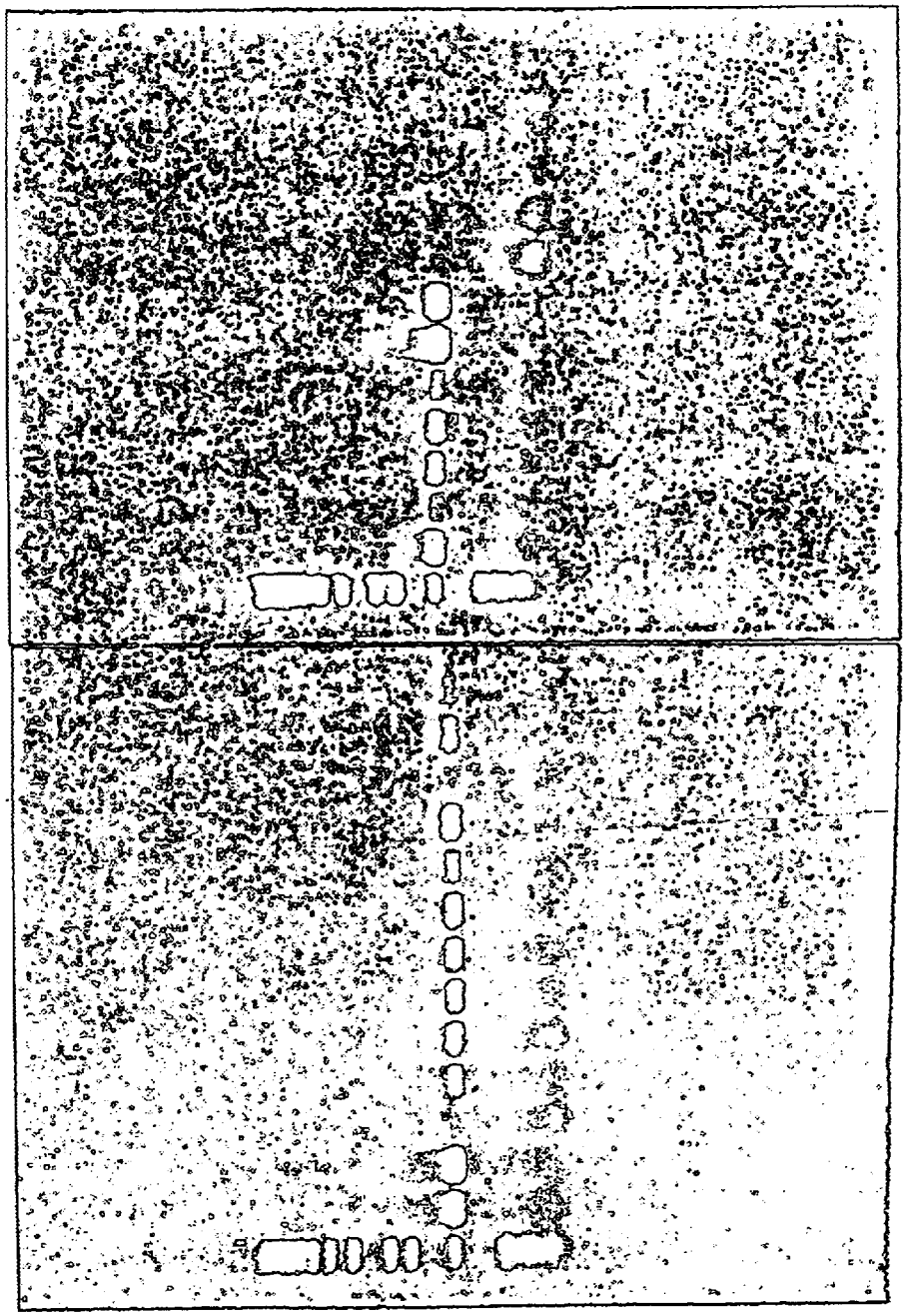
FIG. 12A–B: Results of PCR of human prostate tissues using PSM gene primers. Lanes are numbered from left to right. Lane 1, LNCaP; Lane 2, H26; Lane 3, DU-145; Lane 4, Normal Prostate; Lane 5, BPH; Lane 6, Prostate Cancer; Lane 7, BPH.; Lane 8, Normal; Lane 9, BPH; Lane 10, BPH; Lane 11, BPH; Lane 12, Normal; Lane 13, Normal; Lane 14, Cancer; Lane 15, Cancer; Lane 16, Cancer; Lane 17, Normal; Lane 18, Cancer; Lane 19, IN-20 Control; Lane 20, PSM cDNA
Figure 13:
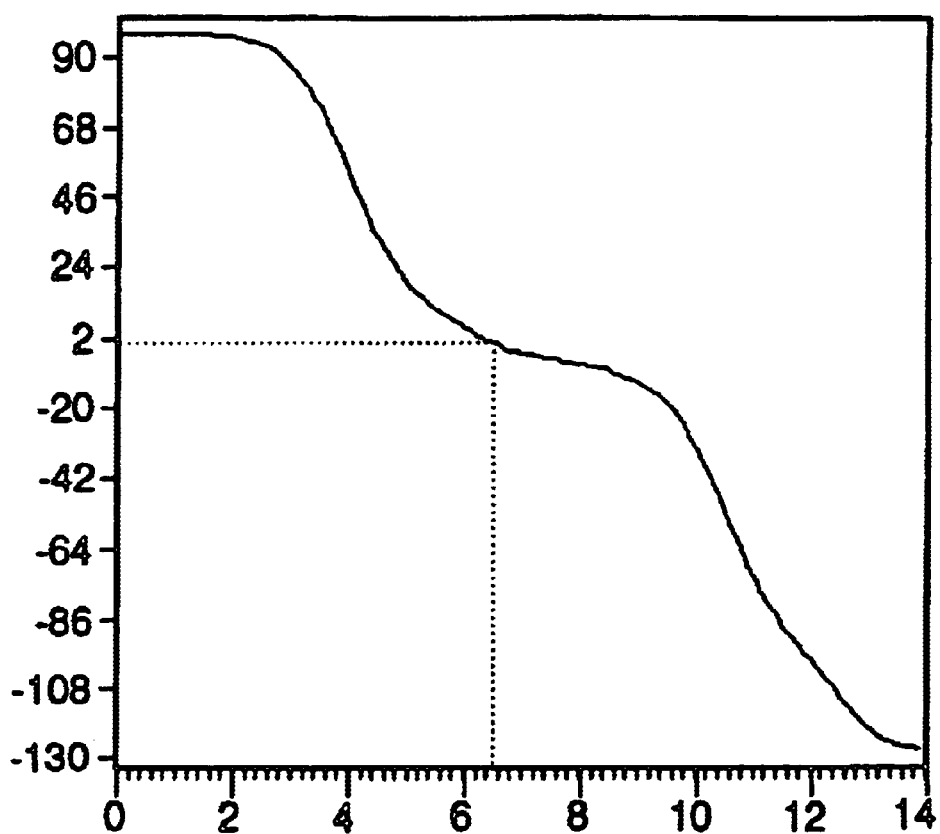
FIG. 13: Isoelectric point of PSM antigen (non-glycosylated)
Figure 15A:
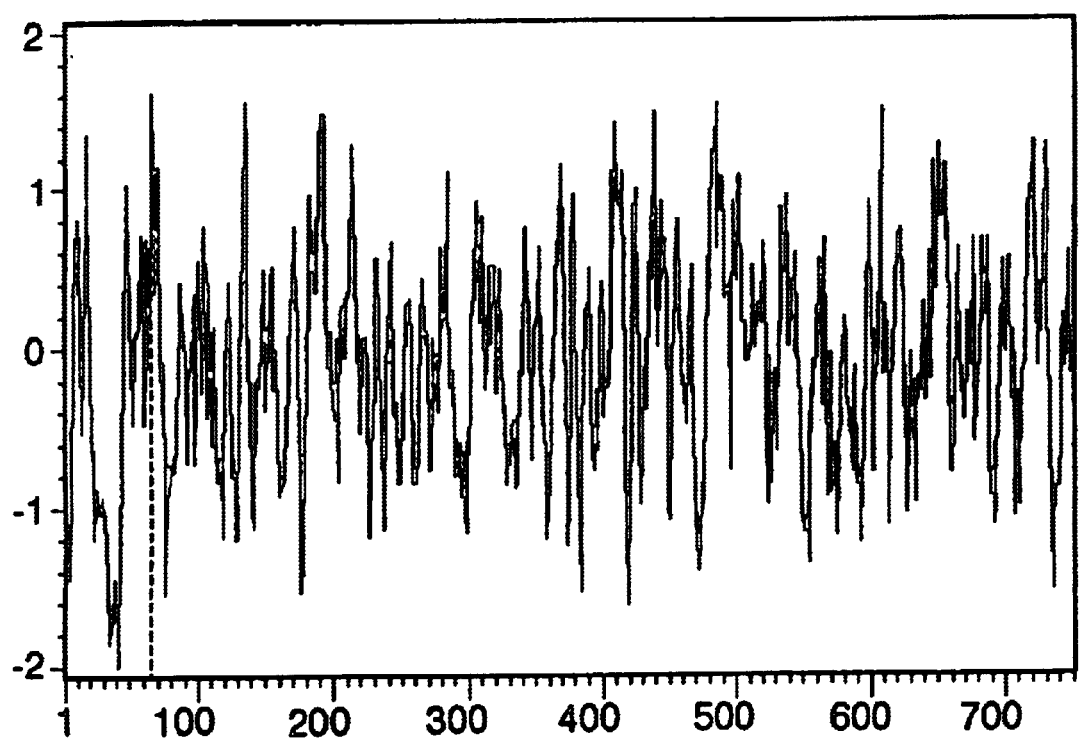
FIG. 15:A–B A. Hydrophilicity plot of PSM antigen B. Prediction of membrane spanning segments (SEQ ID NOS: 35–37).

A cDNA library from LNCaP mRNA was constructed using the Superscript® plasmid system (BRL®-Gibco). The library was transformed using competent DH5-α cells and plated onto 100 mm plates containing LB plus 100 µg/ml of Carbenicillin. Plates were grown overnight at 37° C. and colonies were transferred to nitrocellulose filters. Filters were processed and screened as per Grunstein and Hogness (26), using our 1.1 kb partial cDNA homologous probe which was radiolabelled with $^{32}$P-dCTP by random priming (27). We obtained eight positive colonies which upon DNA restriction and sequencing analysis proved to represent full-length cDNA molecules coding for the PSM antigen. Shown in FIG. 7 is an autoradiogram showing the size of the cDNA molecules represented in our library and in FIG. 8 restriction analysis of several full-length clones is shown. FIG. 9 is a plasmid Southern analysis of the samples in FIG. 8, showing that they all hybridize to the 1.1 kb partial cDNA probe.

Both the cDNA as well as the antigen have been screened through the Genbank Computer database (Human Genome Project) and have been found to be unique.

Northern Analysis of PSM Gene Expression

Northern analysis (28) of the PSM gene has revealed that expression is limited to the prostate and to prostate carcinoma.

RNA samples (either 10 g of total RNA or 2 µg of poly A+ RNA) were denatured and electrophoresed through 1.1% agarose/formaldehyde gels at 60 milliamps for 6–8 hours. RNA was then transferred to Nytran® nylon membranes (Schleicher and Schuell®) by pressure blotting in 10×SSC with a Posi-blotter (Stratagene®). RNA was cross-linked to the membranes using a Stratalinker (Stratagene®) and subsequently baked in a vacuum oven at 80° C. for 2 hours. Blots were pre-hybridized at 65° C. for 2 hours in prehybridization solution (BRL®) and subsequently hybridized for 16 hours in hybridization buffer (BRL®) containing 1–2×10⁶ cpm/ml of $^{32}$P-labelled random-primed cDNA probe. Membranes were washed twice in 1×SSPE/1% SDS and twice in 0.1×SSPE/1% SDS at 42° C. Membranes were then air-dried and autoradiographed for 12–36 hours at −70° C.

PCR Analysis of PSM Gene Expression in Human Prostate Tissues

PCR was performed on IS human prostate samples to determine PSM gene expression. Five samples each from normal prostate tissue, benign prostatic hyperplasia, and prostate cancer were used (histology confirmed by MSKCC Pathology Department).

10 μg of total RNA from each sample was reverse transcribed to made cDNA template as previously described in section IV. The primers used corresponded to the 5' and 3' ends of our 1.1 kb partial cDNA, IN-20, and therefore the expected size of the amplified band is 1.1 kb. Since the $T_m$ of our primers is 64° C. we annealed the primers in our PCR at 60° C. We carried out the PCR for 35 cycles using the same conditions previously described in section IV.

LNCaP and H26—Ras transfected LNCaP (29) were included as a positive control and DU-145 as a negative control. 14/15 samples clearly amplified the 1.1 kb band and therefore express the gene.

Experimental Results

Figure 17A:
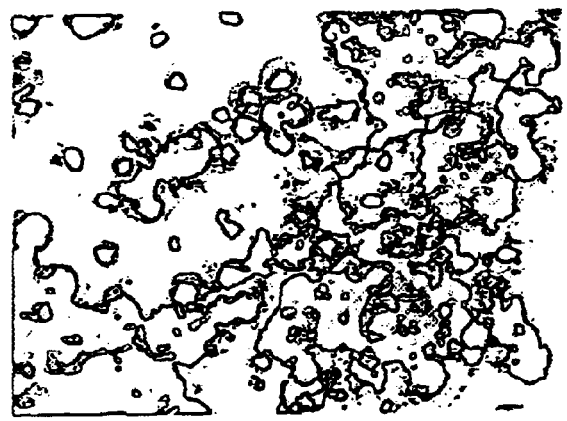
FIG. 17A–C: Immunohistochemical detection of PSM antigen expression in prostate cell lines. Top panel reveals uniformly high level of expression in LNCaP cells; middle panel and lower panel are DU-145 and PC-3 cells respectively, both negative.
Figure 17B:
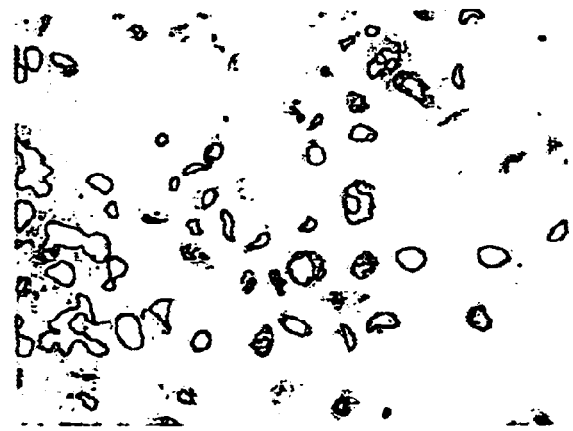
Figure 17C:

The gene which encodes the 100 kD PSM antigen has been identified. The complete cDNA sequence is shown in Sequence ID NO:1. Underneath that nucleic acid sequence is the predicted translated amino acid sequence. The total number of the amino acids is 750, SEQ. ID NO:2. The hydrophilicity of the predicted protein sequence is shown in FIG. 16. Shown in FIG. 17 are three peptides with the highest point of hydrophilicity. They are: Asp-Glu-Leu-Lys-Ala-Glu (SEQ ID No. 35); Asn-Glu-Asp-Gly-Asn-Glu (SEQ ID No. 36; and Lys-Ser-Pro-Asp-Glu-Gly (SEQ ID No. 37).

By the method of Klein, Kanehisa and DeLisi, a specific membrane-spanning domain is identified. The sequence is from the amino acid #19 to amino acid #44: Ala-Gly-Ala-Leu-Val-Leu-Aal-Gly-Gly-Phe-Phe-Leu-Leu-Gly-Phe-Leu-Phe (SEQ ID No. 38).

This predicted membrane-spanning domain was computed on PC Gene (computer software program). This data enables prediction of inner and outer membrane domains of the PSM antigen which aids in designing antibodies for uses in targeting and imaging prostate cancer.

Figure 18:
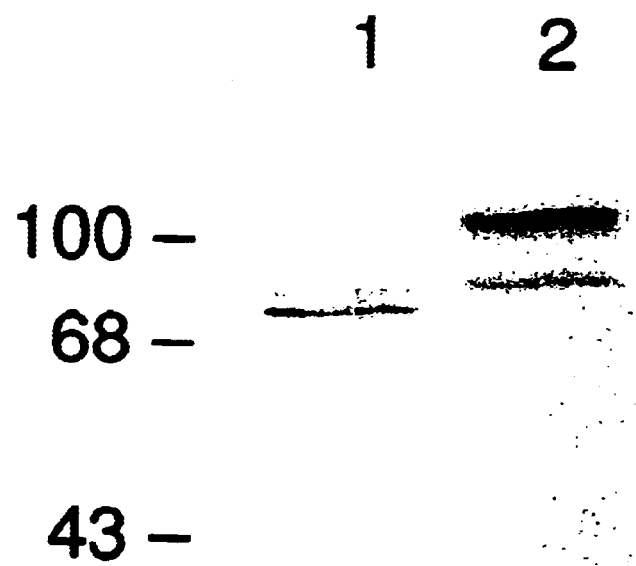
FIG. 18: Autoradiogram of protein gel revealing products of PSM coupled in-vitro transcription/translation. Non-glycosylated PSM polypeptide is seen at 84 kDa (lane 1) and PSM glycoprotein synthesized following the addition of microsomes is seen at 100 kDa (lane 2).

When the PSM antigen sequence with other known sequences of the GeneBank were compared, homology between the PSM antigen sequence and the transferrin receptor sequence were found. The data are shown in FIG. 18.

Experimental Discussions

Potential Uses for PSM Antigen:

1. Tumor Detection:

Microscopic:

Unambiguous tumor designation can be accomplished by use of probes for different antigens. For prostatic cancer, the PSM antigen probe may prove beneficial. Thus PSM could be used for diagnostic purposes and this could be accomplished at the microscopic level using in-situ hybridization using sense (control) and antisense probes derived from the coding region of the cDNA cloned by the applicants. This could be used in assessment of local extraprostatic extension, involvement of lymph node, bone or other metastatic sites. As bone metastasis presents a major problem in prostatic cancer, early detection of metastatic spread is required especially for staging. In some tumors detection of tumor cells in bone marrow portends a grim prognosis and suggests that interventions aimed at metastasis be tried. Detection of PSM antigen expression in bone marrow aspirates or sections may provide such early information. PCR amplification or in-situ hybridization may be used. This could be developed for any possible metastatic region.

2. Antigenic Site Identification

The knowledge of the cDNA for the antigen also provides for the identification of areas that would serve as good antigens for the development of antibodies for use against specific amino acid sequences of the antigen. Such sequences may be at different regions such as outside, membrane or inside of the PSM antigen. The development of these specific antibodies would provide for immunohistochemical identification of the antigen. These derived antibodies could then be developed for use, especially ones that work in paraffin fixed sections as well as frozen section as they have the greatest utility for immunodiagnosis.

3. Restriction Fragment Length Polymorphism and Genomic DNA

Restriction fragment length polymorphisms (RFLPS) have proven to be useful in documenting the progression of genetic damage that occurs during tumor initiation and promotion. It may be that RFLP analysis will demonstrate that changes in PSM sequence restriction mapping may provide evidence of predisposition to risk or malignant potential or progression of the prostatic tumor.

Depending on the chromosomal location of the PSM antigen, the PSM antigen gene may serve as a useful chromosome location marker for chromosome analysis.

4. Serum

With the development of antigen specific antibodies, if the antigen or selected antigen fragments appear in the serum they may provide for a serum marker for the presence of metastatic disease and be useful individually or in combination with other prostate specific markers.

5. Imaging

As the cDNA sequence implies that the antigen has the characteristics of a membrane spanning protein with the majority of the protein on the exofacial surface, antibodies, especially monoclonal antibodies to the peptide fragments exposed and specific to the tumor may provide for tumor imaging local extension of metastatic tumor or residual tumor following prostatectomy or irradiation. The knowledge of the coding region permits the generation of monoclonal antibodies and these can be used in combination to provide for maximal imaging purposes. Because the antigen shares a similarity with the transferrin receptor based on cDNA analysis (approximately 54%), it may be that there is a specific normal ligand for this antigen and that identification of the ligand(s) would provide another means of imaging.

6. Isolation of Ligands

The PSM antigen can be used to isolate the normal ligand(s) that bind to it. These ligand(s) depending on specificity may be used for targeting, or their serum levels may be predictive of disease status. If it is found that the normal ligand for PSM is a carrier molecule then it may be that PSM could be used to bind to that ligand for therapy purposes (like an iron chelating substance) to help remove the ligand from the circulation. If the ligand promotes tumor growth or metastasis then providing soluble PSM antigen would remove the ligand from binding the prostate. Knowledge of PSM antigen structure could lend to generation of small fragment that binds ligand which could serve the same purpose.

7. Therapeutic Uses a) Ligands. The knowledge that the cDNA structure of PSM antigen shares structural homology with the transferrin receptor (54% on the nucleic acid level) implies that there may be an endogenous ligand for the receptor that may or may not be transferrin-like. Transferrin is thought to be a ligand that transports iron into the cell after binding to the transferrin receptor. However, apotransferrin is being reported to be a growth factor for some cells which express the transferrin receptor (30). Whether transferrin is a ligand for this antigen or some other ligand binds to this ligand remains to be determined. If a ligand is identified it may carry a specific substance such as a metal ion (iron or zinc or other) into the tumor and thus serve as a means to deliver toxic substances (radioactive or cytotoxic chemical i.e. toxin like ricin or cytotoxic alkylating agent or cytotoxic prodrug) to the tumor.

The main metastatic site for prostatic tumor is the bone. The bone and bone stroma are rich in transferrin. Recent studies suggest that this microenvironment is what provides the right "soil" for prostatic metastasis in the bone (31). It may be that this also promotes attachment as well, these factors which reduce this ability may diminish prostatic metastasis to the bone and prostatic metastatic growth in the bone.

It was found that the ligand for the new antigen (thought to be an oncogene and marker of malignant phenotype in breast carcinoma) served to induce differentiation of breast cancer cells and thus could serve as a treatment for rather than promotor of the disease. It may be that ligand binding to the right region of PSM whether with natural ligand or with an antibody may serve a similar function.

Antibodies against PSM antigen coupled with a cytotoxic agent will be useful to eliminate prostate cancer cells. Transferrin receptor antibodies with toxin conjugates are cytotoxic to a number of tumor cells as tumor cells tend to express increased levels of transferrin receptor (32). Transferrin receptors take up molecules into the cell by endocytosis. Antibody drug combinations can be toxic. Transferrin linked toxin can be toxic.

b) Antibodies against PSM antigen coupled with a cytotoxic agent will be useful to eliminate prostate cancer cells. The cytotoxic agent may be a radioisotope or toxin as known in ordinary skill of the art. The linkage of the antibody and the toxin or radioisotope can be chemical. Examples of direct linked toxins are doxorubicin, chlorambucil, ricin, *pseudomonas* exotoxin etc., or a hybrid toxin can be generated ½ with specificity for PSM and the other ½ with specificity for the toxin. Such a bivalent molecule can serve to bind to the tumor and the other ½ to deliver a cytotoxic to the tumor or to bind to and activate a cytotoxic lymphocyte such as binding to the $T_1$–$T_3$ receptor complex. Antibodies of required specificity can also be cloned into T cells and by replacing the immunoglobulin domain of the T cell receptor (TcR); cloning in the desired MAb heavy and light chains; splicing the $U_b$ and $U_L$ gene segments with the constant regions of the α and β TCR chains and transfecting these chimeric Ab/TcR genes in the patients' T cells, propagating these hybrid cells and infusing them into the patient (33). Specific knowledge of tissue specific antigens for targets and generation of MAb's specific for such targets will help make this a usable approach. Because the PSM antigen coding region provides knowledge of the entire coding region, it is possible to generate a number of antibodies which could then be used in combination to achieve an additive or synergistic anti-tumor action. The antibodies can be linked to enzymes which can activate non-toxic prodrugs at its site of the tumor such as Ab-carboxypeptidase and 4-(bis(2 chloroethyl)amino) benzoyl-α-glutamic acid and its active parent drug in mice (34).

It is possible to produce a toxic genetic chimera such as TP-40 a genetic recombinant that possesses the cDNA from TGF-alpha and the toxic portion of *pseudomonas* exotoxin so the TGF and portion of the hybrid binds the epidermal growth factor receptor (EGFR) and the *pseudomonas* portion gets taken up into the cell enzymatically and inactivates the ribosomes ability to perform protein synthesis resulting in cell death. When we know the ligand for the PSM antigen we can do the same.

In addition, once the ligand for the PSM antigen is identified, toxin can be chemically conjugated to the ligands. Such conjugated ligands can be therapeutically useful. Examples of the toxins are daunomycin, chlorambucil, ricin, *pseudomonas* exotoxin, etc. Alternatively, chimeric construct can be created linking the cDNA of the ligand with the cDNA of the toxin. An example of such toxin is TGFA and *pseudomonas* exotoxin (35).

8. Others

The PSM antigen may have other uses. It is well known that the prostate is rich in zinc, if the antigen provides function relative to this or other biologic function the PSM antigen may provide for utility in the treatment of other prostatic pathologies such as benign hyperplastic growth and/or prostatitis.

Because purified PSM antigen can be generated, the purified PSM antigen can be linked to beads and use it like a standard "affinity" purification. Serum, urine or other biological samples can be used to incubate with the PSM antigen bound onto beads. The beads may be washed thoroughly and then eluted with salt or pH gradient. The eluted material is SDS gel purified and used as a sample for microsequencing. The sequences will be compared with other known proteins and if unique, the technique of degenerated PCR can be employed for obtaining the ligand. Once known, the affinity of the ligand will be determined by standard protocols (15).

References of the First Series of Experiments

1. Chiaroda, A. (1991) National roundtable of prostate cancer: research directions. Cancer Res. 51: 2498–2505.
2. Coffey, D. S. Prostate Cancer—An overview of an increasing dilemma. Cancer Supplement, 71,3: 880–886, 1993.
3. Warner, J. A., et al., (1991) Future developments of non-hormonal systemic therapy for prostatic carcinoma. Urologic Clin. North Amer. 18:25–33.
4. Nguyen, L., et al., (1990) Prostatic acid phosphatase in the serum of cancer patients with prostatic cancer is a specific phosphotyrosine acid phosphatase. Clin. Chem. 35:1450–1455.
5. Henttu, P., et al., (1989) cDNA coding for the entire human prostate specific antigen show high homologies to the human tissue kallikrein genes. Bioch. Biophys. Res. Comm. 160:903–908.
6. Yong, CY-F., et al., (1991) Hormonal regulation of prostate-specific antigen messenger RNA in human prostatic adenocarcinoma cell line LNCaP. Cancer Res. 51:3748–3752.
7. Liotta, L. A. (1986) Tumor invasion and metastases: role of the extracellular matrix. Cancer Res. 46:1–7.
8. Horoszewicz, J. S., et al. (1987) Monoclonal antibodies to a new antigenic marker in epithelial prostatic cells and serum of prostatic cancer patients. Anticancer Res. 7:927–936.
9. Horoszewicz, J. S., et al. (1983) LNCaP model of human prostatic carcinoma. Cancer Res., 43:1809–1818.
10. Lopes, D., et al. (1990) Immunohistochemical and pharmacokinetic characterization of the site-specific immunoconjugate CYT-356, derived from anti-prostate monoclonal antibody 7E11-C5. Cancer Res., 50:6423–6429.

11. Wright, Jr., et al., (1990) Characterization of a new carcinoma associated marker: 7E11-C5. Antibod. Immunoconj. Radiopharm. 3:(abst #193).

12. Feng, Q., et al., (1991) Purification and biochemical characterization of the 7E11-C5 prostate carcinoma associated antigen. Proc. Amer. Assoc. Cancer Res. 32:239.

13. Axelrod, H. R., et al., Preclinical results and human immunohistochemical studies with $^{90}$Y-CYT-356. A New prostate cancer agent. Abstract 596. AUA 87th Annual Meeting, May 10–14, 1992. Washington, D.C.

14. Maniatis, T., et al., (1982) Molecular Cloning; Cold Spring Harbor Laboratory, pp. 197–98 (1982).

15. Maniatis, et al., (1982) Molecular Cloning, Cold Spring Harbor Laboratory.

16. Methods in Enzymology vol. 34: 1–810, 1974 (E) B. Jacoby and M. Wilchek Academic Press, New York 1974.

17. Hogan B. et al. (1986) Manipulating the Mouse Embryo, A Laboratory Manual, Cold Spring Harbor Laboratory.

18. Capecchi M. R. Science (1989) 244:1288–1292; Zimmer, A. and Gruss, P. (1989) Nature 33B:150–153.

19. Trowbridge, I. S., (1982) Prospects for the clinical use of cytotoxic monoclonal antibodies conjugates in the treatment of cancer. Cancer Surveys 1:543–556.

20. Hank, S. K. (1987) Homology probing: Identification of cDNA clones encoding members of the protein-serine kinase family. Proc. Natl. Acad. Sci. 84:388–392.

21. Lee, C. C., et al., (1989) Generation of cDNA probes directed by amino acid sequences: cloning of urate oxidase. Science, 239, 1288.

22. Girgis, S. I., et al. (1988) Generation of DNA probes for peptides with highly degenerate codons using mixed primer PCR. Nucleic Acids Res. 16:10932.

23. Kartner, N., et al. (1977) Isolation of plasma membranes from human skin fibroblasts. J. Membrane Biology, 36:191–211.

24. Hsu, S. M., et al. (1981) Comparative study of the immunoperoxidase, anti-peroxidase, and avidin-biotin complex method for studying polypeptide hormones with radioimmunoassay antibodies. Am. J. Pathology, 75:734.

25. Tempst, P., et al. (1989) Examination of automated polypeptide sequencing using standard phenylisothiocyanate reagent and subpicomole high performance liquid chromatography analysis. Analytical Biochem. 183:290–300.

26. Birnboim, H. C. (1983) A rapid alkaline extraction method for the isolation of plasmid DNA. Meth. Enzymol, 100:243–255.

27. Sanger, F., et al. (1977) DNA sequencing with chain-terminating inhibitors. Proc. Natl. Acad. Sci. USA, 74:5463–5467.

28. Grunstein, M., et al. (1975) Colony hybridization as a method for the isolation of cloned DNAs that contain a specific gene. Proc. Natl. Acad. Sci. USA, 72:3961.

29. Feinberg, A. P., et al. (1983) A technique for radiolabeling DNA restriction endonuclease fragments to high specific activity. Anal. Biochem, 132, 6.

30. Rave, N., et al. (1979) Identification of procollagen mRNAs transferred to diazobenzylomethyl paper from formaldehyde gels. Nucleic Acids Research, 6:3559.

31. Voeller, H. J., et al. (1991) v-ras$^H$ expression confers hormone-independent in-vitro growth to LNCaP prostate carcinoma cells. Molec. Endocrinology. Vol. 5. No. 2, 209–216.

32. Sirbasku, D. A. (1991) Purification of an equine apotransferrin variant (thyromedin) essential for thyroid hormone dependent growth of $GH_1$, rat pituitary tumor cells in chemically defined culture. Biochem., 30:295–301.

33. Rossi, M. C. (1992) Selective stimulation of prostatic carcinoma cell proliferation by transferrin. Proc. Natl. Acad. Sci. (USA) 89:6197–6201.

34. Eshhan, Z. (1990) Chimeric T cell receptor which incorporates the anti-tumor specificity of a monoclonal antibody with the cytolytic activity of T cells: a model system for immunotherapeutic approach. B. J. Cancer 62:27–29.

35. Antonie, P. (1990) Disposition of the prodrug 4-(bis(2 chloroethyl)amino)benzoyl-α-glutamic acid and its active parent in mice. B. J. Cancer 62:905–914.

36. Heimbrook, D. C., et al. (1990) Transforming growth factor alpha-*pseudomonas* exotoxin fusion protein prolongs survival of nude mice bearing tumor xenografts. Proc. Natl. Acad. Sci. (USA) 87:4697–4701.

37. Chiarodo., A. National Cancer Institute roundtable on prostate cancer; future research directions. Cancer Res., 51: 2498–2505, 1991.

38. Abdel-Nabi, H., Wright, G. L., Gulfo, J. V., Petrylak, D. P., Neal, C. E., Texter, J. E., Begun, F. P., Tyson, I., Heal, A., Mitchell, E., Purnell, G., and Harwood, S. J. Monoclonal antibodies and radioimmunoconjugates in the diagnosis and treatment of prostate cancer. Semin. Urol., 10: 45–54, 1992.

Second Series of Experiments

Expression of the Prostate-specific Membrane Antigen

Applicant's have recently cloned a 2.65 kb complementary DNA encoding PSM, the prostate-specific membrane antigen recognized by the 7E11-C5.3 anti-prostate monoclonal antibody. Immunohistochemical analysis of the LNCaP, DU-145, and PC-3 prostate cancer cell lines for PSM expression using the 7E11-C5.3 antibody reveals intense staining in the LNCaP cells, with no detectable expression in both the DU-145 and PC-3 cells. Coupled in-vitro transcription/translation of the 2.65 kb full-length PSM cDNA yields an 84 kDa protein corresponding to the predicted polypeptide molecular weight of PSM. Post-translational modification of this protein with pancreatic canine microsomes yields the expected 100 kDa PSM antigen. Following transfection of PC-3 cells with the full-length PSM cDNA in a eukaryotic expression vector applicant's detect expression of the PSM glycoprotein by Western analysis using the 7E11-C5.3 monoclonal antibody. Ribonuclease protection analysis demonstrates that the expression of PSM mRNA is almost entirely prostate-specific in human tissues. PSM expression appears to be highest in hormone-deprived states and is hormonally modulated by steroids, with DHT downregulating PSM expression in the human prostate cancer cell line LNCaP by 8–10 fold, testosterone downregulating PSM by 3–4 fold, and corticosteroids showing no significant effect. Normal and malignant prostatic tissues consistently show high PSM expression, whereas we have noted heterogeneous, and at times absent, expression of PSM in benign prostatic hyperplasia. LNCaP tumors implanted and grown both orthotopically and subcutaneously in nude mice, abundantly express PSM providing an excellent in-vivo model system to study the regulation and modulation of PSM expression.

Experimental Details

Materials and Methods

Cells and Reagents:

The LNCaP, DU-145, and PC-3 cell lines were obtained from the American Type Culture Collection. Details regarding the establishment and characteristics of these cell lines have been previously published (5A,7A,8A). Unless specified otherwise, LNCaP cells were grown in RPMI 1640 media supplemented with L-glutamine, nonessential amino acids, and 5% fetal calf serum (Gibco-BRL, Gaithersburg, Md.) in a $CO_2$ incubator at 37 C. DU-145 and PC-3 cells were grown in minimal essential medium supplemented with 10% fetal calf serum. All cell media were obtained from the MSKCC Media Preparation Facility. Restriction and modifying enzymes were purchased from Gibco-BRL unless otherwise specified.

Immunohistochemical Detection of PSM

We employed the avidin-biotin method of detection to analyze prostate cancer cell lines for PSM antigen expression (9A) Cell cytospins were made on glass slides using $5\times10^4$ cells/100 ul per slide. Slides were washed twice with PBS and then incubated with the appropriate suppressor serum for 20 minutes. The suppressor serum was drained off and the cells were incubated with diluted 7E11-C5.3 (5 g/ml) monoclonal antibody for 1 hour. Samples were then washed with PBS and sequentially incubated with secondary antibodies for 30 minutes and with avidin-biotin complexes for 30 minutes. Diaminobenzidine served as our chromogen and color development followed by hematoxylin counterstaining and mounting. Duplicate cell cytospins were used as controls for each experiment. As a positive control, the anti-cytokeratin monoclonal antibody CAM 5.2 was used following the same procedure described above. Human EJ bladder carcinoma cells served as a negative control.

In-vitro Transcription/Translation of PSM Antigen

Plasmid 55A containing the full length 2.65 kb PSM cDNA in the plasmid pSPORT 1 (Gibco-BRL) was transcribed in-vitro using the Promega TNT system (Promega Corp. Madison, Wis.). T7 RNA polymerase was added to the cDNA in a reaction mixture containing rabbit reticulocyte lysate, an amino acid mixture lacking methionine, buffer, and $^{35}$S-Methionine (Amersham) and incubated at 30 C for 90 minutes. Post-translational modification of the resulting protein was accomplished by the addition of pancreatic canine microsomes into the reaction mixture (Promega Corp. Madison, Wis.). Protein products were analyzed by electrophoresis on 10o SDS-PAGE gels which were subsequently treated with Amplify autoradiography enhancer (Amersham, Arlington Heights, Ill.) according to the manufacturers instructions and dried at 80 C in a vacuum dryer. Gels were autoradiographed overnight at −70 C using Hyperfilm MP (Amersham).

Transfection of PSM into PC-3 Cells

The full length PSM cDNA was subcloned into the pREP7 eukaryotic expression vector (Invitrogen, San Diego, Calif.). Plasmid DNA was purified from transformed DH5-alpha bacteria (Gibco-BRL) using Qiagen maxi-prep plasmid isolation columns (Qiagen Inc., Chatsworth, Calif.). Purified plasmid DNA (6–10 g) was diluted with 900 ul of Optimem media (Gibco-BRL) and mixed with 30 ul of Lipofectin reagent (Gibco-BRL) which had been previously diluted with 900 l of Optimem media. This mixture was added to T-75 flasks of 40–50% confluent PC-3 cells in Optimem media. After 24–36 hours, cells were trypsinized and split into 100 mm dishes containing RPMI 1640 media supplemented with 10% fetal calf serum and 1 mg/ml of Hygromycin B (Calbiochem, La Jolla, Calif.). The dose of Hygromycin B used was previously determined by a time course/dose response cytotoxicity assay. Cells were maintained in this media for 2–3 weeks with changes of media and Hygromycin B every 4–5 days until discrete colonies appeared. Colonies were isolated using 6 mm cloning cylinders and expanded in the same media. As a control, PC-3 cells were also transfected with the pREP7 plasmid alone. RNA was isolated from the transfected cells and PSM mRNA expression was detected by both RNase Protection analysis (described later) and by Northern analysis.

Western Blot Detection of PSM Expression

Crude protein lysates were isolated from LNCaP, PC-3, and PSM-transfected PC-3 cells as previously described (10A). LNCaP cell membranes were also isolated according to published methods (10A). Protein concentrations were quantitated by the Bradford method using the BioRad protein reagent kit (BioRad, Richmond, Calif.). Following denaturation, 20 g of protein was electrophoresed on a 10% SDS-PAGE gel at 25 mA for 4 hours. Gels were electroblotted onto Immobilon P membranes (Millipore, Bedford, Mass.) overnight at 4 C. Membranes were blocked in 0.15M NaCl/0.01M Tris-HCl (TS) plus 5% BSA followed by a 1 hour incubation with 7E11-C5.3 monoclonal antibody (10 g/ml). Blots were washed 4 times with 0.15M NaCl/0.01M Tris-HCl/0.05% Triton-X 100 (TS-X) and incubated for 1 hour with rabbit anti-mouse IgG (Accurate Scientific, Westbury, N.Y.) at a concentration of 10 g/ml.

Blots were then washed 4 times with TS-X and labeled with $^{125}$I-Protein A (Amersham, Arlington Heights, Ill.) at a concentration of 1 million cpm/ml. Blots were then washed 4 times with TS-X and dried on Whatman 3 mM paper, followed by overnight autoradiography at −70 C using Hyperfilm MP (Amersham).

Orthotopic and Subcutaneous LNCaP Tumor Growth in Nude Mice

LNCaP cells were harvested from sub-confluent cultures by a one minute exposure to a solution of 0.25% trypsin and 0.02% EDTA. Cells were resuspended in RPMI 1640 media with 5% fetal bovine serum, washed and diluted in either Matrigel (Collaborative Biomedical Products, Bedford, Mass.) or calcium and magnesium-free Hank's balanced salt solution (HBSS). Only single cell suspensions with greater than 90% viability by trypan blue exclusion were used for in vivo injection. Male athymic Swiss (nu/nu) nude mice 4–6 weeks of age were obtained from the Memorial Sloan-Kettering Cancer Center Animal Facility. For subcutaneous tumor cell injection one million LNCaP cells resuspended in 0.2 mls. of Matrigel were injected into the hindlimb of each mouse using a disposable syringe fitted with a 28 gauge needle. For orthotopic injection, mice were first anesthetized with an intraperitoneal injection of Pentobarbital and placed in the supine position. The abdomen was cleansed with Betadine and the prostate was exposed through a midline incision. 2.5 million LNCaP tumor cells in 0.1 ml. were injected directly into either posterior lobe using a 1 ml disposable syringe and a 28 gauge needle. LNCaP cells with and without Matrigel were injected. Abdominal closure was achieved in one layer using Autoclip wound clips (Clay Adams, Parsippany, N.J.). Tumors were harvested in 6–8 weeks, confirmed histologically by faculty of the Memorial Sloan-Kettering Cancer Center Pathology Department, and frozen in liquid nitrogen for subsequent RNA isolation.

RNA Isolation

Total cellular RNA was isolated from cells and tissues by standard techniques (11,12) as well as by using RNAzol B (Cinna/Biotecx, Houston, Tex.). RNA concentrations and quality were assessed by UV spectroscopy on a Beckman DU 640 spectrophotometer and by gel analysis. Human tissue total RNA samples were purchased from Clontech Laboratories, Inc., Palo Alto, Calif.

Ribonuclease Protection Assays

A portion of the PSM cDNA was subcloned into the plasmid vector pSPORT 1 (Gibco-BRL) and the orientation of the cDNA insert relative to the flanking T7 and SP6 RNA polymerase promoters was verified by restriction analysis. Linearization of this plasmid upstream of the PSM insert followed by transcription with SP6 RNA polymerase yields a 400 nucleotide antisense RNA probe, of which 350 nucleotides should be protected from RNase digestion by PSM RNA. This probe was used in FIG. 20. Plasmid IN-20, containing a 1 kb partial PSM cDNA in the plasmid pCR II (Invitrogen) was also used for riboprobe synthesis. IN-20 linearized with XmnI (Gibco-BRL) yields a 298 nucleotide anti-sense RNA probe when transcribed using SP6 RNA polymerase, of which 260 nucleotides should be protected from RNase digestion by PSM mRNA. This probe was used in FIGS. 21 and 22. Probes were synthesized using SP6 RNA polymerase (Gibco-BRL), rNTPs (Gibco-BRL), RNAsin (Promega), and $^{32}$P-rCTP (NEN, Wilmington, Del.) according to published protocols (13). Probes were purified over NENSORB 20 purification columns (NEN) and approximately 1 million cpm of purified, radiolabeled PSM probe was mixed with 10 g of each RNA and hybridized overnight at 45 C using buffers and reagents from the RPA II kit (Ambion, Austin, Tex.). Samples were processed as per manufacturer's instructions and analyzed on 5% polyacrilamide/7M urea denaturing gels using Seq ACRYL reagents (ISS, Natick, Mass.). Gels were pre-heated to 55 C and run for approximately 1–2 hours at 25 watts. Gels were then fixed for 30 minutes in 10% methanol/10% acetic acid, dried onto Whatman 3 mM paper at 80 C in a BioRad vacuum dryer and autoradiographed overnight with Hyperfilm MP (Amersham). Quantitation of PSM expression was determined by using a scanning laser densitometer (LKB, Piscataway, N.J.).

Steroid Modulation Experiment

LNCaP cells (2 million) were plated onto T-75 flasks in RPMI 1640 media supplemented with 5% fetal calf serum and grown 24 hours until approximately 30–40% confluent. Flasks were then washed several times with phophate-buffered saline and RPMI medium supplemented with 5% charcoal-extracted serum was added. Cells were then grown for another 24 hours, at which time dihydrotesterone, testosterone, estradiol, progesterone, and dexamethasone (Steraloids Inc., Wilton, N.H.) were added at a final concentration of 2 nM. Cells were grown for another 24 hours and RNA was then harvested as previously described and PSM expression analyzed by ribonuclease protection analysis.

Experimental Results
Immunohistochmical Detection of PSK:

Using the 7E11-C5.3 anti-PSM monoclonal antibody, PSM expression is clearly detectable in the LNCaP prostate cancer cell line, but not in the PC-3 and DU-145 cell lines (FIG. 17) in agreement with previously published results (4A). All normal and malignant prostatic tissues analyzed stained positively for PSM expression (unpublished data).

In-vitro Transcription/Translation of PSK Antigen:

As shown in FIG. 18, coupled in-vitro transcription/translation of the 2.65 kb full-length PSM cDNA yields an 84 kDa protein species in agreement with the expected protein product from the 750 amino acid PSM open reading frame. Following post-translational modification using pancreatic canine microsomes we obtained a 100 kDa glycosylated protein species consistent with the mature, native PSM antigen.

Figure 19:
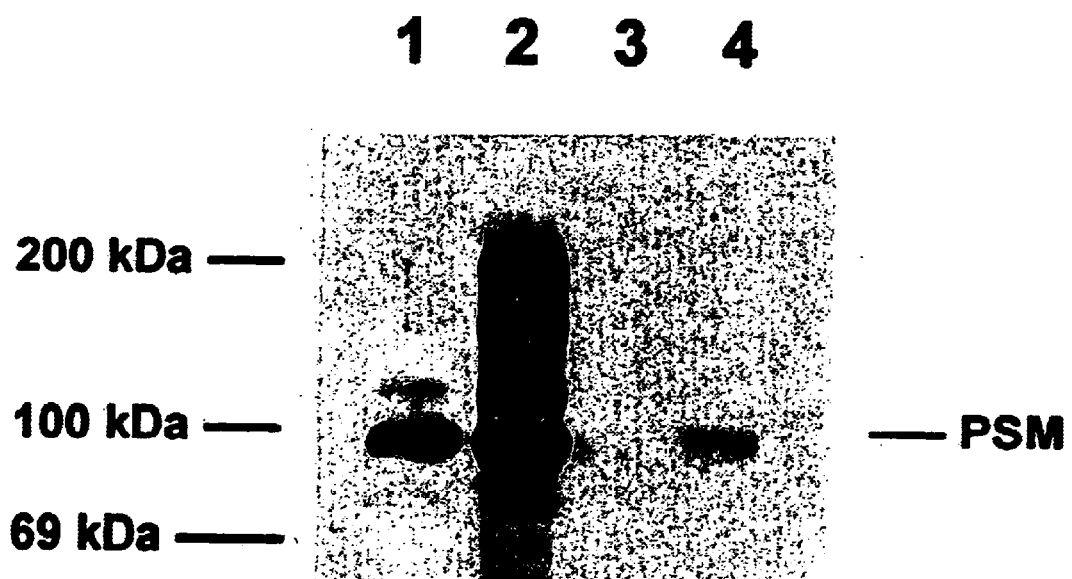
FIG. 19: Western Blot analysis detecting PSM expression in transfected non-PSM expressing PC-3 cells. 100 kDa PSM glycoprotein species is clearly seen in LNCaP membranes (lane 1), LNCaP crude lysate (lane 2), and PSM-transfected PC-3 cells (lane 4), but is undetectable in native PC-3 cells (lane 3).

Detection of PSM Antigen in LNCaP Cell Membranes and Transfected PC-3 Cells:

PC-3 cells transfected with the full length PSM cDNA in the pREP7 expression vector were assayed for expression of SM mRNA by Northern analysis (data not shown). A clone with high PSM mRNA expression was selected for PSM antigen analysis by Western blotting using the 7E11-C5.3 antibody. In FIG. 19, the 100 kDa PSM antigen is well expressed in LNCaP cell lysate and membrane fractions, as well as in PSM-transfected PC-3 cells but not in native PC-3 cells. This detectable expression in the transfected PC-3 cells proves that the previously cloned 2.65 kb PSM cDNA encodes the antigen recognized by the 7E11-C5.3 anti-prostate monoclonal antibody and that the antigen is being appropriately glycosylated in the PC-3 cells, since the antibody recognizes a carbohydrate-containing epitope on PSM.

Figure 20:
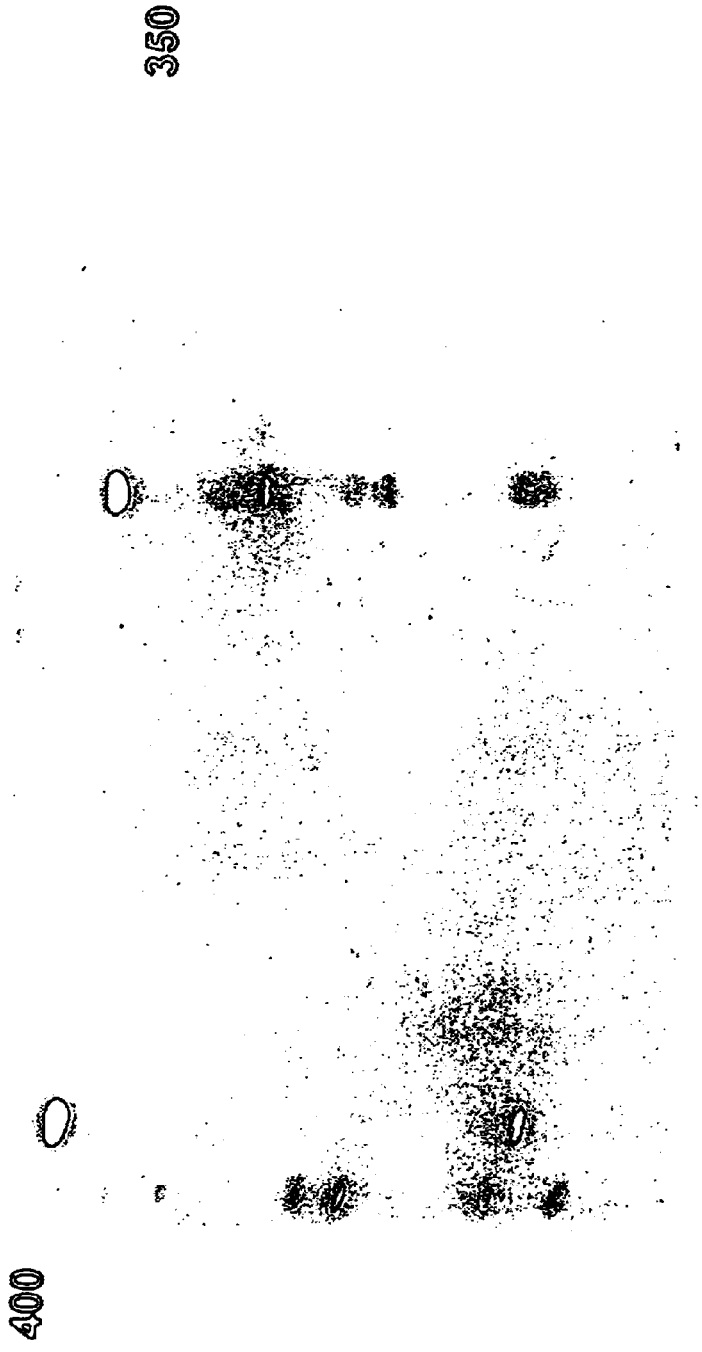
FIG. 20: Autoradiogram of ribonuclease protection gel assaying for PSM mRNA expression in normal human tissues. Radiolabeled 1 kb DNA ladder (Gibco-BRL) is shown in lane 1. Undigested probe is 400 nucleotides (lane 2), expected protected PSM band is 350 nucleotides, and tRNA control is shown (lane 3). A strong signal is seen in human prostate (lane 11), with very faint, but detectable signals seen in human brain (lane 4) and human salivary gland (lane 12).
Figure 21:
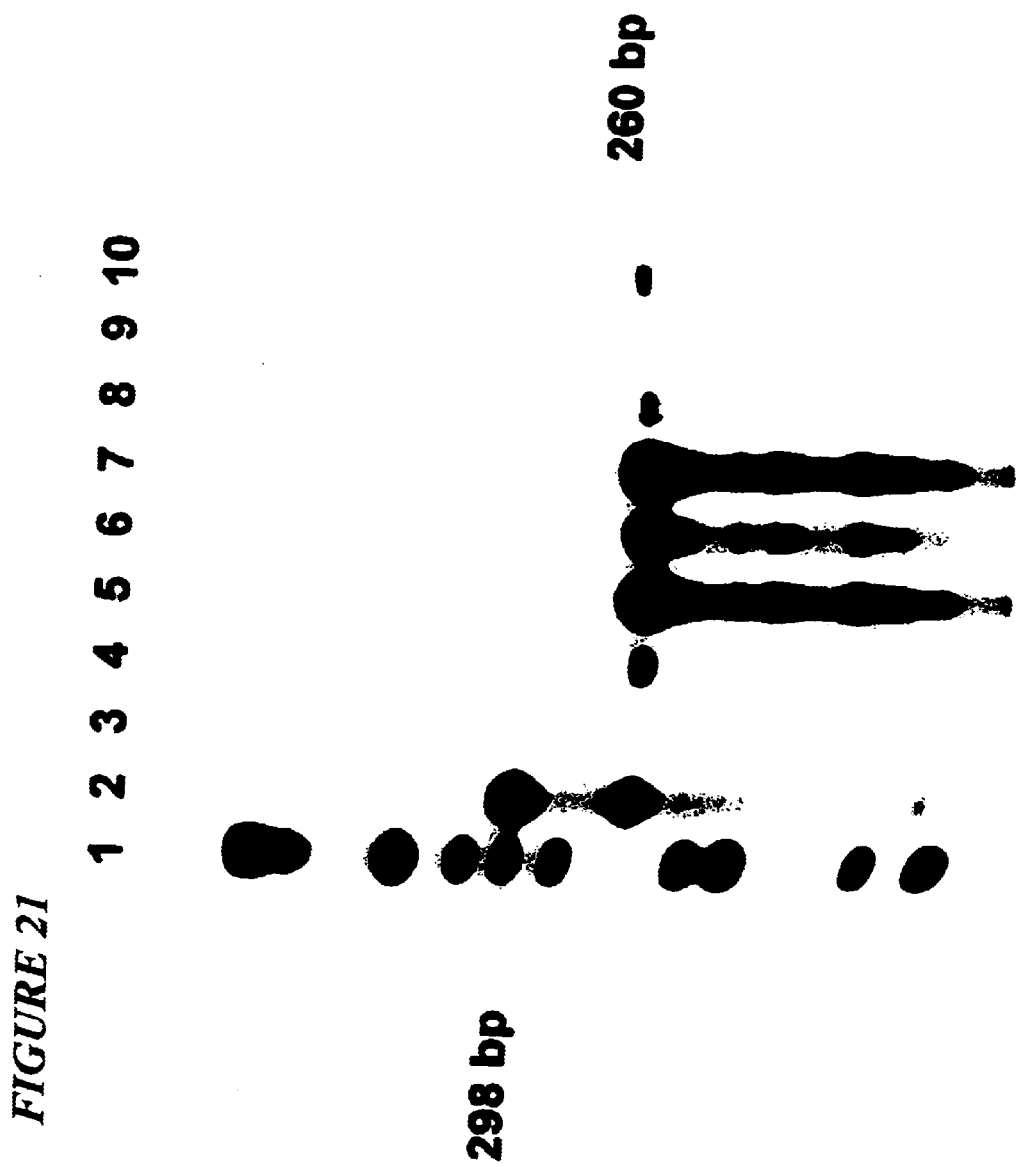
FIG. 21: Autoradiogram of ribonuclease protection gel assaying for PSM mRNA expression in LNCaP tumors grown in nude mice, and in human prostatic tissues. $^{32}$P-labeled 1 kb DNA ladder is shown in lane 1. 298 nucleotide undigested probe is shown (lane 2), and tRNA control is shown (lane 3). PSM mRNA expression is clearly detectable in LNCaP cells (lane 4), orthotopically grown LNCaP tumors in nude mice with and without matrigel (lanes 5 and 6), and subcutaneously implanted and grown LNCaP tumors in nude mice (lane 7). PSM mRNA expression is also seen in normal human prostate (lane 8), and in a moderately differentiated human prostatic adenocarcinoma (lane 10). Very faint expression is seen in a sample of human prostate tissue with benign hyperplasia (lane 9).
Figure 22:
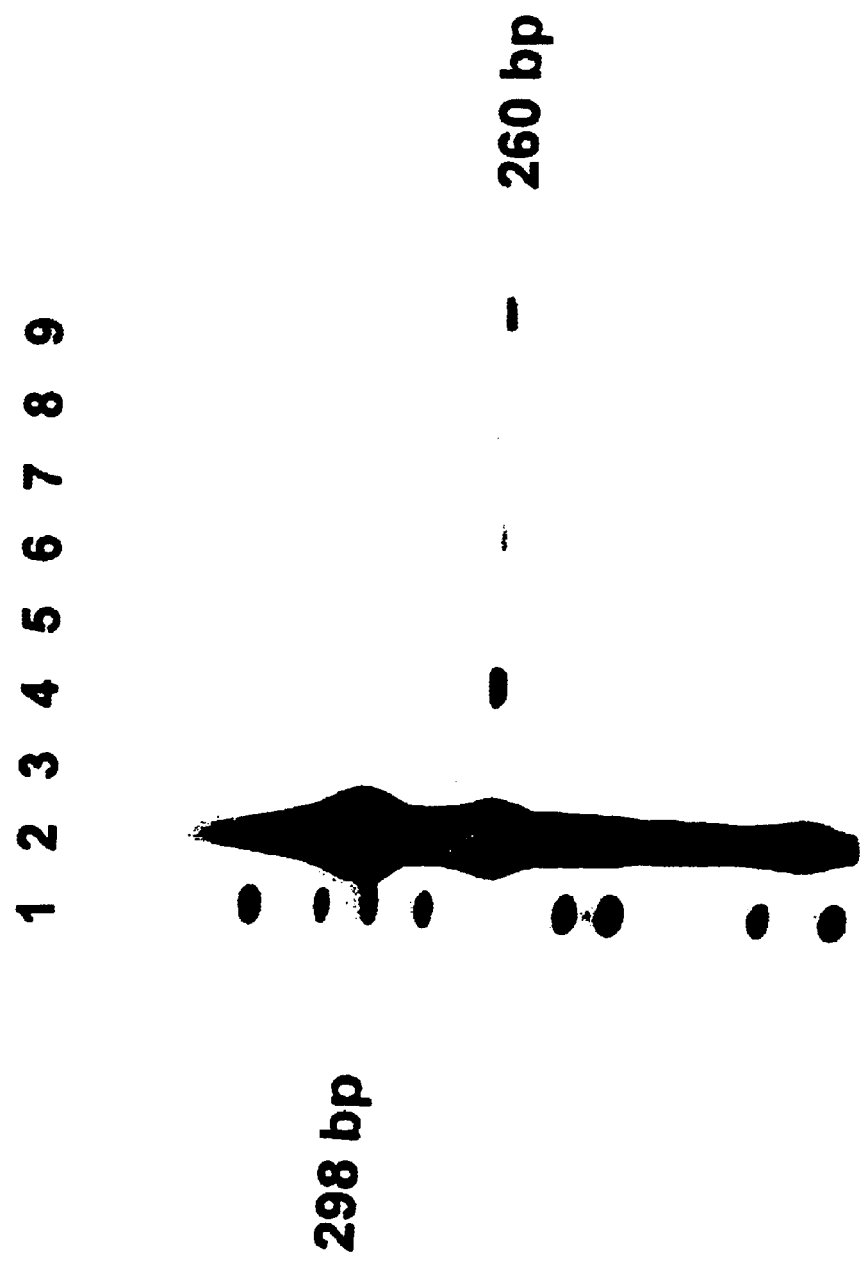
FIG. 22: Ribonuclease protection assay for PSM expression in LNCaP cells treated with physiologic doses of various steroids for 24 hours. $^{32}$P-labeled DNA ladder is shown in lane 1. 298 nucleotide undigested probe is shown (lane 2), and tRNA control is shown (lane 3). PSM mRNA expression is highest in untreated LNCaP cells in charcoal-stripped media (lane 4). Applicant see significantly diminished PSM expression in LNCaP cells treated with DHT (lane 5), Testosterone (lane 6), Estradiol (lane 7), and Progesterone (lane 8), with little response to Dexamethasone (lane 9).
Figure 24A:
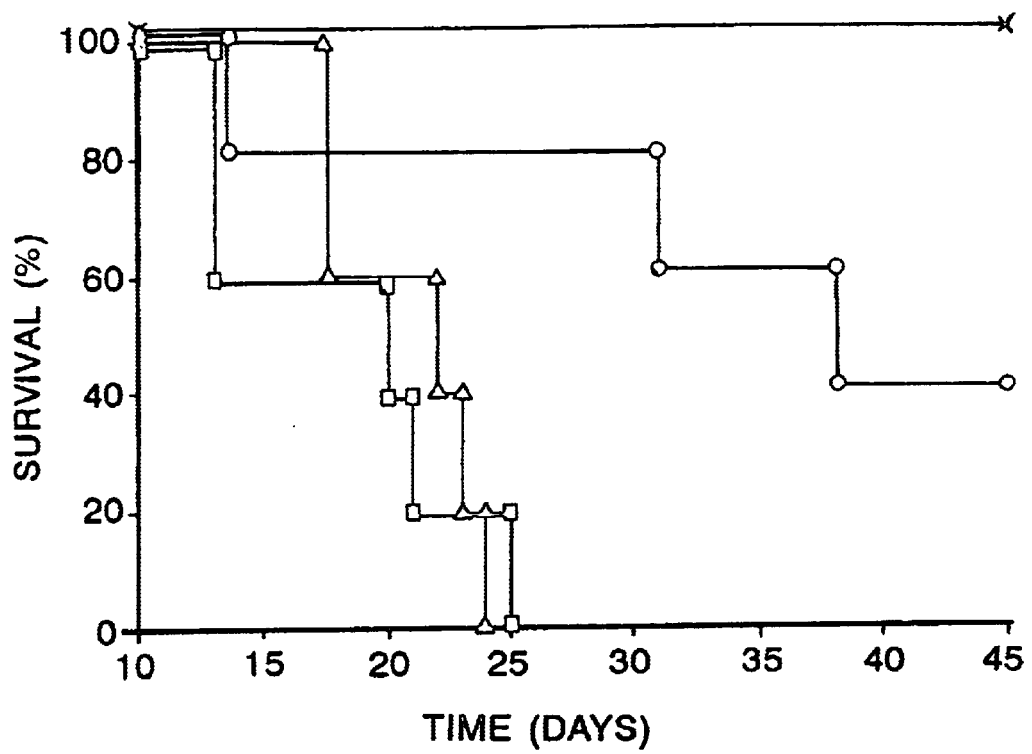
Figure 24B:
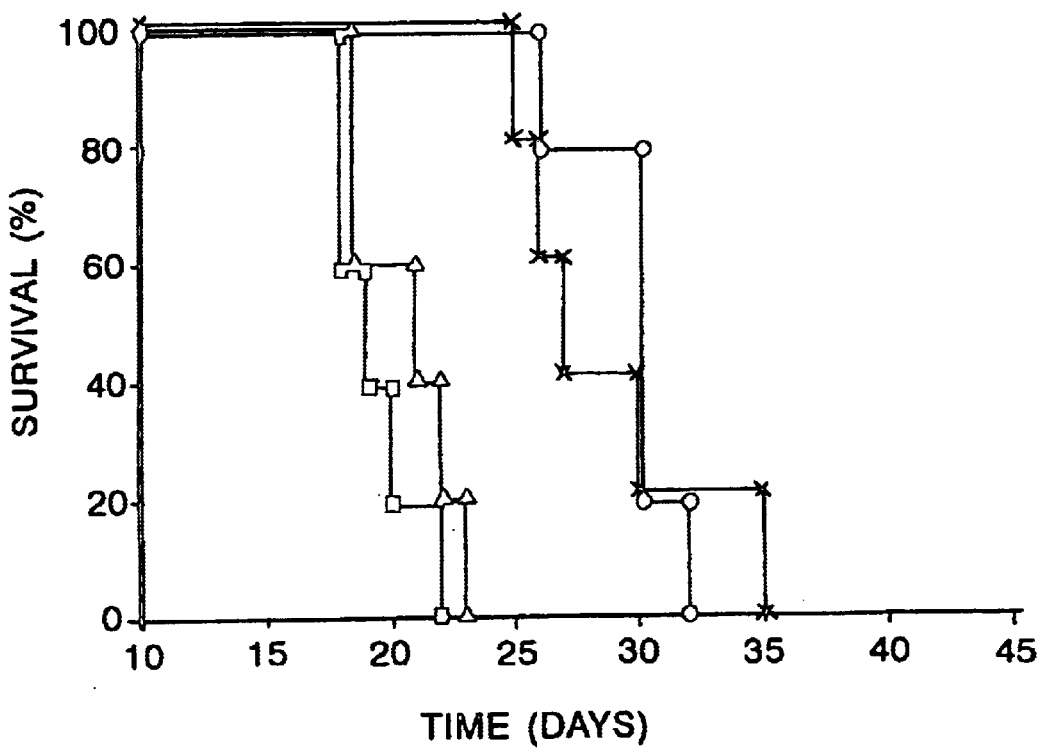

PSM mRNA Expression:

Expression of PSM mRNA in normal human tissues was analyzed using ribonuclease protection assays. Tissue expression of PSM appears predominantly within the prostate, with very low levels of expression detectable in human brain and salivary gland (FIG. 20). No detectable PSM mRNA expression was evident in non-prostatic human tissues when analyzed by Northern analysis (data not shown). We have also noted on occasion detectable PSM expression in normal human small intestine tissue, however this mRNA expression is variable depending upon the specific riboprobe used (data not shown). All samples of normal human prostate and human prostatic adenocarcinoma assayed have revealed clearly detectable PSM expression, whereas we have noted generally decreased or absent expression of PSM in tissues exhibiting benign hyperplasia (FIG. 21). In human LNCaP tumors grown both orthotopically and subcutaneously in nude mice we detected abundant PSM expression with or without the use of matrigel, which is required for the growth of subcutaneously implanted LNCaP cells (FIG. 21). PSM mRNA expression is distinctly modulated by the presence of steroids in physiologic doses (FIG. 22). DHT downregulated expression by 8–10 fold after 24 hours and testosterone diminished PSM expression by 3–4 fold. Estradiol and progesterone also downregulated PSM expression in LNCaP cells, perhaps as a result of binding to the mutated androgen receptor known to exist in the LNCaP cell. Overall, PSM expression is highest in the untreated LNCaP cells grown in steroid-depleted media, a situation that we propose simulates the hormone-deprived (castrate) state in-vivo. This experiment was repeated at steroid dosages ranging from 2–200 nM and at time points from 6 hours to 7 days with similar results; maximal downregulation of PSM mRNA was seen with DHT at 24 hours at doses of 2–20 nM.

Experimental Discussion

In order to better understand the biology of the human prostate in both normal and neoplastic states, we need to enhance our knowledge by studying the various proteins and other features that are unique to this important gland. Previous research has provided two valuable prostatic bio-markers, PAP and PSA, both of which have had a significant impact on the diagnosis, treatment, and management of prostate malignancies. Our present work describing the preliminary characterization of the prostate-specific membrane antigen (PSM) reveals it to be a gene with many interesting features. PSM is almost entirely prostate-specific as are PAP and PSA, and as such may enable further delineation of the unique functions and behavior of the prostate. The predicted sequence of the PSM protein (3) and its presence in the LNCaP cell membrane as determined by Western blotting and immunohistochemistry, indicate that it is an integral membrane protein. Thus, PSM provides an attractive cell surface epitope for antibody-directed diagnostic imaging and cytotoxic targeting modalities (14). The ability to synthesize the PSM antigen in-vitro and to produce tumor xenografts maintaining high levels of PSM expression provides us with a convenient and attractive model system to further study and characterize the regulation and modulation of PSM expression. Also, the high level of PSM expression in the LNCaP cells provides an excellent in-vitro model system. Since PSM expression is hormonally-responsive to steroids and may be highly expressed in hormone-refractory disease (15), it is imperative to elucidate the potential role of PSM in the evolution of androgen-independent prostate cancer. The detection of PSM mRNA expression in minute quantities in brain, salivary gland, and small intestine warrants further investigation, although these tissues were negative for expression of PSM antigen by immunohistochemistry using the 7E11-C5.3 antibody (16). In all of these tissues, particularly small intestine, we detected mRNA expression using a probe corresponding to a region of the PSM cDNA near the 3' end, whereas we were unable to detect expression when using a 5' end PSM probe. These results may indicate that the PSM mRNA transcript undergoes alternative splicing in different tissues. Previous protein studies have suggested that the 7E11-C5.3 antibody may actually detect two other slightly larger protein species in addition to the 100 kDa PSM antigen (17). These other protein species can be seen in the LNCaP lysate and membrane samples in FIG. 19. Possible origins of these proteins include alternatively spliced PSM mRNA, other genes distinct from but closely related to PSM, or different post-translational modifications of the PSM protein. We are currently investigating these possibilities.

Applicant's approach is based on prostate tissue specific promotor:enzyme or cytokine chimeras. We will examine promotor specific activation of prodrugs such as non toxic gancyclovir which is converted to a toxic metabolite by herpes simplex thymidine kinase or the prodrug 4-(bis(2 chloroethyl)amino)benzoyl-1-glutamic acid to the benzoic acid mustard alkylating agent by the *pseudomonas* carboxy peptidase G2. As these drugs are activated by the enzyme (chimera) specifically in the tumor the active drug is released only locally in the tumor environment, destroying the surrounding tumor cells. We will also examine the promotor specific activation of cytokines such as IL-12, IL-2 or GM-CSF for activation and specific antitumor vaccination. Lastly the tissue specific promotor activation of cellular death genes may also prove to be useful in this area.

Gene Therapy Chimeras

The establishment of "chimeric DNA" for gene therapy requires the joining of different segments of DNA together to make a new DNA that has characteristics of both precursor DNA species involved in the linkage. In this proposal the two pieces being linked involve different functional aspects of DNA, the promotor region which allows for the reading of the DNA for the formation of mRNA will provide specificity and the DNA sequence coding for the mRNA will provide for therapeutic functional DNA.

DNA-specified Enzyme or Cytokine mRNA:

When effective, antitumor drugs can cause the regression of very large amounts of tumor. The main requirements for antitumor drug activity is the requirement to achieve both a long enough time (t) and high enough concentration (c) (cxt) of exposure of the tumor to the toxic drug to assure sufficient cell damage for cell death to occur. The drug also must be "active" and the toxicity for the tumor greater than for the hosts normal cells (22). The availability of the drug to the tumor depends on tumor-blood flow and the drugs diffusion ability. Blood flow to the tumor does not provide for selectivity as blood flow to many normal tissues is often as great or greater than that to the tumor. The majority of chemotherapeutic cytotoxic drugs are often as toxic to normal tissue as to tumor tissue. Dividing cells are often more sensitive than non-dividing normal cells, but in many slow growing solid tumors such as prostatic cancer this does not provide for antitumor specificity (22).

Previously a means to increase tumor specificity of antitumor drugs was to utilize tumor associated enzymes to activate nontoxic prodrugs to cytotoxic agents (19). A problem with this approach was that most of the enzymes found in tumors were not totally specific in their activity and similar substrate active enzymes or the same enzyme at only slightly lower amounts was found in other tissue and thus normal tissues were still at risk for damage.

To provide absolute specificity and unique activity, viral, bacterial and fungal enzymes which have unique specificity for selected prodrugs were found which were not present in human or other animal cells. Attempts to utilize enzymes such as herpes simplex thymidine kinase, bacterial cytosine deaminase and carboxypeptidase G-2 were linked to antibody targeting systems with modest success (19). Unfortunately, antibody targeted enzymes limit the number of enzymes available per cell. Also, most antibodies do not have a high tumor target to normal tissue ratio thus normal tissues are still exposed reducing the specificity of these unique enzymes. Antibodies are large molecules that have poor diffusion properties and the addition of the enzymes molecular weight further reduces the antibodies diffusion.

Gene therapy could produce the best desired result if it could achieve the specific expression of a protein in the tumor and not normal tissue in order that a high local concentration of the enzyme be available for the production in the tumor environment of active drug (21).

Cytokines:

Applicant's research group has demonstrated that Applicant's can specifically and non-toxically "cure" an animal of an established tumor, in models of bladder or prostate cancer. The prostate cancer was the more difficult to cure especially if it was grown orthotopically in the prostate.

Our work demonstrated that tumors such as the bladder and prostate were not immunogenic, that is the administration of irradiated tumor cells to the animal prior to subsequent administration of non-irradiated tumor cells did not result in a reduction of either the number of tumor cells to produce a tumor nor did it reduce the growth rate of the tumor. But if the tumor was transfected with a retrovirus and secreted large concentrations of cytokines such as Il-2 then this could act as an antitumor vaccine and could also reduce the growth potential of an already established and growing tumor. IL-2 was the best, GM-CSF also had activity whereas a number of other cytokines were much less active. In clinical studies just using IL-2 for immunostimulation, very large concentrations had to be given which proved to be toxic. The key to the success of the cytokine gene modified tumor cell is that the cytokine is produced at the tumor site locally and is not toxic and that it stimulates immune recognition of the tumor and allows specific and non toxic recognition and destruction of the tumor. The exact mechanisms of how IL-2 production by the tumor cell activates immune recognition is not fully understood, but one explanation is that it bypasses the need for cytokine production by helper T cells and directly stimulates tumor antigen activated cytotoxic CD8 cells. Activation of antigen presenting cells may also occur.

Tissue Promotor-specific Chimera DNA Activation

Non-Prostatic Tumor Systems:

It has been observed in non-prostatic tumors that the use of promotor specific activation can selectively lead to tissue specific gene expression of the transfected gene. In melanoma the use of the tyrosinase promotor which codes for the enzyme responsible for melanin expression produced over a 50 fold greater expression of the promotor driven reporter gene expression in melanoma cells and not non melanoma cells. Similar specific activation was seen in the melanoma cells transfected when they were growing in mice. In that experiment no non-melanoma or melanocyte cell expressed the tyrosinase drive reporter gene product. The research group at Welcome Laboratories have cloned and sequenced the promoter region of the gene coding for carcinoembryonic antigen (CEA). CEA is expressed on colon and colon carcinoma cells but specifically on metastatic cytosine deaminase which converts 5 flurorocytosine into 5 fluorouracil and observed a large increase in the ability to selectively kill CEA promotor driven colon tumor cells but non dividing not dividing normal liver cells. In vivo they observed that bystander tumor cells which were not transfected with the cytosine deaminase gene were also killed, and that there was no toxicity to the host animal as the large tumors were regressing following treatment. Herpes simplex virus, (HSV), thymidine kinase similarly activates the prodrug gancyclovir to be toxic towards dividing cancer cells and HSV thymidine kinase has been shown to be specifically activatable by tissue specific promoters.

Prostatic Tumor Systems:

The therapeutic key to effective cancer therapy is to achieve specificity and spare the patient toxicity. Gene therapy may provide a key part to specificity in that nonessential tissues such as the prostate and prostatic tumors produce tissue specific proteins, such as acid phosphatase (PAP), prostate specific antigen (PSA), and a gene which we cloned, prostate-specific membrane antigen (PSM). Tissues such as the prostate contain selected tissue specific transcription factors which are responsible for binding to the promoter region of the DNA of these tissue specific mRNA. The promoter for PSA has been cloned and we are investigating its use as a prostate specific promoter for prostatic tumor cells. Usually patients who are being treated for metastatic prostatic cancer have been put on androgen deprivation therapy which dramatically reduces the expression of mRNA for PSA. PSM on the other hand increases in expression with hormone deprivation which-means it would be even more intensely expressed on patients being treated with hormone therapy. Preliminary work in collaboration with Dr. John Isaacs' Laboratory demonstrates that PSM is expressed when the human chromosome region containing the human PSM gene is transferred to the rat tumor AT-6. AT-6 is a metastatic androgen independent tumor. The same chromosome transferred into non prostate derived tissues or tumors is not expressed and thus these cells could be used as an animal model for these experiments. PSA, PSM positive Human LNCaP cells will be used for testing in nude mice.

References of the Second Series of Experiments

1. Coffey, D. S. Prostate Cancer—An overview of an increasing dilemma. Cancer Supplement, 71, 3: 880–886, 1993.
2. Chiarodo, A. National Cancer Institute roundtable on prostate cancer; future research directions. Cancer Res., 52: 2498–2505, 1991.
3. Israeli, R. S., Powell, C. T., Fair, W. R., and Heston, W. D. W. Molecular cloning of a complementary DNA encoding a prostate-specific membrane antigen. Cancer Res., 53: 227–230, 1993.
4. Horoszewicz, J. S., Kawinski, E., and Murphy, G. P. Monoclonal antibodies to a new antigenic marker in epithelial cells and serum of prostatic cancer patients. Anticancer Res., 7: 927–936, 1987.
5. Horoszewicz, J. S., Leong, S. S., Kawinski, E., Karr, J. P., Rosenthal, H., Chu, T. M., Mirand, E. A., and Murphy, G. P. LNCaP model of human prostatic carcinoma. Cancer Res., 43: 1809–1818, 1983.
6. Abdel-Nabi, H., Wright, G. L., Gulfo, J. V., Petrylak, D. P., Neal, C. E., Texter, J. E., Begun, F. P., Tyson, I., Heal, A., Mitchell, E., Purnell, G., and Harwood, S. J. Monoclonal antibodies and radioimmunoconjugates in the diagnosis and treatment of prostate cancer. Semin. Urol., 10: 45–54, 1992.
7. Stone, K. R., Mickey, D. D., Wunderli, H., Mickey, G. H., and Paulson, D. F. Isolation of a human prostate carcinoma cell line (DU-145). Int. J. Cancer, 21: 274–281, 1978.
8. Kaign, M. E., Narayan, K. S., Ohnuki, Y., and Lechner, J. F. Establishment and characterization of a human prostatic carcinoma cell line (PC-3). Invest. Urol., 17: 16–23, 1979.
9. Hsu, S. M., Raine, L., and Panger, H. Review of present methods of immunohistochemical detection. Am. J. Clin. Path. 75: 734–738, 1981.
10. Harlow, E., and Lane, D. Antibodies: A Laboratory Manual. New York: Cold Spring Harbor Laboratory, p. 449, 1988.
11. Glisin, V., Crkvenjakov, R., and Byus, C. Ribonucleic acid isolated by cesium chloride centrifugation. Biochemistry, 13: 2633–2637, 1974.
12. Aviv, H., and Leder, P. Purification of biologically active globin messenger RNA by chromatography on oligothymidylic acid cellulose. Proc. Natl. Acad. Sci. USA,. 69: 1408–1412, 1972.
13. Melton, D. A., Krieg, P. A., Rebagliati, M. R., Maniatis, T. A., Zinn, K., and Careen, M. R. Efficient in-vitro synthesis of biologically active RNA and RNA hybridization probes from plasmids containing a bacteriophage SP6 promoter. Nucl. Acids. Res. 12: 7035–7056, 1984.
14. Personal Communication from Cytogen Corporation, Princeton, N.J.
15. Axelrod, H. R., Gilman, S. C., D'Aleo, C. J., Petrylak, D., Reuter, V., Gulfo, J. V., Saad, A., Cordon-Cardo, C., and Scher, H. I. Preclinical results and human immunohistochemical studies with $^{90}$Y-CYT-356; a new prostatic cancer therapeutic agent. AUA Proceedings, Abstract 596, 1992.
16. Lopes, A. D., Davis, W. L., Rosenstraus, M. J., Uveges, A. J., and Gilman, S. C. Immunohistochemical and pharmacokinetic characterization of the site-specific immunoconjugate CYT-356 derived from antiprostate monoclonal antibody 7E11-C5. Cancer Res., 50: 6423–6429, 1990.
17. Troyer, J. K., Qi, F., Beckett, M. L., Morningstar, M. M., and Wright, G. L. Molecular characterization of the 7E11-C5 prostate tumor-associated antigen. AUA Proceedings. Abstract 482, 1993.
18. Roemer, K., Friedmann, T. Concepts and strategies for human gene therapy. FEBS. 223:212–225.
19. Antonie, P. Springer, C. J., Bagshawe, F., Searle, F., Melton, R. G., Rogers, G. T., Burke, P. J., Sherwood, R. F. Disposition of the prodrug 4-bis(2 chloroethyl)amino) benzoyl-1-glutamic acid and its active parent drug in mice. Br. J. Cancer 62:909–914, 1990.
20. Connor, J. Bannerji, R., Saito, S., Heston, W. D. W., Fair, W. R., Gilboa, E. Regression of bladder tumors in mice treated with interleukin 2 gene-modified tumor cells. J. Exp. Med. 177:1127–1134, 1993. (appendix)
21. Vile R., Hart, I. R. In vitro and in vivo targeting of gene expression to melanoma cells. Cancer Res. 53:962–967, 1993.
22. Warner, J. A., Heston, W. D. W. Future developments of nonhormonal systemic therapy for prostatic carcinoma. Urologic Clinics of North America 18:25–33, 1991.
23. Vile, R. G., Hart, I. R. Use of tissue specific expression of the herpes simplex virus thymidine kinase gene to inhibit growth of established murine melanomas following direct intratumoral injection of DNA. Cancer Res. 53:3860–3864, 1993.

Third Series of Experiments

Sensitive Detection of Prostatic Hematogenous Micrometastases Using PSA and PSM-derived Primers in the Polymerase Chain Reaction We have developed a PCR-based assay enabling sensitive detection of hematogenous micrometastases in patients with prostate cancer. We performed "nested PCR", amplifying mRNA sequences unique to prostate-specific antigen and to the prostate-specific membrane antigen, and have compared their respective results. Micrometastases were detected in 2/30 patients (6.7%) by PCR with PSA-derived primers, while PSM-derived primers detected tumor cells in 19/30 patients (63.3%). All 8 negative controls were negative with both PSA and PSM PCR. Assays were repeated to confirm results, and PCR products were verified by DNA sequencing and Southern analysis. Patients harboring circulating prostatic tumor cells as detected by PSM, and not by PSA-PCR included 4 patients previously treated with radical prostatectomy and with non-measurable serum PSA levels at the time of this assay. The significance of these findings with respect to future disease recurrence and progression will be investigated.

Improvement in the overall survival of patients with prostate cancer will depend upon earlier diagnosis. Localized disease, without evidence of extra-prostatic spread, is successfully treated with either radical prostatectomy or external beam radiation, with excellent long-term results (2,3). The major problem is that approximately two-thirds of men diagnosed with prostate cancer already have evidence of advanced extra-prostatic spread at the time of diagnosis, for which there is at present no cure (4). The use of clinical serum markers such as prostate-specific antigen (PSA) and prostatic acid phosphatase (PAP) have enabled clinicians to detect prostate carcinomas earlier and provide useful parameters to follow responses to therapy (5). Yet, despite the advent of sensitive serum PSA assays, radionuclide bone scans, CT scans and other imaging modalities, we are still unable to detect the presence of micrometastatic cells prior to their establishment of solid metastases. Previous work has been done utilizing the polymerase chain reaction to amplify mRNA sequences unique to breast, leukemia, and other malignant cells in the circulation and enable early detection of micrometastases (6,7). Recently, a PCR-based approach utilizing primers derived from the PSA DNA sequence was published (8). In this study 3/12 patients with advanced, stage D prostate cancer had detectable hematogenous micrometastases.

We have recently identified and cloned a 2.65 kb cDNA encoding the 100 kDa prostate-specific membrane antigen (PSM) recognized by the anti-prostate monoclonal antibody 7E11-C5.3 (9). PSM appears to be an integral membrane glycoprotein which is very highly expressed in prostatic tumors and metastases and is almost entirely prostate-specific (10). Many anaplastic tumors and bone metastases have variable and at times no detectable expression of PSA, whereas these lesions appear to consistently express high levels of PSM. Prostatic tumor cells that escape from the prostate gland and enter the circulation are likely to have the potential to form metastases and are possibly the more aggressive and possibly anaplastic cells, a population of cells that may not express high levels of PSA, but may retain high expression of PSM. We therefore chose to utilize DNA primers derived from the sequences of both PSA and PSM in a PCR assay to detect micrometastatic cells in the peripheral circulation. Despite the high level of amplification and sensitivity of conventional RNA PCR, we have utilized a "nested" PCR approach in which we first amplify a target sequence, and subsequently use this PCR product as the template for another round of PCR amplification with a new set of primers totally contained within the sequence of the previous product. This approach has enabled us to increase our level of detection from one prostatic tumor cell per 10,000 cells to better than one cell per ten million cells.

Experimental Details

Materials and Methods

Cells and Reagents:

LNCaP and MCF-7 cells were obtained from the American Type Culture Collection (Rockville, Md.). Details regarding the establishment and characteristics of these cell lines have been previously published (11,12). Cells were grown in RPMI 1640 media supplemented with L-glutamine, nonessential amino acids, obtained from the MSKCC Media Preparation Facility, and 5% fetal calf serum (Gibco-BRL, Gaithersburg, Md.) in a $CO_2$ incubator at 37 C. All cell media was obtained from the MSKCC Media Preparation Facility. Routine chemical reagents were of the highest grade possible and were obtained from Sigma Chemical Company, St. Louis, Mo.

Patient Blood Specimens

All blood specimens used in this study were from patients seen in the outpatient offices of urologists on staff at MSKCC. Two anti-coagulated (purple top) tubes per patient were obtained at the time of their regularly scheduled blood draws. Specimen procurement was conducted as per the approval of the MSKCC Institutional Review Board. Samples were promptly brought to the laboratory for immediate processing. Serum PSA and PAP determinations were performed by standard techniques by the MSKCC Clinical Chemistry Laboratory. PSA determinations were performed using the Tandem PSA assay (Hybritech, San Diego, Calif.). The eight blood specimens used as negative controls were from 2 males with normal serum PSA values and biopsy-proven BPH, one healthy female, 3 healthy males, one patient with bladder cancer, and one patient with acute promyelocytic leukemia.

Blood Sample Processing/RNA Extraction 4 ml of whole anticoagulated venous blood was mixed with 3 ml of ice cold phosphate buffered saline and then carefully layered atop 8 ml of Ficoll (Pharmacia, Uppsala, Sweden) in a 15-ml polystyrene tube. Tubes were centrifuged at 200×g for 30 min. at 4 C. Using a sterile pasteur pipette, the buffy coat layer (approx. 1 ml.) was carefully removed and rediluted up to 50 ml with ice cold phosphate buffered saline in a 50 ml polypropylene tube. This tube was then centrifuged at 2000×g for 30 min at 4 C. The supernatant was carefully decanted and the pellet was allowed to drip dry. One ml of RNazol B was then added to the pellet and total RNA was isolated as per manufacturers directions (Cinna/Biotecx, Houston, Tex.). RNA concentrations and purity were determined by UV spectroscopy on a Beckman DU 640 spectrophotometer and by gel analysis.

Determination of PCR Sensitivity

RNA was isolated from LNCaP cells and from mixtures of LNCaP and MCF-7 cells at fixed ratios (i.e. 1:100, 1:1000, etc.) using RNAzol B. Nested PCR was then performed as described below with both PSA and PSM primers in order to determine the limit of detection for the assay. LNCaP:MCF-7 (1:100,000). cDNA was diluted with distilled water to obtain concentrations of 1:1,000,000 and 1:10,000,000. MCF-7 cells were chosen because they have been previously tested and shown not to express PSM by PCR.

Polymerase Chain Reaction

The PSA outer primers used span portions of exons 4 and 5 to yield a 486 bp PCR product and enable differentiation between cDNA and possible contaminating genomic DNA amplification. The upstream primer sequence beginning at nucleotide 494 in PSA cDNA sequence is 5'-TACCCACTGCATCAGGAACA-3' (SEQ. ID. No. 39) and the downstream primer at nucleotide 960 is 5'-CCTTGAAGCACACCATTACA-3' (SEQ. ID. No. 40). The PSA inner upstream primer (beginning at nucleotide 559) 5'-ACACAGGCCAGGTATTTCAG-3' (SEQ. ID. No. 41) and the downstream primer (at nucleotide 894) 5'-GTCCAGCGTCCAGCACACAG-3' (SEQ. ID. No. 42) yield a 355 bp PCR product. All primers were synthesized by the MSKCC Microchemistry Core Facility. 5 g of total RNA was reverse-transcribed into cDNA in a total volume of 20 l using Superscript reverse transcriptase (Gibco-BRL) according to the manufacturers recommendations. 1 l of this cDNA served as the starting template for the outer primer PCR reaction. The 20 l PCR mix included: 0.5 U Taq polymerase (Promega Corp., Madison, Wis.), Promega reaction buffer, 1.5 mM $MgCl_2$, $_{200}$M dNTPs, and 1.0M of each primer. This mix was then transferred to a Perkin Elmer 9600 DNA thermal cycler and incubated for 25 cycles. The PCR profile was as follows: 94 C×15 sec., 60 C×15 sec., and 72 C for 45 sec. After 25 cycles, samples were placed on ice, and 1 l of this reaction mix served as the template for another round of PCR using the inner primers. The first set of tubes were returned to the thermal cycler for 25 additional cycles. PSM-PCR required the selection of primer pairs that also spanned an intron in order to be certain that cDNA and not genomic DNA were being amplified. Since the genomic DNA sequence of PSM has not yet been determined, this involved trying different primer pairs until a pair was found that produced the expected size PCR product when cDNA was amplified, but with no band produced from a genomic DNA template, indicating the presence of a large intron. The PSM outer primers yield a 946 bp product and the inner primers a 434 bp product. The PSM outer upstream primer used was 5'-ATGGGTGTTTGGTATTGACC-3' (SEQ. ID. No. 43) (beginning at nucleotide 1401) and the downstream primer (at nucleotide 2348) was 51-TGCTTGGAGCATAGATGACATGC-3' (SEQ. ID. No. 44) The PSM inner upstream primer (at nucleotide 1581) was 5'-ACTCCTTCAAGAGCGTGGCG-3' (SEQ. ID. No. 45) and the downstream primer (at nucleotide 2015) was 5'-AACACCATCCCTCCTCGAACC-3' (SEQ. ID. No. 46). cDNA used was the same as for the PSA assay. The 50 l PCR mix included: 1 U Taq Polymerase (Promega), 250M dNTPs. 10 mM-mercaptoethanol, 2 mM $MgCl_2$, and 5 l of a 10×buffer mix containing: 166 mM $NH_4SO_4$, 670 mM Tris pH 8.8, and 2 mg/ml of acetylated BSA. PCR was carried out in a Perkin Elmer 480 DNA thermal cycler with the following parameters: 94 C×4 minutes for 1 cycle, 94 C×30 sec., 58 C×1 minute, and 72 C×1 minute for 25 cycles, followed by 72 C×10 minutes. Samples were then iced and 2 l of this reaction mix was used as the template for another 25 cycles with a new reaction mix containing the inner PSM primers. cDNA quality was verified by performing control reactions using primers derived from -actin yielding a 446 bp PCR product. The upstream primer used was 5'-AGGCCAACCGCGAGAAGATGA-3' (SEQ. ID. No. 47) (exon 3) and the downstream primer was 5'-ATGTCACA AAGC-3' (SEQ. ID. No. 48) (exon 4). The entire PSA mix and 10 l of each PSM reaction mix were run on 1.5–2% agarose gels, stained with ethidium bromide and photographed in an Eagle Eye Video Imaging System (Stratagene, Torrey Pines, Calif.). Assays were repeated at least 3 times to verify results.

Cloning and Sequencing of PCR Products

PCR products were cloned into the pCR II plasmid vector using the TA cloning system (Invitrogen). These plasmids were transformed into competent $E.\ coli$ cells using standard methods (13) and plasmid DNA was isolated using Magic Minipreps (Promega) and screened by restriction analysis. TA clones were then sequenced by the dideoxy method (14) using Sequenase (U.S. Biochemical). 3–4 g of each plasmid was denatured with NaOH and ethanol precipitated. Labeling reactions were carried out according to the manufacturers recommendations using $^{35}$S-dATP (NEN), and the reactions were terminated as discussed in the same protocol. Sequencing products were then analyzed on 6% polyacrilamide/7M urea gels run at 120 watts for 2 hours. Gels were fixed for 20 minutes in 10% methanol/10% acetic acid, transferred to Whatman 3 mM paper and dried down in a vacuum dryer for 2 hours at 80 C. Gels were then autoradiographed at room temperature for 18 hours.

Southern Analysis

Ethidium-stained agarose gels of PCR products were soaked for 15 minutes in 0.2N HCl, followed by 30 minutes each in 0.5N NaOH/1.5M NaCl and 0.1M Tris pH 7.5/1.5M NaCl. Gels were then equilibrated for 10 minutes in 10×SSC (1.5M NaCl/0.15M Sodium Citrate. DNA was transferred onto Nytran nylon membranes (Schleicher and Schuell) by pressure blotting in 10×SSC with a Posi-blotter (Stratagene). DNA was cross-linked to the membrane using a UV Stratalinker (Stratagene). Blots were pre-hybridized at 65 C for 2 hours and subsequently hybridized with denatured $^{32}$P-labeled, random-primed cDNA probes (either PSM or PSA) (9,15). Blots were washed twice in 1×SSPE/0.5% SDS at 42 C and twice in 0.1×SSPE/0.5% SDS at 50 C for 20 minutes each. Membranes were air-dried and autoradiographed for 30 minutes to 1 hour at -70 C with Kodak X-Omat film.

Experimental Results

Our technique of PCR amplification with nested primers improved our level of detection of prostatic cells from approximately one prostatic cell per 10,000 MCF-7 cells to better than one cell per million MCF-7 cells, using either PSA or PSM-derived primers (FIGS. 26 and 27). This represents a substantial improvement in our ability to detect minimal disease. Characteristics of the 16 patients analyzed with respect to their clinical stage, treatment, serum PSA and PAP values, and results of our assay are shown in table 1. In total, PSA-PCR detected tumor cells in 2/30 patients (6.7%), whereas PSM-PCR detected cells in 19/30 patients (63.3%). There were no patients positive for tumor cells by PSA and not by PSM, while PSM provided 8 positive patients not detected by PSA. Patients 10 and 11 in table 1, both with very advanced hormone-refractory disease were detected by both PSA and PSM. Both of these patients have died since the time these samples were obtained. Patients 4, 7, and 12, all of whom were treated with radical prostatectomies for clinically localized disease, and all of whom have non-measurable serum PSA values 1–2 years postoperatively were positive for circulating prostatic tumor cells by PSM-PCR, but negative by PSA-PCR. A representative ethidium stained gel photograph for PSM-PCR is shown in FIG. 28. Samples run in lane A represent PCR products generated from the outer primers and samples in lanes labeled B are products of inner primer pairs. The corresponding PSM Southern blot autoradiograph is shown in FIG. 29. The sensitivity of the Southern blot analysis exceeded that of ethidium staining, as can be seen in several samples where the outer product is not visible on FIG. 28, but is detectable by Southern blotting as shown in FIG. 29. In addition, sample 3 on FIGS. 28 and 29 (patient 6 in FIG. 30) appears to contain both outer and inner bands that are smaller than the corresponding bands in the other patients. DNA sequencing has confirmed that the nucleotide sequence of these bands matches that of PSM, with the exception of a small deletion. This may represent either an artifact of PCR, alternative splicing of PSM mRNA in this patient, or a PSM mutation. We have noted similar findings with other samples on several occasions (unpublished data). All samples sequenced and analyzed by Southern analysis have been confirmed as true positives for PSA and PSM.

Experimental Details

The ability to accurately stage patients with prostate cancer at the time of diagnosis is clearly of paramount importance in selecting appropriate therapy and in predicting long-term response to treatment, and potential cure. Pre-surgical staging presently consists of physical examination, serum PSA and PAP determinations, and numerous imaging modalities including transrectal ultrasonography, CT scanning, radionuclide bone scans, and even MRI scanning. No present modality, however, addresses the issue of hematogenous micrometastatic disease and the potential negative impact on prognosis that this may produce. Previous work has shown that only a fractional percentage of circulating tumor cells will inevitably go on to form a solid metastasis (16), however, the detection of and potential quantification of circulating tumor cell burden may prove valuable in more accurately staging disease. The long-term impact of hematogenous micrometastatic disease must be studied by comparing the clinical courses of patients found to have these cells in their circulation with patients of similar stage and treatment who test negatively.

The significantly higher level of detection of tumor cells with PSM as compared to PSA is not surprising to us, since we have noted more consistent expression of PSM in prostate carcinomas of all stages and grades as compared to variable expression of PSA in more poorly differentiated and anaplastic prostate cancers. We were surprised to detect tumor cells in the three patients that had undergone radical prostatectomies with subsequent undetectable amounts of serum PSA. These patients would be considered to be surgical "cures" by standard criteria, yet they apparently continue to harbor prostatic tumor cells. It will be interesting to follow the clinical course of these patients as compared to others without PCR evidence of residual disease. We are presently analyzing larger numbers of patient samples in order to verify these findings and perhaps identify patients at risk for metastatic disease.

References

1. Boring, C. C., Squires, T. S., and Tong, T.: Cancer Statistics, 1993. CA Cancer J. Clin., 43:7–26, 1993.
2. Lepor, H., and Walsh, P. C.: Long-term results of radical prostatectomy in clinically localized prostate cancer: Experience at the Johns Hopkins Hospital. NCI Monogr., 7:117–122, 1988.
3. Bagshaw, M. A., Cox, R. S., and Ray, G. R.: Status of radiation treatment of prostate cancer at Stanford University. NCI Monogr., 7:47–60, 1988.
4. Thompson, I. M., Rounder, J. B., Teague, J. L., et al.: Impact of routine screening for adenocarcinoma of the prostate on stage distribution. J. Urol., 137:424–426, 1987.
5. Chiarodo, A.: A National Cancer Institute roundtable on prostate cancer; future research directions. Cancer Res., 51:2498–2505. 1991.
6. Wu, A., Ben-Ezra, J., and Colombero, A.: Detection of micrometastasis in breast cancer by the polymerase chain reaction. Lab. Invest., 62:109A, 1990.
7. Fey, M. F., Kulozik, A. E., and Hansen-Hagge, T. E.: The polymerase chain reaction: A new tool for the detection of minimal residual disease in hematological malignancies. Eur. J. Cancer, 27:89–94, 1991.
8. Moreno, J. G., Croce, C. M., Fischer, R., Monne, M., Vihko, P., Mulholland, S. G., and Gomella, L. G.: Detection of hematogenous micrometastasis in patients with prostate cancer. Cancer Res., 52:6110–6112, 1992.
9. Israeli, R. S., Powell, C. T., Fair, W. R., and Heston, W. D. W.: Molecular cloning of a complementary DNA encoding a prostate-specific membrane antigen. Cancer Res., 53:227–230, 1993.
10. Israeli, R. S., Powell, C. T., Corr, J. G., Fair, W. R., and Heston, W. D. W.: Expression of the prostate-specific membrane antigen (PSM).: Submitted to Cancer Research.
11. Horoszewicz, J. S., Leong, S. S., Kawinski, E., Karr, J. P., Rosenthal, H., Chu, T. M., Mirand, E. A., and Murphy, G. P.: LNCaP model of human prostatic carcinoma. Cancer Res., 43:1809–1818, 1983.
12. Soule, H. D., Vazquez, J., Long, A., Albert, S., and Brennan, M.: A human cell line from a pleural effusion derived from a breast carcinoma. J. Natl. Can. Inst., 51:1409–1416, 1973.
13. Hanahan, D.: Studies on transformation of *Escherichia coli* with plasmids. J. Mol. Biol., 166:557–580, 1983.
14. Sanger, F., Nicklen, S., and Coulson, A. R.: DNA sequencing with chain-terminating inhibitors. Proc. Natl. Acad. Sci. USA, 74:5463–5467, 1977.
15. Lundwall, A., and Lilja, H.: Molecular cloning of a human prostate specific antigen cDNA. FEBS Letters, 214:317, 1987.
16. Liotta, L. A., Kleinerman, J., and Saidel, G. M.: Quantitative relationships of intravascular tumor cells, tumor vessels, and pulmonary metastases following tumor implantation. Cancer Res., 34:997–1003, 1974.

Fourth Series of Experiments

Expression of the Prostate Specific Membrane Antigen (PSM) Diminishes the Mitogenic Stimulation of Aggressive Human Prostatic Carcinoma Cells by Transsferrin An association between transferrin and human prostate cancer has been suggested by several investigators. It has been shown that the expressed prostatic secretions of patients with prostate cancer are enriched with respect to their content of transferrin and that prostate cancer cells are rich in transferrin receptors (J. Urol. 143, 381, 1990). Transferrin derived from bone marrow has been shown to selectively stimulate the growth of aggressive prostate cancer cells (PNAS 89, 6197, 1992). We have previously reported the cloning of the cDNA encoding the 100 kDa PSM antigen (Cancer Res. 53, 208, 1993). DNA sequence analysis has revealed that a portion of the coding region, from nucleotide 1250 to 1700 possesses a 54% homology to the human transferrin receptor. PC-3 cells do not express PSM mRNA or protein and exhibit increased cell growth in response to transferrin, whereas, LNCaP prostate cancer cells which highly express PSM have a very weak response to transferring To determine whether PSM expression by prostatic cancer cells impacts upon their mitogenic response to transferrin we stably transfected the full-length PSM cDNA into the PC-3 prostate cancer cells. Clones highly expressing PSM mRNA were identified by Northern analysis and expression of PSM protein was verified by Western analysis using the anti-PSM monoclonal antibody 7E11-C5.3.

We plated $2 \times 10^4$ PC-3 or PSM-transfected PC-3 cells per well in RPMI medium supplemented with 10% fetal bovine serum and at 24 hrs. added 1 µg per ml. of holotransferrin to the cells. Cells were counted at 1 day to be highly mitogenic to the PC-3 cells. Cells were counted at 1 day to determine plating efficiency and at 5 days to determine the effect of the transferrin. Experiments were repeated to verify the results.

We found that the PC-3 cells experienced- an average increase of 275% over controls, whereas the LNCaP cells were only stimulated 43%. Growth kinetics revealed that the PSM-transfected PC-3 cells grew 30% slower than native PC-3 cells. This data suggests that PSM expression in aggressive, metastatic human prostate cancer cells significantly abrogates their mitogenic response to transferrin.

The use of therapeutic vaccines consisting of cytokine-secreting tumor cell preparations for the treatment of established prostate cancer was investigated in the Dunning R3327-MatLyLu rat prostatic adenocarcinoma model. Only IL-2 secreting, irradiated tumor cell preparations were capable of curing animals from subcutaneously established tumors, and engendered immunological memory that protected the animals from another tumor challenge. Immunotherapy was less effective when tumors were induced orthotopically, but nevertheless led to improved outcome, significantly delaying, and occasionally preventing recurrence of tumors after resection of the cancerous prostate. Induction of a potent immune response in tumor bearing animals against the nonimmunogenic MatLyLu tumor supports the view that active immunotherapy of prostate cancer may have therapeutic benefits.

What is claimed is:

1. A method of detecting micrometastic prostate tumor cells in a subject which comprises:
   a) obtaining a suitable sample of mRNA from the subject;
   b) contacting the mRNA sample under hybridizing conditions with a labeled nucleic acid probe which: (1) is at least 15 nucleotides in length and (2) hybridizes specifically to a nucleic acid having a sequence which is complementary to a sequence present in the sequence set forth in SEQ ID NO. 1;
   c) removing any unbound labeled nucleic acid probe; and
   d) detecting the presence of labeled nucleic acid probe hybridized to the mRNA;
   e) comparing the amount of labeled nucleic acid probe measured in step d) with an amount measured in a negative control sample which does not have micrometastic prostate tumor cells, wherein a higher amount measured in step d) compared to the amount measured in the control sample indicates the detection of micrometastic prostate tumor cells in the subject.

2. A method of detecting micrometastic prostate tumor cells in a subject which comprises:
   a) obtaining a suitable sample of mRNA from the subject;
   b) reverse transcribing the mRNA to generate a single-stranded cDNA;
   c) contacting the single-stranded cDNA under hybridizing conditions with a labeled nucleic acid probe which: 1) is at least 15 nucleotides in length; and 2) hybridizes specifically to a nucleic acid having a sequence set forth in SEQ ID NO:1;
   d) removing any unbound labeled nucleic acid probe; and
   e) detecting the presence of labeled nucleic acid probe hybridized to the cDNA;
   f) comparing the amount of labeled nucleic acid probe measured in step e) with an amount measured in a negative control sample which does not have micrometastic prostate tumor cells, wherein a higher amount measured in step e) compared to the amount measured in the control sample indicates the detection of micrometastic prostate tumor cells in the subject.

3. A method of detecting micrometastic prostate tumor cells in a subject which comprises:
   a) obtaining a suitable sample of mRNA from the subject;
   b) generating a double-stranded mRNA-cDNA duplex from the mRNA;
   c) contacting the duplex from (b) with one primer having a sequence which is complementary to a portion of the sequence set forth in SEQ ID NO:1 and a second primer having a sequence which comprises a different portion of the sequence set forth in SEQ ID NO:1;
   d) amplifying the nucleic acid from (c) using a polymerase chain reaction to obtain an amplification product;
   e) contacting the amplification product of (d) under hybridizing conditions with a labeled nucleic acid probe which: 1) is at least 15 nucleotides in length; 2) hybridizes specifically to a nucleic acid having a sequence set forth in SEQ ID NO. 1;

f) removing any unbound labeled nucleic acid probe; and g) detecting the presence of labeled nucleic acid probe hybridized to the amplification product;

h) comparing the amount of labeled nucleic acid probe measured in step g) with an amount measured in a negative control sample which does not have micrometastic prostate tumor cells, wherein a higher amount measured in step g) compared to the amount measured in the control sample indicates the detection of micrometastic prostate tumor cells in the subject.

4. A method of detecting micrometastic prostate tumor cells in a subject which comprises:

a) obtaining a suitable sample of mRNA from the subject;

b) generating a double-stranded mRNA-cDNA duplex from the mRNA;

c) contacting the duplex from (b) with one primer having a sequence which is complementary to a portion of the sequence set forth in SEQ ID NO:1 and a second primer having a sequence which comprises a different portion of the sequence set forth in SEQ ID NO:1;

d) amplifying the nucleic acid from (c) using a polymerase chain reaction to obtain an amplification product;

e) contacting the amplification product of (d) under hybridizing conditions with a labeled nucleic acid probe which: 1) is at least 15 nucleotides in length; and 2) hybridizes specifically to a nucleic acid having a sequence complementary to the DNA sequence set forth in SEQ ID NO:1;

f) removing any unbound labeled nucleic acid probe; and g) detecting the presence of labeled nucleic acid probe hybridized to the amplification products;

h) comparing the amount of labeled nucleic acid probe measured in step g) with an amount measured in a negative a control sample which does not have micrometastic prostate tumor cells, wherein a higher amount measured in step g) compared to the amount measured in the control sample indicates the detection of micrometastic prostate tumor cells in the subject.

5. A method of detecting the presence of a nucleic acid encoding a prostate specific membrane antigen in a subject which comprises:

a) obtaining a suitable sample of mRNA from the subject;

b) generating a double-stranded cDNA from the mRNA;

c) contacting the double-stranded cDNA from (b) with one primer having a sequence which is complementary to a portion of the sequence set forth in SEQ ID NO:1 and a second primer having a sequence which comprises a different portion of the sequence set forth in SEQ ID NO:1;

d) amplifying the double stranded cDNA using a polymerase chain reaction to obtain an amplification product;

e) contacting the amplification product of (d) under hybridizing conditions with a labeled nucleic acid probe which 1) is at least 15 nucleotides in length; 2) hybridizes specifically to a nucleic acid having a sequence complementary to the DNA sequence set forth in SEQ ID NO:1;

f) removing any unbound labeled nucleic acid probe; and g) detecting the presence of labeled nucleic acid probe hybridized to the amplification product so as to thereby detect the presence of a nucleic acid encoding a prostate specific membrane antigen in a subject.

6. A method of detecting the presence of a nucleic acid encoding a prostate specific membrane antigen in a subject which comprises:

a) obtaining a suitable sample of mRNA from the subject;

b) generating a double-stranded cDNA from the mRNA;

c) contacting the double-stranded cDNA from (b) with one primer having a sequence which is complementary to a portion of the sequence set forth in SEQ ID NO:1 and a second primer having a sequence which comprises a different portion of the sequence set forth in SEQ ID NO:1;

d) amplifying the double stranded cDNA using a polymerase chain reaction to obtain an amplification product;

e) contacting the amplification product of (d) under hybridizing conditions with a labeled nucleic acid probe which 1) is at least 15 nucleotides in length; 2) hybridizes specifically to a nucleic acid having a sequence set forth in SEQ ID NO:1;

f) removing any unbound labeled nucleic acid probe; and g) detecting the presence of labeled nucleic acid probe hybridized to the amplification product so as to thereby detect the presence of a nucleic acid encoding a prostate specific membrane antigen in a subject.

7. The method of any one of claims 1–6, wherein the sample is blood, lymph nodes, or bone marrow.

* * * * *